US008029558B2

(12) United States Patent  
Ta et al.

(10) Patent No.: US 8,029,558 B2  
(45) Date of Patent: Oct. 4, 2011

(54) STENT AND CATHETER ASSEMBLY AND METHOD FOR TREATING BIFURCATIONS

(75) Inventors: Diem Uyen Ta, San Jose, CA (US); Caroline Wu, San Jose, CA (US); Brenna K. Hearn, San Francisco, CA (US); Daniel L. Cox, Palo Alto, CA (US); Leonard D. Barbod, San Diego, CA (US); Jessie Delgado, Murrieta, CA (US); Stephen Dirk Pacetti, San Jose, CA (US); Thomas Ray Hatten, Los Altos, CA (US); David K. Wrolstad, Temecula, CA (US); Kenneth Kay Armstrong, Riverside, CA (US); Darrin J. Kent, Murrieta, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 75 days.

(21) Appl. No.: 11/483,300

(22) Filed: Jul. 7, 2006

(65) Prior Publication Data

US 2008/0009932 A1    Jan. 10, 2008

(51) Int. Cl.  
*A61F 2/06* (2006.01)

(52) U.S. Cl. ...................................... 623/1.35; 623/1.15

(58) Field of Classification Search .................. 623/1.15, 623/1.16, 1.2, 1.34, 1.35, 1.42, 1.46, 2.17–2.19  
See application file for complete search history.

(56) References Cited

U.S. PATENT DOCUMENTS

| | | | |
|---|---|---|---|
| 2,978,787 A | 5/1961 | Leibig | |
| 2,990,605 A | 7/1961 | Densyk | |
| 3,029,819 A | 4/1962 | Starks | |
| 3,096,560 A | 7/1963 | Liebig | |
| 3,142,067 A | 7/1964 | Liebig | |
| 3,657,744 A | 4/1972 | Ersek | |
| 3,908,662 A | 9/1975 | Razgulov et al. | |

(Continued)

FOREIGN PATENT DOCUMENTS

EP    0 466 518 A3    1/1992

(Continued)

OTHER PUBLICATIONS

"Nest", Dec. 18, 2009, merriam-webster online, pp. 1-2.*

(Continued)

*Primary Examiner* — Thomas J Sweet  
*Assistant Examiner* — Rebecca Straszheim  
(74) *Attorney, Agent, or Firm* — Fulwider Patton LLP

(57) ABSTRACT

An improved stent design and stent delivery catheter assembly for repairing a main vessel and a side branch vessel forming a bifurcation. The stent includes rings aligned along a common longitudinal axis and connected by links, where the stent has one or more portals for aligning with and partially expanding into the opening to the side branch vessel. The stent is implanted at a bifurcation so that the main stent section is in the main vessel, and the portal section covers at least a portion of the opening to the side branch vessel. A second stent can be implanted in the side branch vessel and abut the expanded central section to provide full coverage of the bifurcated area in the main vessel and the side branch vessel. Radiopaque markers on the stent and on the tip of the delivery catheter assist in aligning the portal section with the opening to the side branch vessel.

21 Claims, 35 Drawing Sheets

U.S. PATENT DOCUMENTS

| | | |
|---|---|---|
| 3,945,052 A | 3/1976 | Liebig |
| 4,041,931 A | 8/1977 | Elliott et al. |
| 4,047,252 A | 9/1977 | Liebig et al. |
| 4,061,134 A | 12/1977 | Samuels et al. |
| 4,108,161 A | 8/1978 | Samuels et al. |
| 4,140,126 A | 2/1979 | Choudhury |
| 4,193,137 A | 3/1980 | Heck |
| 4,202,349 A | 5/1980 | Jones |
| 4,214,587 A | 7/1980 | Sakura, Jr. |
| 4,517,687 A | 5/1985 | Liebig et al. |
| 4,560,374 A | 12/1985 | Hammerslag |
| 4,562,596 A | 1/1986 | Kornberg |
| 4,577,631 A | 3/1986 | Kreamer |
| 4,617,932 A | 10/1986 | Kornberg |
| 4,652,263 A | 3/1987 | Herweck et al. |
| 4,693,249 A | 9/1987 | Schenck et al. |
| 4,728,328 A | 3/1988 | Hughes et al. |
| 4,739,762 A | 4/1988 | Palmaz |
| 4,787,899 A | 11/1988 | Lazarus |
| 4,793,348 A | 12/1988 | Palmaz |
| 4,795,458 A | 1/1989 | Regan |
| 4,795,465 A | 1/1989 | Marten |
| 4,830,003 A | 5/1989 | Wolff et al. |
| 4,872,874 A | 10/1989 | Taheri |
| 4,878,906 A | 11/1989 | Lindemann et al. |
| 4,892,539 A | 1/1990 | Koch |
| 4,969,890 A | 11/1990 | Sugita et al. |
| 4,969,896 A | 11/1990 | Shors |
| 4,994,071 A | 2/1991 | MacGregor |
| 5,026,377 A | 6/1991 | Burton et al. |
| 5,047,050 A | 9/1991 | Arpesani |
| 5,104,399 A | 4/1992 | Lazarus |
| 5,108,424 A | 4/1992 | Hoffman, Jr. et al. |
| 5,127,919 A | 7/1992 | Ibrahim et al. |
| 5,156,619 A | 10/1992 | Ehrenfeld |
| 5,178,630 A | 1/1993 | Schmitt |
| 5,178,634 A | 1/1993 | Ramos Martinez |
| 5,197,976 A | 3/1993 | Herweck et al. |
| 5,197,977 A | 3/1993 | Hoffman, Jr. et al. |
| 5,304,220 A | 4/1994 | Maginot |
| 5,316,023 A | 5/1994 | Palmaz et al. |
| 5,360,443 A | 11/1994 | Barone et al. |
| 5,443,497 A | 8/1995 | Venbrux |
| 5,443,498 A | 8/1995 | Fontaine |
| 5,456,712 A | 10/1995 | Maginot |
| 5,462,530 A | 10/1995 | Jang |
| 5,505,702 A | 4/1996 | Arney |
| 5,507,769 A | 4/1996 | Marin et al. |
| 5,522,880 A | 6/1996 | Barone et al. |
| 5,527,355 A | 6/1996 | Ahn |
| 5,562,724 A | 10/1996 | Vorwerk et al. |
| 5,562,726 A | 10/1996 | Chuter |
| D376,011 S | 11/1996 | Nunokawa |
| 5,571,167 A | 11/1996 | Maginot |
| 5,571,170 A | 11/1996 | Palmaz et al. |
| 5,571,171 A | 11/1996 | Barone et al. |
| 5,571,173 A | 11/1996 | Parodi |
| 5,575,817 A | 11/1996 | Martin |
| 5,578,071 A | 11/1996 | Parodi |
| 5,578,072 A | 11/1996 | Barone et al. |
| 5,591,222 A | 1/1997 | Susawa et al. |
| 5,591,228 A | 1/1997 | Edoga |
| 5,591,229 A | 1/1997 | Parodi et al. |
| 5,607,444 A | 3/1997 | Lam |
| 5,613,980 A | 3/1997 | Chauhan |
| 5,617,878 A | 4/1997 | Taheri |
| 5,632,762 A | 5/1997 | Myler |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,669,924 A | 9/1997 | Shaknovich |
| 5,676,696 A | 10/1997 | Marcade |
| 5,676,697 A | 10/1997 | McDonald |
| 5,683,450 A | 11/1997 | Goicoechea et al. |
| 5,683,452 A | 11/1997 | Barone et al. |
| 5,683,453 A | 11/1997 | Palmaz |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,517 A | 12/1997 | Marin et al. |
| 5,697,971 A | 12/1997 | Fischell et al. |
| 5,709,713 A | 1/1998 | Evans et al. |
| 5,713,917 A | 2/1998 | Leonhardt et al. |
| 5,718,724 A | 2/1998 | Goicoechea et al. |
| 5,720,735 A | 2/1998 | Dorros |
| 5,749,825 A | 5/1998 | Fischell et al. |
| 5,755,734 A | 5/1998 | Richter et al. |
| 5,755,735 A | 5/1998 | Richter et al. |
| 5,755,771 A | 5/1998 | Penn et al. |
| 5,776,180 A | 7/1998 | Goicoechea et al. |
| 5,782,906 A | 7/1998 | Marshall et al. |
| 5,800,508 A | 9/1998 | Goicoechea et al. |
| 5,800,520 A | 9/1998 | Fogarty et al. |
| 5,827,229 A | 10/1998 | Auth et al. |
| 5,827,320 A | 10/1998 | Richter et al. |
| 5,893,887 A | 4/1999 | Jayaraman |
| 5,895,407 A | 4/1999 | Jayaraman |
| 5,916,234 A | 6/1999 | Lam |
| 5,916,263 A | 6/1999 | Goicoechea et al. |
| 5,919,225 A | 7/1999 | Lau et al. |
| 5,921,995 A | 7/1999 | Kleshinski |
| 5,925,075 A | 7/1999 | Myers et al. |
| 5,938,696 A | 8/1999 | Goicoechea et al. |
| 5,954,693 A | 9/1999 | Barry |
| 5,972,017 A | 10/1999 | Berg et al. |
| 5,976,155 A | 11/1999 | Foreman et al. |
| 6,017,363 A | 1/2000 | Hojeibane |
| 6,030,413 A | 2/2000 | Lazarus |
| 6,030,414 A | 2/2000 | Taheri |
| 6,030,415 A | 2/2000 | Chuter |
| 6,033,434 A | 3/2000 | Borghi |
| 6,033,435 A | 3/2000 | Penn et al. |
| 6,039,754 A | 3/2000 | Caro |
| 6,048,361 A | 4/2000 | Von Oepen |
| 6,051,020 A | 4/2000 | Goicoechea et al. |
| 6,059,824 A | 5/2000 | Taheri |
| 6,068,655 A | 5/2000 | Seguin et al. |
| 6,090,133 A | 7/2000 | Richter et al. |
| 6,099,497 A | 8/2000 | Adams et al. |
| 6,099,560 A | 8/2000 | Penn et al. |
| 6,106,548 A | 8/2000 | Roubin et al. |
| 6,117,117 A | 9/2000 | Mauch |
| 6,118,667 A | 9/2000 | Webster et al. |
| 6,129,738 A | 10/2000 | Lashinski et al. |
| 6,129,754 A | 10/2000 | Kanesaka et al. |
| 6,129,756 A | 10/2000 | Kugler et al. |
| 6,132,460 A | 10/2000 | Thompson |
| 6,149,682 A | 11/2000 | Frid |
| 6,152,945 A | 11/2000 | Bachinski |
| 6,152,957 A | 11/2000 | Jang |
| 6,159,238 A | 12/2000 | Killion |
| 6,165,195 A | 12/2000 | Wilson et al. |
| 6,183,509 B1 | 2/2001 | Dibie |
| 6,187,036 B1 | 2/2001 | Shaolian et al. |
| 6,203,568 B1 | 3/2001 | Lombardi et al. |
| 6,210,380 B1 | 4/2001 | Mauch |
| 6,210,429 B1 | 4/2001 | Vardi et al. |
| 6,221,098 B1 | 4/2001 | Wilson et al. |
| 6,254,593 B1 | 7/2001 | Wilson |
| 6,258,116 B1 | 7/2001 | Hojeibane |
| 6,264,682 B1 | 7/2001 | Wilson et al. |
| 6,270,524 B1 | 8/2001 | Kim |
| 6,290,673 B1 | 9/2001 | Shanley |
| 6,325,826 B1 | 12/2001 | Vardi |
| 6,346,089 B1 | 2/2002 | Dibie |
| 6,358,274 B1 | 3/2002 | Thompson |
| 6,361,555 B1 | 3/2002 | Wilson |
| 6,544,218 B1 * | 4/2003 | Choi ................ 604/96.01 |
| 6,652,578 B2 | 11/2003 | Bailey et al. |
| 6,709,440 B2 * | 3/2004 | Callol et al. ........... 606/108 |
| 6,749,628 B1 * | 6/2004 | Callol et al. ........... 623/1.15 |
| 6,918,928 B2 * | 7/2005 | Wolinsky et al. ....... 623/1.34 |
| 7,341,598 B2 | 3/2008 | Davidson et al. |
| 2001/0002435 A1 * | 5/2001 | Berg et al. ............. 604/265 |
| 2001/0010013 A1 | 7/2001 | Cox et al. |

| | | | |
|---|---|---|---|
| 2001/0029397 A1 | 10/2001 | Thompson | |
| 2001/0037137 A1 | 11/2001 | Vardi et al. | |
| 2001/0049548 A1 | 12/2001 | Vardi et al. | |
| 2001/0056297 A1 | 12/2001 | Hojeibane | |
| 2002/0035389 A1 | 3/2002 | Richter | |
| 2002/0042650 A1 | 4/2002 | Vardi et al. | |
| 2002/0055770 A1* | 5/2002 | Doran et al. | 623/1.15 |
| 2002/0183763 A1* | 12/2002 | Callol et al. | 606/108 |
| 2003/0125802 A1* | 7/2003 | Callol et al. | 623/1.35 |
| 2003/0139796 A1 | 7/2003 | Sequin et al. | |
| 2003/0144724 A1 | 7/2003 | Murray, III | |
| 2003/0181969 A1 | 9/2003 | Kugler et al. | |
| 2003/0195606 A1* | 10/2003 | Davidson et al. | 623/1.11 |
| 2003/0204244 A1* | 10/2003 | Stiger | 623/1.16 |
| 2003/0212324 A1* | 11/2003 | Knapp et al. | 600/425 |
| 2004/0102838 A1* | 5/2004 | Killion et al. | 623/1.16 |
| 2004/0186508 A1 | 9/2004 | Adams et al. | |
| 2004/0267352 A1* | 12/2004 | Davidson et al. | 623/1.15 |
| 2007/0073373 A1* | 3/2007 | Bonsignore | 623/1.2 |
| 2007/0239251 A1* | 10/2007 | Prabhu et al. | 623/1.2 |
| 2009/0228088 A1* | 9/2009 | Lowe et al. | 623/1.2 |

FOREIGN PATENT DOCUMENTS

| | | |
|---|---|---|
| EP | 0 747 020 A2 | 12/1996 |
| EP | 0 804 907 A2 | 11/1997 |
| EP | 0 857 471 | 10/1998 |
| EP | 0 897 700 A1 | 2/1999 |
| EP | 0 904 745 A2 | 3/1999 |
| EP | 0 461 791 A1 | 12/1999 |
| WO | WO 95/16406 | 6/1995 |
| WO | WO 95/21592 | 8/1995 |
| WO | WO 96/23455 | 8/1996 |
| WO | WO 96/24306 | 8/1996 |
| WO | WO 96/24308 | 8/1996 |
| WO | WO 96/34580 | 11/1996 |
| WO | WO 97/07752 | 3/1997 |
| WO | WO 97/15346 | 5/1997 |
| WO | WO 97/16217 | 5/1997 |
| WO | 9741803 | 11/1997 |
| WO | WO 97/45073 | 12/1997 |
| WO | WO 98/19628 | 5/1998 |
| WO | WO 98/36709 | 8/1998 |
| WO | WO 99/04726 | 2/1999 |
| WO | WO 00/07523 | 2/2000 |
| WO | WO 01/21095 A2 | 3/2001 |
| WO | WO 01/52769 A1 | 7/2001 |
| WO | WO 02/091951 A2 | 11/2002 |
| WO | WO 02091951 * | 11/2002 |
| WO | WO 03/051234 | 6/2003 |
| WO | WO 03051234 * | 6/2003 |

OTHER PUBLICATIONS

Lawrence, David D., Jr., M.D., et al., Percutaneous Endovascular Graft: Experimental Evaluation, *Radiology*, 1987, pp. 357-360, vol. 163, No. 2.

Yoshioka, Tetsuya, et al., Self-Expanding Endovascular Graft: An Experimental Study in Dogs, *Radiology*, 1989, pp. 673-676, vol. 170.

Mirich, David, M.D., et al., Percutaneously Placed Endovascular Grafts for Aortic Aneurysms: Feasibility Study. *Radiology*, 1989, pp. 1033-1037, vol. 179, No. 3, Part 2.

Parodi, J.C., M.D., et al., Transfemoral Intraluminal Graft Implantation for Abdominal Aortic Aneurysms, *Annals of Vascular Surgery*, 1991, pp. 491-499, vol. 5, No. 6.

Chuter, Timothy A.M., et al., Transfemoral Endovascular aortic Graft Placement, *Journal of Vascular Surgery*, Aug. 1992, pp. 185-196.

Bard XT Carina Bifurcate Stent (Brochure) (Undated).

* cited by examiner

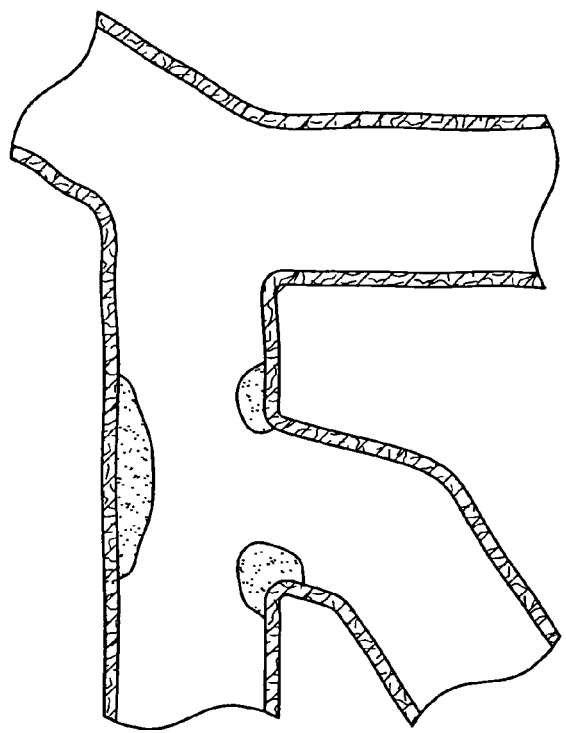 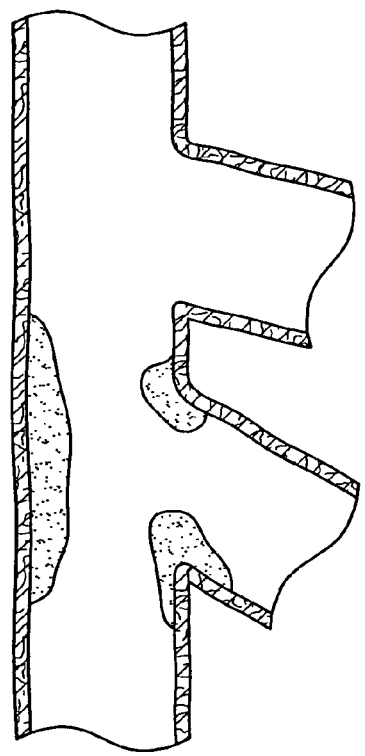
FIG. 18A    FIG. 18B
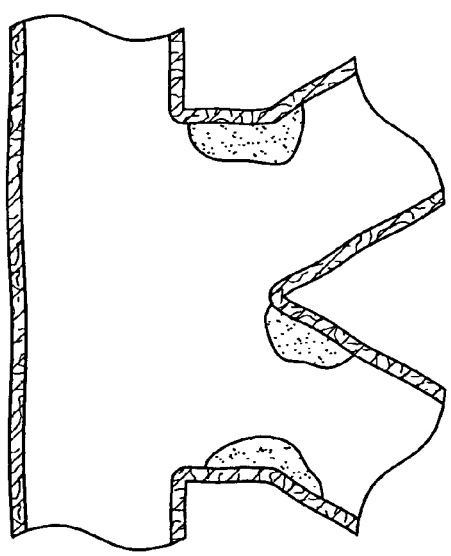 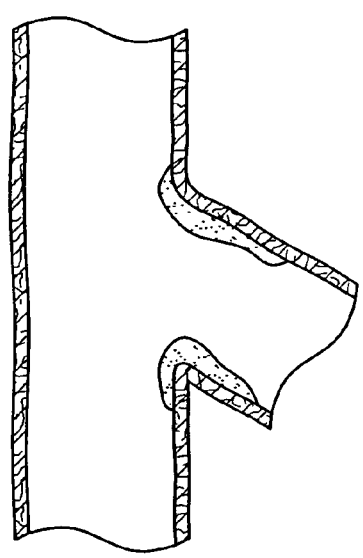
FIG. 18C    FIG. 18D

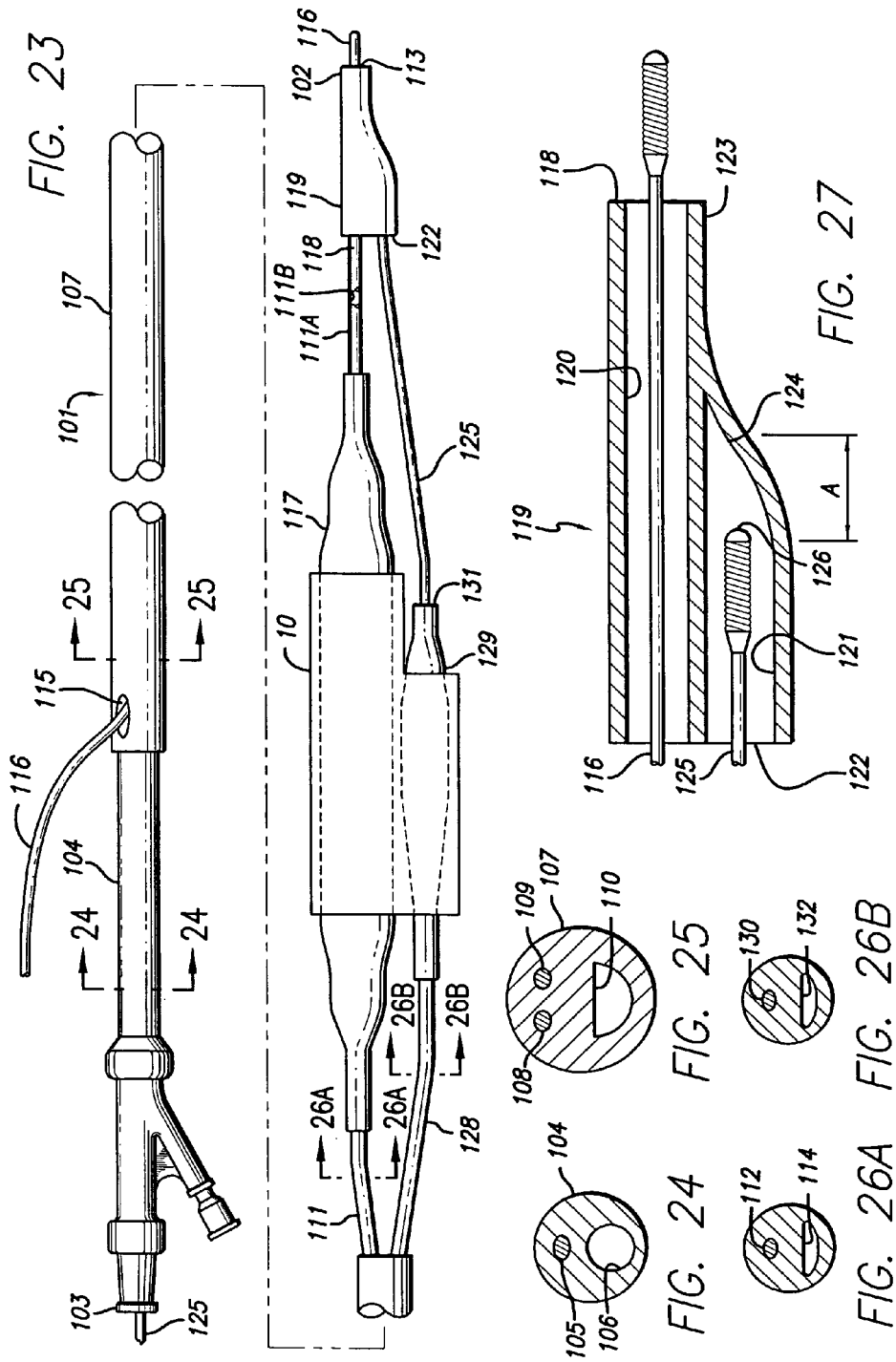

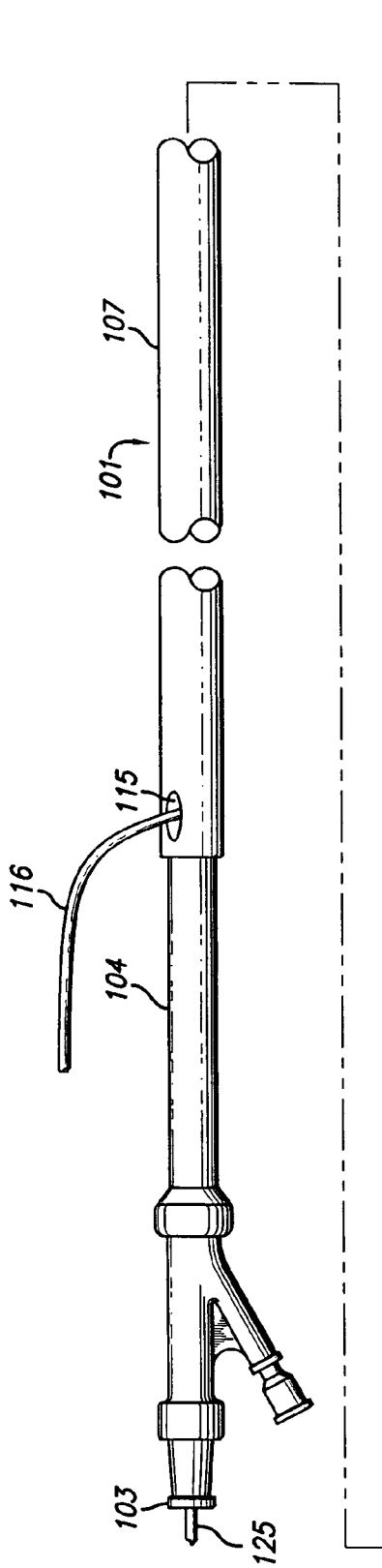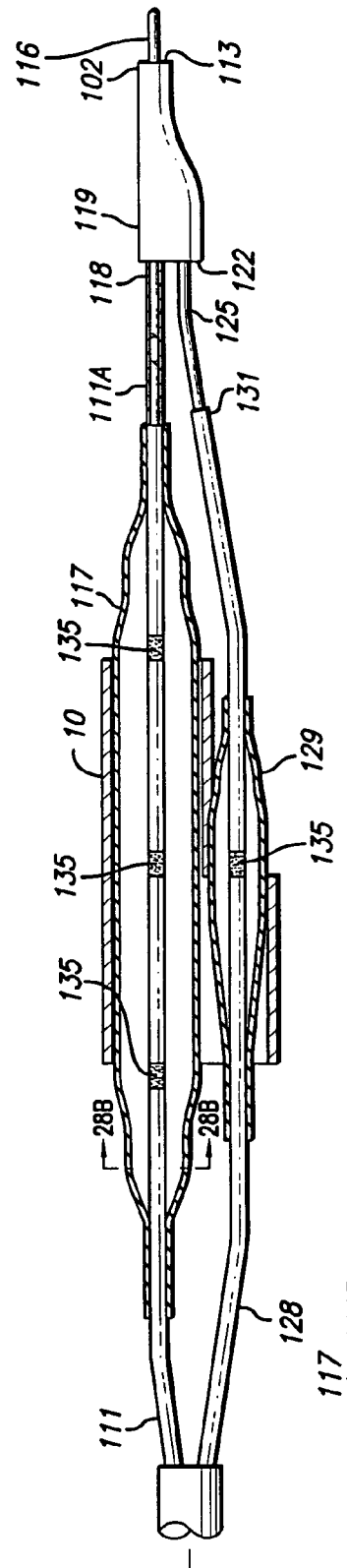
FIG. 28A
FIG. 28B

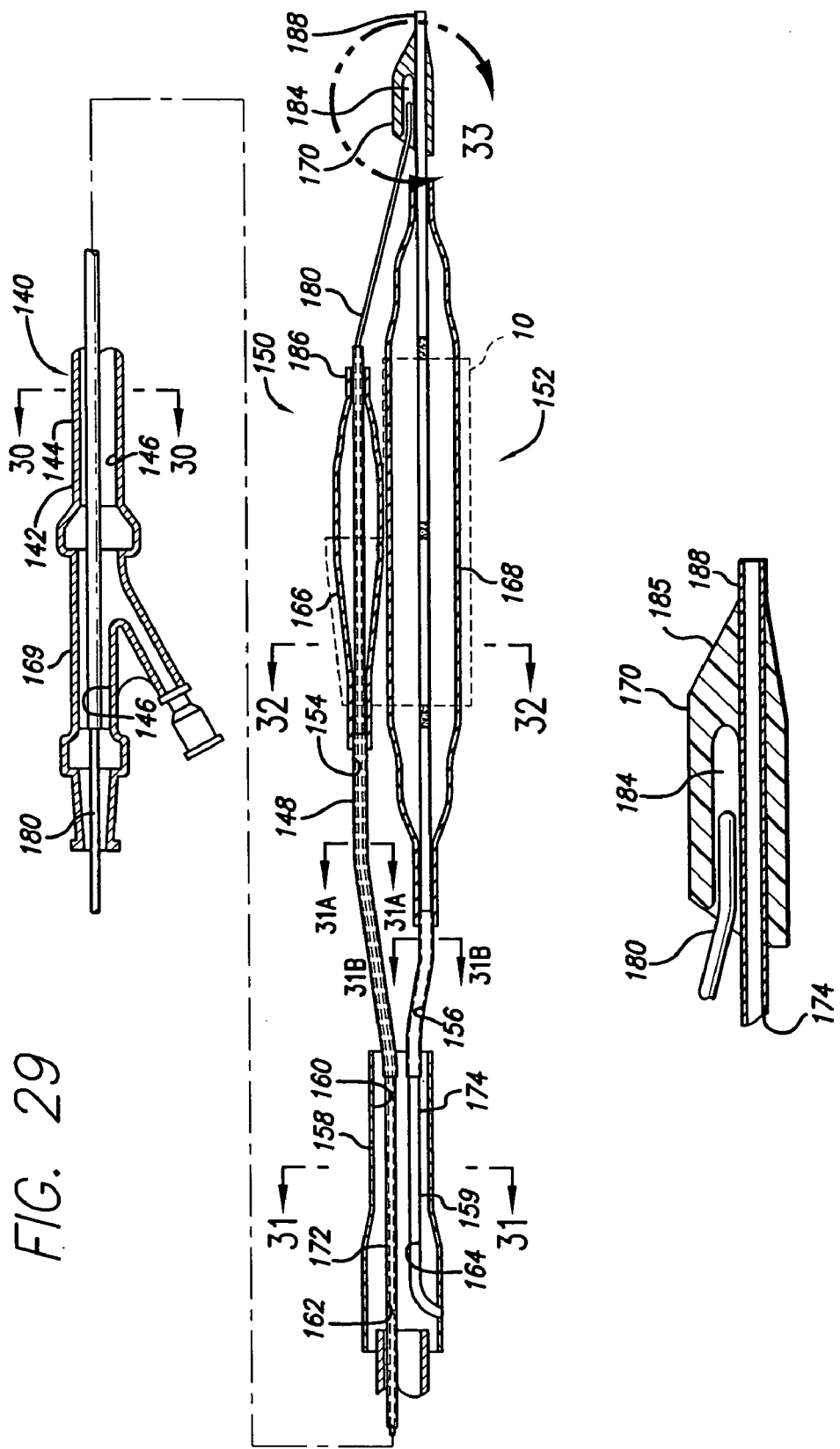

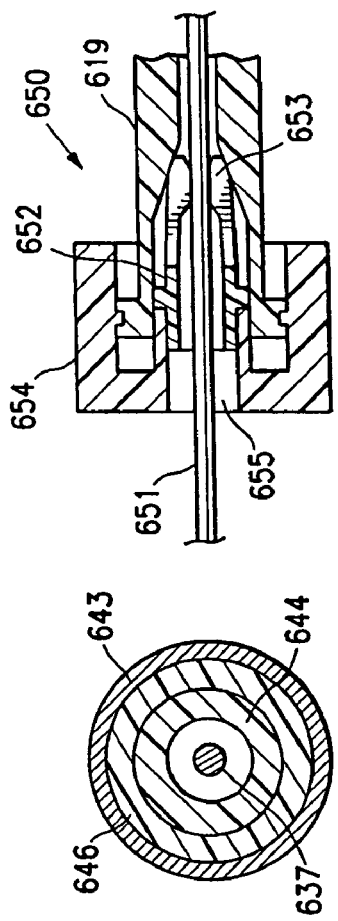
FIG. 52
FIG. 51
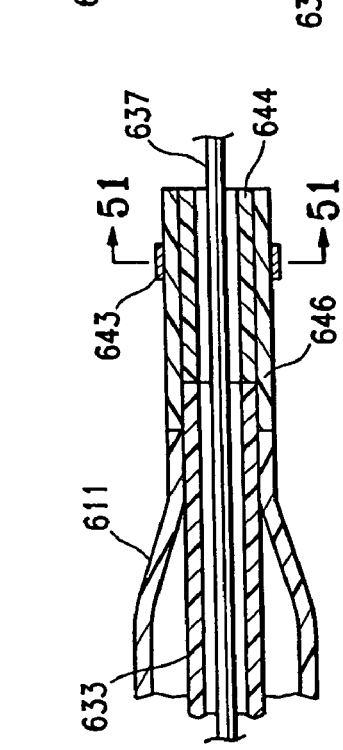
FIG. 50
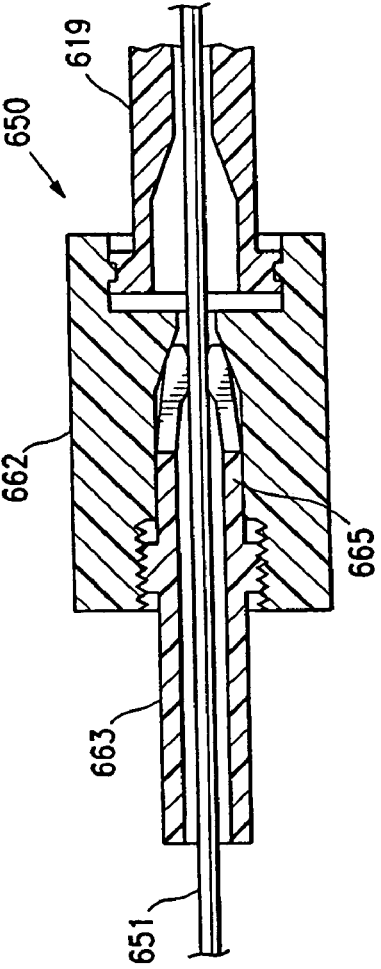
FIG. 54
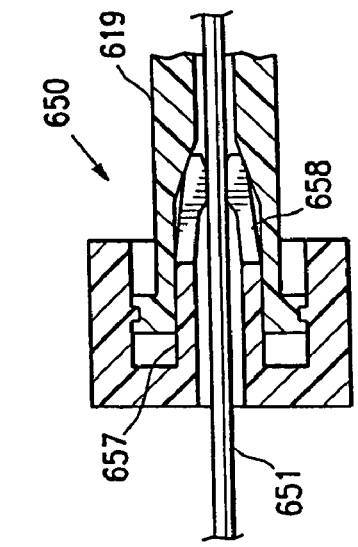
FIG. 53

STENT AND CATHETER ASSEMBLY AND METHOD FOR TREATING BIFURCATIONS

BACKGROUND OF THE INVENTION

The invention relates to stents and stent delivery and deployment assemblies for use at a bifurcation and, more particularly, one or more stents for repairing bifurcations, blood vessels that are diseased, and a method and apparatus for delivery and implantation of the stents.

Stents conventionally repair blood vessels that are diseased. Stents are generally hollow and cylindrical in shape and have terminal ends that are generally perpendicular to their longitudinal axis. In use, the conventional stent is positioned at the diseased area of a vessel and, after deployment, the stent provides an unobstructed pathway for blood flow.

Repair of vessels that are diseased at a bifurcation is particularly challenging since the stent must be precisely positioned, provide adequate coverage of the disease, provide access to any diseased area located distally to the bifurcation, and maintain vessel patency in order to allow adequate blood flow to reach the myocardium. Therefore, the stent must provide adequate coverage to the diseased portion of the bifurcated vessel, without compromising blood flow, and extend to a point within and beyond the diseased portion. Where the stent provides coverage to the vessel at the diseased portion, yet extends into the vessel lumen at the bifurcation, the diseased area is treated, but blood flow may be compromised in other portions of the bifurcation. Unapposed stent elements may promote lumen compromise during neointimal formation and healing, producing restenosis and requiring further procedures. Moreover, by extending into the vessel lumen at the bifurcation, the stent may block access to further interventional procedures.

Conventional stents are designed to repair areas of blood vessels that are removed from bifurcations and, therefore, are associated with a variety of problems when attempting to use them to treat lesions at a bifurcation. Conventional stents are normally deployed so that the entire stent is either in the parent vessel or the proximal portion of the stent is in the parent vessel and the distal portion is located in the side branch vessel. In both cases, either the side branch vessel (former case) or the parent vessel (later case), would become "jailed" by the stent struts. This technique repairs one vessel at the bifurcation at the expense of jailing or obstructing the alternate vessel.

Blood flow into the jailed vessel would be compromised as well as future access and treatment into the distal portion of the jailed vessel.

Alternatively, access into a jailed vessel can be attained by carefully placing a guide wire through the stent and subsequently tracking a balloon catheter through the stent struts. The balloon could then be expanded, thereby deforming the stent struts and forming an opening into the previously jailed vessel. The cell to be spread apart is currently randomly and blindly selected by crossing the deployed stent with a guide wire. The drawback with this approach is that there is no way to determine or guarantee that the main-vessel stent struts are properly oriented with respect to the side branch or that an appropriate stent cell has been selected by the wire for dilatation. The aperture created often does not provide a clear opening and creates a major distortion in the surrounding stent struts. A further drawback with this approach is that it is difficult to determine if the stent struts in the stented vessel have been properly oriented and spread apart to provide a clear opening for stenting the jailed vessel. This technique also causes stent deformation to occur in the area adjacent to the carina, pulling the stent away from the vessel wall and partially obstructing flow in the originally non-jailed vessel. Deforming the stent struts to regain access into the previously jailed vessel is also a complicated and time consuming procedure associated with attendant risks to the patient and is typically performed only if considered an absolute necessity. Vessels which supply a considerable amount of blood to the myocardium and may be responsible for the onset of angina or a myocardial infarct typify what would necessitate the subsequent strut deformation in order to reestablish blood flow into the vessel. The risks of procedural complications during this subsequent deformation are considerably higher than stenting in normal vessels. The inability to place a guide wire through the jailed lumen in a timely fashion could restrict blood supply and begin to precipitate symptoms of angina or even cardiac arrest. In addition, disturbed hemodynamics and subsequent thrombus formation at the jailed site could further compromise blood flow into the side branch.

Plaque shift is also a phenomena which is of concern when deploying a stent across a bifurcation. Plaque shift occurs when treatment of disease or plaque in one vessel causes the plaque to shift into another location. This is of greatest concern when the plaque is located on the carina or the apex of the bifurcation. During treatment of the disease the plaque may shift from one side of the carina to the other thereby shifting the obstruction from one vessel to the alternate vessel.

In another prior art method of implanting stents, a "T" stent procedure includes implanting a stent in the side branch ostium of the bifurcation followed by stenting the main vessel across the side branch and subsequently deforming the struts as previously described, to allow blood flow and access into the side branch vessel. Alternatively, a stent is deployed in the parent vessel and across the side branch origin followed by subsequent strut deformation as to access the side branch previously described, and finally a stent is placed into the side branch vessel. T stenting may be necessary in some situations in order to provide further treatment and additional stenting in the side branch vessel. This is typically necessitated when the disease is concentrated at the origin of the jailed vessel. This procedure is also associated with the same issues and risks previously described when stenting only one vessel and deforming the struts through the jailed vessel. In addition, since a conventional stent generally terminates at right angles to its longitudinal axis, the use of conventional stents to treat the origin of the previously jailed vessel (typically the side branch vessel) may result in blocking blood flow of the originally non-jailed vessel (typically the parent vessel) or fail to provide adequate coverage of the disease in the previously jailed vessel (typically a side branch vessel). The conventional stent might be placed proximally in order to provide full coverage around the entire circumference of the side branch, however this leads to a portion of the stent extending into the pathway of blood flow of the parent vessel. The conventional stent might alternatively be placed distally to, but not entirely overlaying the circumference of the origin of the side branch to the diseased portion. Such a position of the conventional stent results in a bifurcation that does not provide full coverage or has a gap on the proximal side (the origin of the side branch) of the vessel and is thus not completely supported. The only conceivable situation that the conventional stent, having right-angled terminal ends, could be placed where the entire circumference of the ostium is supported or treated without compromising blood flow, is where the bifurcation is formed of right angles, an uncommon occurrence. In such scenarios, extremely precise positioning of the conventional stent is required. This extremely precise positioning of the conventional stent may result with the right angled terminal end of the conventional stent overlying the entire circumference of the ostium to the diseased portion without extending into a main branch, thereby repairing the right-angled bifurcation.

To circumvent or overcome the problems and limitations associated with conventional stents in the context of repairing diseased bifurcated vessels, a stent that consistently overlays most of the diseased area of the bifurcation and provides adequate access to distal disease without subjecting the patient to any undue risks may be employed. Such a stent would have the advantage of providing adequate coverage at the proximal edge of the origin of the side branch such that a conventional stent which terminates at right angles to its longitudinal axis can be deployed in the side branch or alternate vessel without leaving a significant gap or overlap at the origin of the side branch. In addition, such a stent allows access to all portions of the bifurcated vessel should further interventional treatment be necessary.

In another prior art method for treating bifurcated vessels, commonly referred to as the "Culotte technique," the side branch vessel is first stented so that the stent protrudes into the main or parent vessel. A dilatation is then performed in the main or parent vessel to open and stretch the stent struts extending across the lumen from the side branch vessel. Thereafter, a stent is implanted in the side branch so that its proximal end overlaps with the parent vessel. One of the drawbacks of this approach is that the orientation of the stent elements protruding from the side branch vessel into the main vessel is completely random. In addition excessive metal coverage exists from overlapping strut elements in the parent vessel proximal to the carina area. Furthermore, the deployed stent must be recrossed with a wire blindly and arbitrarily selecting a stent cell. When dilating the main vessel the stent struts are randomly stretched, thereby leaving the possibility of restricted access, incomplete lumen dilatation, and major stent distortion.

In another prior art procedure, known as "kissing" stents, a stent is implanted in the main vessel with a side branch stent partially extending into the main vessel creating a double-barrelled lumen of the two stents in the main vessel proximal to the bifurcation. Another prior art approach includes a so-called "trouser legs and seat" approach, which includes implanting three stents, one stent in the side branch vessel, a second stent in the distal portion of the main vessel, and a third stent, or a proximal stent, in the main vessel just proximal to the bifurcation.

All of the foregoing stent deployment assemblies suffer from the same problems and limitations. Typically, there are uncovered surface segments or overlapped struts on the main vessel and side branch vessels between the stented segments, or there is excessive coverage in the parent vessel proximal to the bifurcation. An uncovered flap or fold in the intima or plaque will invite a "snowplow" effect, representing a substantial risk for sub-acute thrombosis, and the increased risk of the development of restenosis. Further, where portions of the stent are left unapposed within the lumen, the risk for subacute thrombosis or the development of restenosis again is increased. The prior art stents and delivery assemblies for treating bifurcations are difficult to use and deliver making successful placement challenging. Further, even where placement has been successful, the side branch vessel can be "jailed" or covered so that there is impaired access to the stented area for subsequent intervention. The present invention solves these and other problems as will be shown.

In addition to problems encountered in treating disease involving bifurcations for vessel origins, difficulty is also encountered in treating disease confined to a vessel segment but extending very close to a distal branch point or bifurcation which is not diseased and does not require treatment. In such circumstances, very precise placement of a stent covering the diseased segment, but not extending into or obstructing the side branch, may be difficult or impossible. The present invention also offers a solution to this problem.

The stent of the present invention includes struts that make up the rings and links, the struts having either uniform cross-sections, or cross-sections having various widths and thicknesses.

SUMMARY OF THE INVENTION

The invention provides for improved stent designs and stent delivery catheter assemblies for repairing a main vessel and side branch-vessel forming a bifurcation, without compromising blood flow, thereby allowing access to all portions of the bifurcated vessels should further interventional treatment be necessary. The present invention includes a stent pattern having one or more portals, various stent lengths and portal locations, a stent delivery catheter assembly, radiopaque marker patterns on the stent and/or catheter delivery system, and a method for delivering and implanting the stent in a bifurcated vessel.

The Stent Pattern

The stent of the present invention includes a cylindrical body having rings aligned along a longitudinal axis, where each ring has a delivered diameter in which it is crimped or compressed tightly onto the balloon catheter and an implanted diameter where the stent is implanted in a bifurcated vessel.

The present invention is directed to an intravascular stent that has a pattern or configuration that permits the stent to be tightly compressed or crimped onto a catheter to provide an extremely low profile and to prevent relative movement between the stent and the catheter. The stent also is highly flexible along its longitudinal axis to facilitate delivery through tortuous body lumens, but which is stiff and stable enough radially in its expanded condition to maintain the patency of a body lumen such as an artery when the stent is implanted therein.

The stent of the present invention generally includes a plurality of cylindrical rings that are interconnected to form the stent. The stent typically is mounted on a balloon catheter if it is balloon expandable or mounted on or in a catheter without a balloon if it is self-expanding.

In one embodiment, each of the cylindrical rings making up the stent has a proximal end and a distal end and a cylindrical plane defined by a cylindrical outer wall surface that extends circumferentially between the proximal end and the distal end of the cylindrical ring. Generally, the cylindrical rings have a serpentine or undulating shape which includes at least one U-shaped element, and typically each ring has more than one U-shaped element. The cylindrical rings are interconnected by at least one connecting link which attaches one cylindrical ring to an adjacent cylindrical ring. The undulating links are highly flexible and allow the stent to be highly flexible along the stent longitudinal axis. The undulating links have a curved portion that extends transverse to the stent longitudinal axis. More specifically, the curved portion extends in a transverse direction (or circumferentially) such that it would intersect with the adjacent U-shaped element, however, the adjacent U-shaped element is shorter in length than other U-shaped elements in the same ring. Thus, when the stent is compressed or crimped onto the catheter, the undulating portion of the links does not overlap or intersect with the adjacent U-shaped element since that element is shorter in length than other U-shaped elements in the same ring. With this structure, the stent can be compressed or crimped to a much tighter or smaller diameter onto the catheter, which permits low profile delivery as well as tight crimping force on the catheter to reduce the likelihood of movement between the stent and the catheter during delivery and prior to implanting the stent in the vessel. In one aspect of the invention, the portal region is formed between two adjacent cylindrical rings and is configured to receive a side branch balloon of a balloon catheter. In this embodiment, a first balloon of a balloon catheter extends through the main body of the stent, and a second balloon extends through the portal area so that the two balloons are substantially side by side. The two balloons can be of different lengths and diameters with the first balloon being longer than the second balloon. In this embodiment, three undulating links connect adjacent cylindrical rings. The undulating portion or bend in two of the links of the portal region face in opposite directions transverse to the longitudinal axis of the stent. The undulating links connecting cylindrical rings in the main body of the stent have undulating portions or bends that all point in the same direction transverse to the longitudinal axis of the stent. In another embodiment, at least one of the main body cylindrical rings is connected by three undulating links, where the undulating portion or bend of one of the links points in a direction opposite to that of the other two undulating portions or bends, however, all of the undulating portions or bends are positioned transverse to the longitudinal axis of the stent. In this embodiment, the width of the bar arms of the proximal end ring have a first width, other rings have a second width, and certain bar arms in the portal region rings have a third width. Varying the width of the bar arms varies the flexibility of the stent in particular regions.

In one embodiment, each of the cylindrical rings making up the stent has a proximal end and a distal end and cylindrical plane defined by a cylindrical outer wall surface that extends circumferentially between the proximal end and the distal end of the cylindrical ring. Generally, the cylindrical rings have a serpentine or undulating shape which includes at least one U-shaped element, and typically each ring has more than one U-shaped element. The cylindrical rings are interconnected by at least one connecting link which attaches one cylindrical ring to an adjacent cylindrical ring. The undulating links are highly flexible and allow the stent to be highly flexible along the stent longitudinal axis. The undulating links have a curved portion that extends transverse to the stent longitudinal axis. More specifically, the curved portion extends in a transverse direction (or circumferentially) such that it would intersect with the adjacent U-shaped element, however, the adjacent U-shaped element is shorter in length than other U-shaped elements in the same ring. Thus, when the stent is compressed or crimped onto the catheter, the undulating portion of the links does not overlap or intersect with the adjacent U-shaped element since that element is shorter in length than other U-shaped elements in the same ring. With this structure, the stent can be compressed or crimped to a much tighter or smaller diameter onto the catheter, which permits low profile delivery as well as tight crimping force on the catheter to reduce the likelihood of movement between the stent and the catheter during delivery and prior to implanting the stent in the vessel. In one aspect of the invention, the portal region is formed between two adjacent cylindrical rings and is configured to receive a side branch balloon of a balloon catheter. In this embodiment, a first balloon of a balloon catheter extends through the main body of the stent, and a second balloon extends through the portal area so that the two balloons are substantially side by side, with the first balloon being longer than the second balloon. In one aspect of the invention, three undulating links connect adjacent cylindrical rings except for the portal region, in which two undulating links connect the ring in the portal region with the adjacent ring of the main body of the stent. Further, the undulating portion or bend in the two links of the portal region face in opposite directions transverse to the longitudinal axis of the stent. The undulating links connecting cylindrical rings in the main body of the stent have undulating portions or bends that all point in the same direction transverse to the longitudinal axis of the stent. In another embodiment, at least one of the main body cylindrical rings is connected by three undulating links, where the undulating portion or bend of one of the links points in a direction opposite to that of the other two undulating portions or bends, however, all of the undulating portions or bends are positioned transverse to the longitudinal axis of the stent. In another embodiment, a distal section of the stent has a plurality of cylindrical rings attached by undulating links as previously described. A central section, includes the portal region, which is attached to a proximal section of the stent by two undulating links, the undulating portion of which points in opposite directions transverse to the longitudinal axis of the stent. A proximal section of the stent includes plurality of cylindrical rings, at least one of which has a different pattern of U-shaped elements than the other cylindrical rings in the proximal section. More specifically, a proximal end ring includes U-shaped elements having a configuration different than the U-shaped elements of the other cylindrical rings in the proximal section, and the U-shaped elements of the proximal end ring are substantially identical.

In one embodiment, each of the cylindrical rings making up the stent has a proximal end and a distal end and cylindrical plane defined by a cylindrical outer wall surface that extends circumferentially between the proximal end and the distal end of the cylindrical ring. Generally, the cylindrical rings have a serpentine or undulating shape which includes at least one U-shaped element, and typically each ring has more than one U-shaped element. The cylindrical rings are interconnected by at least one connecting link which attaches one cylindrical ring to an adjacent cylindrical ring. The undulating links are highly flexible and allow the stent to be highly flexible along the stent longitudinal axis. The undulating links have a curved portion that extends transverse to the stent longitudinal axis. More specifically, the curved portion extends in a transverse direction (or circumferentially) such that it would intersect with the adjacent U-shaped element, however, the adjacent U-shaped element is shorter in length than other U-shaped elements in the same ring. Thus, when the stent is compressed or crimped onto the catheter, the undulating portion of the links does not overlap or intersect with the adjacent U-shaped element since that element is shorter in length than other U-shaped elements in the same ring. With this structure, the stent can be compressed or crimped to a much tighter or smaller diameter onto the catheter, which permits low profile delivery as well as tight crimping force on the catheter to reduce the likelihood of movement between the stent and the catheter during delivery and prior to implanting the stent in the vessel. In one aspect of the invention, the portal region is formed between two adjacent cylindrical rings and is configured to receive a side branch balloon of a balloon catheter. In this embodiment, a first balloon of a balloon catheter extends through the main body of the stent, and a second balloon extends through the portal area so that the two balloons are substantially side by side, with the first balloon being longer than the second balloon. In one aspect of the invention, three undulating links connect adjacent cylindrical rings except for the portal region, in which two undulating links connect the ring in the portal region with the adjacent ring of the main body of the stent. Further, the undulating portion or bend in the two links of the portal region face in opposite directions transverse to the longitudinal axis of the stent. The undulating links connecting cylindrical rings in the main body of the stent have undulating portions or bends that all point in the same direction transverse to the longitudinal axis of the stent. In another embodiment, at least one of the main body cylindrical rings are connected by three undulating links, where the undulating portion or bend of one of the links points in a direction opposite to that of the other two undulating portions or bends, however, all of the undulating portions or bends are positioned transverse to the longitudinal axis of the stent. In this embodiment, the stent includes thirteen cylindrical rings, the proximal ring being designated ring No. 1, the portal cylindrical ring being designated No. 6, and the distal end ring being designated ring No. 13. Referring to portal ring No. 6, two undulating links connect portal ring No. 6 to distal section cylindrical ring No. 7. The undulating portions of the two undulating links point in opposite directions, both being transverse to the longitudinal axis of the stent. In this embodiment, the undulating portions of the two links point toward the portal region, which allows the adjacent U-shaped elements that are outside the portal region to have a length longer than the adjacent U-shaped elements inside the portal region. This allows the bar arms on the longer U-shaped elements to expand more when the stent is expanded and implanted in a bifurcated artery, and it will reduce ring separation in the side branch. In another embodiment, the proximal end ring is attached to the adjacent cylindrical ring by two undulating connecting links. This provides additional flexibility at the proximal end and also reduces the likelihood of strut flaring during delivery and expansion of the stent.

In one embodiment, each of the cylindrical rings making up the stent has a proximal end and a distal end and cylindrical plane defined by a cylindrical outer wall surface that extends circumferentially between the proximal end and the distal end of the cylindrical ring. Generally, the cylindrical rings have a serpentine or undulating shape which includes at least one U-shaped element, and typically each ring has more than one U-shaped element. The cylindrical rings are interconnected by at least one connecting link which attaches one cylindrical ring to an adjacent cylindrical ring. The undulating links are highly flexible and allow the stent to be highly flexible along the stent longitudinal axis. The undulating links have a curved portion that extends transverse to the stent longitudinal axis. More specifically, the curved portion extends in a transverse direction (or circumferentially) such that it would intersect with the adjacent U-shaped element, however, the adjacent U-shaped element is shorter in length than other U-shaped elements in the same ring. Thus, when the stent is compressed or crimped onto the catheter, the undulating portion of the links do not overlap or intersect with the adjacent U-shaped element since that element is shorter in length than other U-shaped elements in the same ring. With this structure, the stent can be compressed or crimped to a much tighter or smaller diameter onto the catheter, which permits low profile delivery as well as tight crimping force on the catheter to reduce the likelihood of movement between the stent and the catheter during delivery and prior to implanting the stent in the vessel. In one aspect of the invention, the portal region is formed between two adjacent cylindrical rings and is configured to receive a side branch balloon of a balloon catheter. In this embodiment, a first balloon of a balloon catheter extends through the main body of the stent, and a second balloon extends through the portal area so that the two balloons are substantially side by side, with the first balloon being longer than the second balloon. In one aspect of the invention, three undulating links connect adjacent cylindrical rings except for the portal region, in which two undulating links connect the ring in the portal region with the adjacent ring of the main body of the stent. Further, the undulating portion or bend in the two links of the portal region face in opposite directions transverse to the longitudinal axis of the stent. The undulating links connecting cylindrical rings in the main body of the stent have undulating portions or bends that all point in the same direction transverse to the longitudinal axis of the stent. In another embodiment, at least one of the main body cylindrical rings are connected by three undulating links, where the undulating portion or bend of one of the links points in a direction opposite to that of the other two undulating portions or bends, however, all of the undulating portions or bends are positioned transverse to the longitudinal axis of the stent. In this embodiment, the portal area or portal region is configured to be symmetrical about the longitudinal axis of the stent to ensure even expansion. This axis is centered within the portal. All of the cylindrical rings, except the portal ring (the sixth ring from the proximal end of the stent) and the ring proximal to it, have six crests or peaks connected by three undulating links. The cylindrical rings in the proximal section have a larger expansion diameter than the cylindrical rings in the distal section to accommodate any post-dilatation using a kissing balloon technique. In this embodiment, the portal cylindrical ring and the cylindrical ring proximal to the portal cylindrical ring are configured to have eight crests or peaks per ring and are connected to each other by three undulating links. The portal ring and the cylindrical ring proximal to the portal ring are in phase. In one aspect of this embodiment, the proximal end ring has wider struts or bar arms, shorter bar arms or struts than other cylindrical rings of the stent, and all of the peaks or crests have a keyhole design in order to reduce flaring at the proximal end of the stent. The wider struts or bar arms increase the radial strength of the proximal end ring, thereby making it more difficult for the ring to lift or flare during delivery or expansion of the stent. The keyhole crests or peaks, when crimped, will provide more grip on the balloon. The shorter bar arms or struts make it difficult for them to open and flare because of a shorter lever arm. All of these factors, working together, reduce flaring of the proximal end ring.

In one embodiment, each of the cylindrical rings making up the stent has a proximal end and a distal end and cylindrical plane defined by a cylindrical outer wall surface that extends circumferentially between the proximal end and the distal end of the cylindrical ring. Generally, the cylindrical rings have a serpentine or undulating shape which includes at least one U-shaped element, and typically each ring has more than one U-shaped element. The cylindrical rings are interconnected by at least one connecting link which attaches one cylindrical ring to an adjacent cylindrical ring. The undulating links are highly flexible and allow the stent to be highly flexible along the stent longitudinal axis. The undulating links have a curved portion that extends transverse to the stent longitudinal axis. More specifically, the curved portion extends in a transverse direction (or circumferentially) such that it would intersect with the adjacent U-shaped element, however, the adjacent U-shaped element is shorter in length than other U-shaped elements in the same ring. Thus, when the stent is compressed or crimped onto the catheter, the undulating portion of the links do not overlap or intersect with the adjacent U-shaped element since that element is shorter in length than other U-shaped elements in the same ring. With this structure, the stent can be compressed or crimped to a much tighter or smaller diameter onto the catheter, which permits low profile delivery as well as tight crimping force on the catheter to reduce the likelihood of movement between the stent and the catheter during delivery and prior to implanting the stent in the vessel. In one aspect of the invention, the portal region is formed between two adjacent cylindrical rings and is configured to receive a side branch balloon of a balloon catheter. In this embodiment, a first balloon of a balloon catheter extends through the main body of the stent, and a second balloon extends through the portal area so that the two balloons are substantially side by side, with the first balloon being longer than the second balloon.

In this embodiment, the stent comprises three sections, a proximal section, a portal section, and a distal section. Rings 1 to 4 in the proximal section all are oriented opposite to or out of phase with rings 7-12 in the distal section. This allows the W-shaped portions of the rings in the proximal section to be tailored to allow a smooth guide pull-back when delivering the stent. In one aspect of the invention, the undulating links between rings 4 and 5 are substantially longer than the undulating links connecting all of the other rings since the W-shaped portions and U-shaped portions in ring 4 are out of phase with the W-shaped portions and U-shaped portions in ring 5. The longer links allow the fourth and fifth rings to extend further into the side branch vessel when the stent is expanded and implanted in the bifurcated vessel. In another embodiment, at least two of the links connecting the fourth and fifth rings are linear, thereby insuring that the distance between the two rings stays constant throughout delivery and when the portal region is expanded toward the side branch vessel. In another embodiment, at least some of the U-shaped portions in the fourth and fifth rings have substantially longer bar arms in order to provide more coverage as that portion of the rings expand into the opening to the side branch vessel.

In one embodiment, each of the cylindrical rings making up the stent has a proximal end and a distal end and cylindrical plane defined by a cylindrical outer wall surface that extends circumferentially between the proximal end and the distal end of the cylindrical ring. Generally, the cylindrical rings have a serpentine or undulating shape which includes at least one U-shaped element, and typically each ring has more than one U-shaped element. The cylindrical rings are interconnected by at least one connecting link which attaches one cylindrical ring to an adjacent cylindrical ring. The undulating links are highly flexible and allow the stent to be highly flexible along the stent longitudinal axis. The undulating links have a curved portion that extends transverse to the stent longitudinal axis. More specifically, the curved portion extends in a transverse direction (or circumferentially) such that it would intersect with the adjacent U-shaped element, however, the adjacent U-shaped element is shorter in length than other U-shaped elements in the same ring. Thus, when the stent is compressed or crimped onto the catheter, the undulating portion of the links do not overlap or intersect with the adjacent U-shaped element since that element is shorter in length than other U-shaped elements in the same ring. With this structure, the stent can be compressed or crimped to a much tighter or smaller diameter onto the catheter, which permits low profile delivery as well as tight crimping force on the catheter to reduce the likelihood of movement between the stent and the catheter during delivery and prior to implanting the stent in the vessel. In one aspect of the invention, the portal region is formed between two adjacent cylindrical rings and is configured to receive a side branch balloon of a balloon catheter. In this embodiment, a first balloon of a balloon catheter extends through the main body of the stent, and a second balloon extends through the portal area so that the two balloons are substantially side by side, with the first balloon being longer than the second balloon. After deployment of the bifurcated stent into the main vessel, with the portal region stenting the vessel wall opposite the carina of the bifurcation, a second stent can be implanted in the side branch vessel, so that the proximal end of the second stent abuts the struts of the portal region. In this embodiment, a proximal radiopaque marker is positioned on the proximal end of the bifurcated stent and a radiopaque marker on the shaft of the delivery catheter for the second (side branch) stent aligns with the radiopaque mark on the proximal end of the bifurcated stent. The distance between the radiopaque marker on the delivery catheter and the proximal end of the second stent substantially equals the distance between the proximal radiopaque marker on the bifurcated stent and the distal end of the portal region or portal cylindrical ring. Thus, the second stent can be deployed in the side branch vessel so that the proximal end of the second stent abuts the portal cylindrical ring. In another embodiment, two radiopaque markers are placed on the proximal end of the bifurcated stent so that as the delivery catheter advances the second stent into the side branch vessel, the radiopaque marker on the delivery catheter will come into alignment between the two radiopaque markers on the proximal end of the bifurcated stent. The two radiopaque markers should be approximately 180° apart. When the two radiopaque markers on the proximal end of the bifurcated stent come into alignment with the radiopaque marker on the shaft of the catheter delivering the second stent (side branch stent), the proximal end of the second stent will be aligned with the distal end of the portal ring on the bifurcated stent. In another embodiment, one or two radiopaque markers are positioned on the distal end of the portal cylindrical ring which has flared and covers the carina to the bifurcated vessel. As the delivery catheter advances the second stent into the side branch vessel, a radiopaque marker on the delivery catheter, which has been positioned to align with the proximal end of the second stent, comes into alignment with the one or two radiopaque markers on the distal end of the portal cylindrical ring. Once the radiopaque markers on the portal end of the bifurcated stent and the catheter are aligned, the second or side branch stent can be deployed so that the proximal end of the second stent abuts the distal end of the portal ring.

In another embodiment, one or two radiopaque markers are positioned on the distal end of the portal cylindrical ring which has flared and covers the carina to the bifurcated vessel. As the delivery catheter advances the second stent into the side branch vessel, a radiopaque marker on the proximal edge of the second stent comes into alignment with the one or two radiopaque markers on the distal end of the portal cylindrical ring. Once the radiopaque markers on the portal end of the bifurcated stent and the proximal end of the second stent are aligned, the second or side branch stent can be deployed so that the proximal end of the second stent abuts the distal end of the portal ring.

In one embodiment, each of the cylindrical rings making up the stent has a proximal end and a distal end and cylindrical plane defined by a cylindrical outer wall surface that extends circumferentially between the proximal end and the distal end of the cylindrical ring. Generally, the cylindrical rings have a serpentine or undulating shape which includes at least one U-shaped element, and typically each ring has more than one U-shaped element. The cylindrical rings are interconnected by at least one connecting link which attaches one cylindrical ring to an adjacent cylindrical ring. The undulating links are highly flexible and allow the stent to be highly flexible along the stent longitudinal axis. The undulating links have a curved portion that extends transverse to the stent longitudinal axis. More specifically, the curved portion extends in a transverse direction (or circumferentially) such that it would intersect with the adjacent U-shaped element, however, the adjacent U-shaped element is shorter in length than other U-shaped elements in the same ring. Thus, when the stent is compressed or crimped onto the catheter, the undulating portion of the links do not overlap or intersect with the adjacent U-shaped element since that element is shorter in length than other U-shaped elements in the same ring. With this structure, the stent can be compressed or crimped to a much tighter or smaller diameter onto the catheter, which permits low profile delivery as well as tight crimping force on the catheter to reduce the likelihood of movement between the stent and the catheter during delivery and prior to implanting the stent in the vessel. In one aspect of the invention, the portal region is formed between two adjacent cylindrical rings and is configured to receive a side branch balloon of a balloon catheter. In this embodiment, a first balloon of a balloon catheter extends through the main body of the stent, and a second balloon extends through the portal area so that the two balloons are substantially side by side, with the first balloon being longer than the second balloon. In addition to, or in lieu of, the portal region in approximately the central portion of the stent, a proximal portal region, a central portal region, and/or a distal portal region are provided in a bifurcated stent. In this embodiment, the proximal portal region is positioned between cylindrical rings No. 2 and 3 (with the proximal end ring being ring No. 1 and the distal end ring being ring No. 13), the central portal region is positioned between cylindrical rings No. 8 and 9, and the distal portal region is positioned between cylindrical rings No. 12 and 13. Each of the portals can be identified under fluoroscopy by adding radiopaque material to the undulating links surrounding the portal area.

In one embodiment, each of the cylindrical rings making up the stent has a proximal end and a distal end and cylindrical plane defined by a cylindrical outer wall surface that extends circumferentially between the proximal end and the distal end of the cylindrical ring. Generally, the cylindrical rings have a serpentine or undulating shape which includes at least one U-shaped element, and typically each ring has more than one U-shaped element. The cylindrical rings are interconnected by at least one connecting link which attaches one cylindrical ring to an adjacent cylindrical ring. The undulating links are highly flexible and allow the stent to be highly flexible along the stent longitudinal axis. The undulating links have a curved portion that extends transverse to the stent longitudinal axis. More specifically, the curved portion extends in a transverse direction (or circumferentially) such that it would intersect with the adjacent U-shaped element, however, the adjacent U-shaped element is shorter in length than other U-shaped elements in the same ring. Thus, when the stent is compressed or crimped onto the catheter, the undulating portion of the links do not overlap or intersect with the adjacent U-shaped element since that element is shorter in length than other U-shaped elements in the same ring. With this structure, the stent can be compressed or crimped to a much tighter or smaller diameter onto the catheter, which permits low profile delivery as well as tight crimping force on the catheter to reduce the likelihood of movement between the stent and the catheter during delivery and prior to implanting the stent in the vessel. In one aspect of the invention, the portal region is formed between two adjacent cylindrical rings and is configured to receive a side branch balloon of a balloon catheter. In this embodiment, a first balloon of a balloon catheter extends through the main body of the stent, and a second balloon extends through the portal area so that the two balloons are substantially side by side, with the first balloon being longer than the second balloon. In order to identify the portal region under fluoroscopy, a polymer radiopaque coating covers the stent struts so that the physician can more accurately locate and position the side branch balloon relative to the side branch vessel. In one embodiment, approximately sixty percent or more of tungsten is loaded into a polymer which is then coated onto individual stent struts around the portal region of the stent in order to provide a radiopaque marker for the physician. The polymer must be flexible enough to expand when the stent expands and so that it does not adversely affect the coating integrity. In one embodiment, the radiopaque marker polymer is coated onto only straight portions of the struts so that expansion of the stent will not cause the polymer to dislodge.

In one embodiment, each of the cylindrical rings making up the stent has a proximal end and a distal end and a cylindrical plane defined by a cylindrical outer wall surface that extends circumferentially between the proximal end and the distal end of the cylindrical ring. Generally, the cylindrical rings have a serpentine or undulating shape which includes at least one U-shaped element, and typically each ring has more than one U-shaped element. The cylindrical rings are interconnected by at least one undulating link which attaches one cylindrical ring to an adjacent cylindrical ring. The undulating links are highly flexible and allow the stent to be highly flexible along the stent longitudinal axis. At least some of the undulating links have a curved portion that extends transverse to the stent longitudinal axis for a predetermined distance that coincides with one of the U-shaped elements. More specifically, the curved portion extends in a transverse direction (or circumferentially) such that it would intersect with the corresponding U-shaped element, however, the corresponding U-shaped element is shorter in length than other U-shaped elements in the same ring. Thus, when the stent is compressed or crimped onto the catheter, the curved portions do not overlap or intersect with the adjacent U-shaped element since that element is shorter in length than similar U-shaped elements in the particular ring. In this manner, the stent can be compressed or crimped to a much tighter or smaller diameter onto the catheter which permits low profile delivery as well as a tight gripping force on the catheter to reduce the likelihood of movement between the stent and the catheter during delivery and prior to implanting the stent in the vessel. In one embodiment, the links have an undulation or bend. The undulating links can include bends connected by substantially straight portions wherein the substantially straight portions are substantially perpendicular to the stent longitudinal axis. The undulating links are connected to one ring by a straight portion and to an adjacent ring by a curved portion.

Not only do the undulating links that interconnect the cylindrical rings provide flexibility to the stent, but the number of links and the positioning of the links also enhances the flexibility by allowing uniform flexibility when the stent is bent in any direction along its longitudinal axis. Uniform flexibility along the stent derives in part from the links of one ring being circumferentially offset from the links in an adjacent ring. Further, the cylindrical rings are configured to provide flexibility to the stent in that portions of the rings can flex or bend and tip outwardly as the stent is delivered through a tortuous vessel.

In one embodiment, the cylindrical rings are formed of a plurality of peaks and valleys, where the valleys of one cylindrical ring are circumferentially offset from the valleys of an adjacent cylindrical ring. In this configuration, at least one undulating link attaches each cylindrical ring to an adjacent cylindrical ring so that at least a portion of the undulating link is positioned within one of the valleys and it attaches the valley to an adjacent peak.

While the cylindrical rings and undulating links generally are not separate structures, they have been conveniently referred to as rings and links for ease of identification. Further, the cylindrical rings can be thought of as comprising a series of U's, W's and Y-shaped structures in a repeating pattern. Again, while the cylindrical rings are not divided up or segmented into U's, W's and Y's, the pattern of the cylindrical rings resemble such configuration. The U's, W's and Y's promote flexibility in the stent primarily by flexing and by tipping radially outwardly as the stent is delivered through a tortuous vessel.

The undulating links are positioned so that the curved portion of the link is outside the W-shaped portion. Since the curved portion does not substantially expand (if at all) when the stent is expanded, it will continue to provide good vessel wall coverage even as the curved part of the W-shaped portion spreads apart as the stent is expanded. The curved portion of the link extends in a direction transverse to the stent longitudinal axis for a distance that positions it adjacent and proximal to the peak of a U-shaped element. These U-shaped elements have struts that are shorter than the struts of the other U-shaped elements in the same cylindrical ring so that as the stent is compressed the curved portion of the link does not overlap the adjacent U-shaped element.

The number and location of undulating links that interconnect adjacent cylindrical rings can be varied as the application requires. Since the undulating links typically do not expand when the cylindrical rings of the stent expand radially outwardly, the links are free to continue to provide flexibility and also to provide a scaffolding function to assist in holding open the artery. The addition or removal of the undulating links has very little impact on the overall longitudinal flexibility of the stent. Each undulating link is configured so that it promotes longitudinal flexibility whereas some prior art connectors significantly reduce longitudinal flexibility of the stent.

The cylindrical rings of the stent are plastically deformed when expanded when the stent is made from a metal that is balloon expandable. Typically, the balloon-expandable stent is made from a stainless steel alloy, cobalt chromium, tungsten, polymers, or similar material.

Similarly, the cylindrical rings of the stent expand radially outwardly when the stent is formed from superelastic alloys, such as nickel-titanium (NiTi) alloys. In the case of superelastic alloys, the stent expands upon application of a temperature change or when a stress is relieved, as in the case of a pseudoelastic phase change.

Further, because of the positioning of the links, and the fact that the links do not expand or stretch when the stent is radially expanded, the overall length of the stent is substantially the same in the unexpanded and expanded configurations. In other words, the stent will not substantially shorten upon expansion.

The stent may be formed from a tube by laser cutting the pattern of cylindrical rings and undulating links in the tube. The stent also may be formed by laser cutting a flat metal sheet in the pattern of the cylindrical rings and links, and then rolling the pattern into the shape of the tubular stent and providing a longitudinal weld to form the stent.

The stent of the present invention includes struts that make up the rings and links, the struts having either uniform cross-sections, or cross-sections having various widths and radial thicknesses.

The Stent Delivery Catheter

The present invention also includes a stent delivery catheter assembly for repairing bifurcated vessels including an elongated catheter body which has a proximal catheter shaft, an intermediate section or mid-section, and a distal section. The catheter assembly contains an over-the-wire (OTW) guide wire lumen extending from the proximal catheter hub to one of the distal tips of the distal end of the catheter. The catheter assembly also includes a rapid exchange (Rx) guide wire lumen which extends from the proximal end of the mid-section to one of the distal tips of the distal end of the catheter. The proximal catheter shaft also contains an inflation lumen which extends from the proximal hub of the proximal catheter shaft to the mid-section of the catheter and is in fluid communication with the inflation lumen contained within the mid-section. The mid-section contains lumens for both the OTW and the Rx guide wire lumen. The Rx guide wire lumen begins at about the proximal section of the intermediate shaft and extends to one of the distal tips of the distal catheter shaft. In an alternative embodiment, the Rx guidewire lumen is replaced by a fixed wire design having a fixed guidewire with a distal section permanently secured to a distal section of the catheter branch. The OTW guide wire lumen extends through the intermediate section of the catheter and extends proximally to the catheter hub connected to the proximal catheter shaft and extends distally to one of the tips of the distal section of the catheter. The distal section of the catheter consists of two shafts extending from the distal end of the mid-shaft to the distal end of the catheter tips. Each shaft has a balloon connected adjacent the distal end followed by a tip connected to the distal end of the balloon. Each shaft contains a guide wire lumen and an inflation lumen. The inflation lumen of each shaft is in fluid communication with the inflation lumen of the mid-shaft. One of the shafts of the distal section contains an Rx guide wire lumen, which extends proximally through the mid-section of the catheter and exits at about the proximal end of the mid-section of the catheter, the Rx guide wire lumen also extends distally to one of the tips of the distal section of the catheter. The other shaft of the distal section contains an OTW guide wire lumen, which extends proximally through the mid-section and proximal section of the catheter and exits at the proximal hub connected to the distal end of the proximal catheter section, the OTW guide wire lumen also extends distally to one of the tips of the distal section of the catheter. The distal section of the catheter includes two balloons. One balloon is longer and is connected to one of the shafts of the distal catheter section. The long balloon is connected to the catheter shaft such that the inflation lumen of the shaft is in fluid communication with the balloon and the guide wire lumen contained within the shaft extends through the center of the balloon. The proximal section of the balloon is sealed to the distal end of the shaft and the distal end of the balloon is sealed around the outside of the guide wire lumen or inner member running through the center of the balloon. The proximal and distal seals of the balloon allow for fluid pressurization and balloon inflation from the proximal hub of the catheter. The short balloon is connected in the same manner as the long balloon described above to the alternate shaft of the distal section of the catheter. Each balloon has a tip extending from their distal ends. The tips are extensions of the inner members extending through the center of the balloon and contain a lumen for a guide wire associated with each guide wire lumen. The distal end of the catheter has two tips associated with their respective balloons and the guide wire lumen or inner member. One tip is longer and contains a coupler utilized for joining the tips during delivery of the previously described stent.

The stent of the present invention is crimped or compressed onto the long balloon and the short balloon such that the long balloon extends through the distal opening and the proximal opening in the stent, while the short balloon extends through the proximal opening and the central opening of the stent.

In one embodiment, a balloon catheter of the invention has one or more polymeric radiopaque markers, and generally comprises an elongated catheter shaft having a branched distal section with a first and a second branch configured for releasably coupling together to form a coupled configuration, an inflation lumen, and a joining wire lumen extending at least within the first branch of the branched distal section; a first balloon on the first branch with an inflatable interior in fluid communication with the inflation lumen, and a second balloon on the second branch with an inflatable interior in fluid communication with the inflation lumen. In a presently preferred embodiment, the polymeric radiopaque marker provides for visualizing a distal end section of the branch of the catheter shaft configured for placement in the side branch of the patient's vessel (e.g., the catheter branch which has the short balloon thereon), to facilitate accurately positioning the catheter and stent thereon prior to unjoining the two distal tips of the catheter. The polymeric radiopaque marker is a blend of polymeric and radiopaque materials, which provides a highly bright (under fluoroscopy) yet flexible marker. As a result, the soft flexible marker does not create a large stiffness transition disadvantageously affecting the catheter's ability to be maneuvered to a desired location within the patient's tortuous anatomy. The polymeric radiopaque tip marker is preferably secured to the shaft such that it provides a smooth transition in stiffness at the catheter distal tip which improves the overall deliverability of the stent delivery catheter. In a presently preferred embodiment, the marker is a ring on or in a distal end section of the shaft. However, a variety of suitable configurations can be used including an embodiment in which the polymeric radiopaque marker comprises a distal tip member defining the distal end of the lumen of the catheter branch.

Additionally, the polymeric radiopaque side branch tip marker facilitates determining and correcting the rotational orientation of the catheter relative to the opening of the side branch vessel. As the catheter assembly is advanced through tortuous coronary arteries, over the Rx guide wire, the central opening of the stent may or may not always be perfectly aligned with the side branch take-off (i.e., the opening to the side branch vessel). If the central opening of the stent is in alignment with the side branch take-off it is said to be "in phase" and represents the ideal position for stenting the main branch vessel and the opening to the side branch vessel. When the central opening of the stent and the side branch take-off are not aligned it is said to be "out of phase" and depending upon how many degrees out of phase, the stent may require repositioning or reorienting so that the central opening more closely coincides with the side branch take-off. The polymeric radiopaque tip marker provides for visualization of the position of the side branch distal tip of the catheter, with the two distal tips of the catheter in the joined or the unjoined configuration and without disadvantageously increasing the stiffness of the catheter distal end, and thereby facilitates aligning the catheter to put it "in phase".

In a presently preferred embodiment, the polymeric radiopaque tip marker is formed of a polymeric blend having a high weight percent loading of radiopaque material, as described in U.S. patent application Ser. No. 10/945,637, incorporated by reference herein in its entirety. The polymeric blend provides a highly radiopaque and yet highly flexible marker. In one embodiment, the fill ratio is about 90.8 weight percent (34.9 volume percent) to about 93.2 weight percent (42.7 volume percent) of radiopaque material. However, in an alternative embodiment, a smaller amount of radiopaque material is used to optimize the flexibility of the marker or decrease the image intensity under fluoroscopy. Thus, the fill ratio is preferably selected to balance the flexibility and radiopacity of the distal tip marker.

The marker relies on the use of radiopaque materials with a preselected particle shape and a preselected particle size distribution as well as the inclusion of one or more additives in the polymer/radiopaque agent blend, as discussed in the Ser. No. 10/945,637 application, incorporated by reference above. A multifunctional polymeric additive is added to the composition in order to enhance the wetting, adhesive and flow properties of the individual radiopaque particles by the polymer so as to cause each particle to be encapsulated by the polymer and thereby allow the polymer to form a continuous binder. An antioxidant may optionally be added in order to preserve the high molecular weight of the polymer matrix as it is exposed to the high temperatures and shear stresses associated with the compounding and extrusion processes.

In a presently preferred embodiment, the polymeric radiopaque blend is formed of a blend of a polyether block amide (PEBAX) polymer and radiopaque tungsten particles. However, a variety of suitable polymers and radiopaque materials may be used for the polymeric radiopaque blend. The PEBAX polymeric material provides a soft, flexible marker that is compatible with the presently preferred materials (e.g., polyamides such as PEBAX) used to form a distal tip of the stent delivery catheter of the invention, so that the polymeric radiopaque tip marker can be melt/fusion bonded to the catheter shaft without the use of adhesives. The polymeric blend can be extruded to form the desired shape of the marker.

In a presently preferred embodiment, the polymeric blend provides a marker which appears visually different under fluoroscopy from the catheter's balloon radiopaque markers (e.g., the radiopaque marker bands which indicate the working length of the balloon and/or the alignment of the stent on the balloon). For example, in one embodiment, the balloon radiopaque marker(s) comprise a metal (e.g., Pt/Ir) band which thus has a different composition than the polymeric radiopaque blend and which appears as a sharply defined rectangular band under fluoroscopy, whereas the polymeric radiopaque tip marker appears as a rounded, less sharply defined image. Additionally, in one embodiment, the length of the polymeric radiopaque tip marker is different than (e.g., longer than) the balloon radiopaque marker(s).

In one embodiment, the bifurcated distal section of the catheter has at least one secured portion along which the first and second branches of the distal shaft section are permanently secured together. The secured portion is located proximal to the inflatable section of the balloons, and preferably distal to the proximal end of the branched distal shaft section (and distal to the intermediate section of the shaft) so that the branched distal shaft section has an unsecured portion which is proximally adjacent to the secured portion. In a presently preferred embodiment, the two shafts are permanently secured together at least in part by a tubular outer band member such as, for example, a length of heat shrink tubing. A first band member is preferably located adjacent to the proximal-most balloon end, and a second band member is preferably located proximal thereto. For example, in a presently preferred embodiment, the second band member is located at about the half-way point along the length of the distal shaft section between the proximal end of the balloons and the distal end of the intermediate shaft section. Adhesive may additionally or alternatively be used to join the branches together. The secured distal branches of the catheter provide improved deliverability by preventing or inhibiting the tendency of the two outer members of the distal shafts to separate during advancement of the catheter within the patient's tortuous anatomy. As a result, the catheter has the deliverability and manufacturability advantages provided by the two shafts extending separately from the intermediate shaft section, in combination with the deliverability advantages provided by securing the two shafts together at one or more location between the balloons and the intermediate shaft section. Additionally, the secured distal shafts of the catheter prevent or inhibit damage to the vessel wall which can otherwise occur if the end of the stent is caused to become flared. Such flaring at the end of the stent can occur as the proximal ends of the balloons move a disadvantageously large amount relative to one another during delivery and deployment of the stent.

A joining wire slidably disposed within a branch (typically the OTW branch) of the catheter releaseably joins the distal tips of the two branches of the catheter together for advancement within the patient's anatomy. The joining wire is locked to the proximal end of the catheter assembly to keep the two distal tips together during delivery to ensure that the stent remains securely mounted on the balloons. With the stent in position for deployment within the body lumen, the joining wire is at least partially retracted to release the two branch tips. However, the ability to advance the joining wire within the branch vessel and use the joining wire to seat the stent into position within the vessel depends on the member used to lock the joining wire to the proximal end of the catheter assembly. For example, a joining wire which has a proximal end which is trimmed and secured to a connector at the proximal end of the catheter assembly must therefore be fully withdrawn and replaced with a separate guidewire for use in seating the stent into position within the vessel. In one embodiment of the invention, the joining wire also functions as a guidewire, with a proximal end slidably disposed out the proximal end of a guidewire locking mechanism releaseably securing the joining guidewire to the proximal end of the catheter. For example, in one embodiment, the guidewire locking mechanism has a collet member with a radially collapsible slotted head positioned within a proximal adapter or fitting on the proximal end of the catheter shaft. The guidewire locking mechanism saves physician time and effort by avoiding the removal and replacement of the joining wire. Additionally, the guidewire locking mechanism preferably is configured to facilitate manufacture of the catheter assembly and loading of the joining guidewire into the catheter. In one embodiment, the guidewire locking mechanism is in the locked mode with the distal end of the joining guidewire positioned distally beyond the distal end of the catheter first branch. In this configuration, the first branch and joining guidewire act as a fixed wire device, which is particularly preferred for delivering low profile devices through long, tortuous or diffusely deceased vasculature.

In one embodiment, the guidewire locking mechanism comprises a guidewire locking torque handle ("torquer") on a proximal end section of the joining guidewire. The torquer reversibly engages the joining guidewire to provide a finger hold for manipulating the joining guidewire. Additionally, the torquer releaseably connects to a proximal end of the catheter assembly (e.g. to the proximal adapter) to thereby releasably lock the joining guidewire to the catheter. In the locked configuration, the joining guidewire is held in place relative to the catheter, and in the unlocked configuration the joining guidewire is free to slide within the catheter with the torquer connected to the joining guidewire to provide a handle for the physician facilitating the independent manipulation of the joining guidewire. As a result, the catheter assembly limits procedure time and steps, with a joining wire that functions as both a useable guidewire that can be steered, and as a joining wire that releasably joins the distal tips of the two shafts together. Although discussed primarily in terms of use with a bifurcated stent delivery catheter, the guidewire locking torque handle can be used with a variety of suitable catheters having an over-the-wire shaft design in which the guidewire is slidably disposed in the catheter guidewire lumen. Therefore, with the guidewire locking torque handle tightened down onto the guidewire and simultaneously secured to the proximal end of an over-the-wire catheter (e.g., to the proximal adapter/hub), the guidewire locking torque handle of the invention provides a stable and fixed position and relation between the guidewire and catheter, so that the catheter can be advanced or withdrawn from the body lumen while maintaining its position relative to the guidewire.

Delivering and Implanting the Stent

A method of delivering and implanting the stent mounted on the catheter assembly is contemplated by the present invention. The bifurcated catheter assembly of the present invention provides two separate balloons in parallel which are advanced into separate passageways of an arterial bifurcation and the balloons are inflated either simultaneously or independently (or a combination thereof) to expand and implant the stent. More specifically, and in keeping with the invention, the catheter assembly is advanced through a guiding catheter (not shown) until the distal end of the catheter assembly reaches the ostium to the coronary arteries. An Rx guide wire is advanced into the coronary arteries to a point distal of the bifurcation or target site. In a typical procedure, the Rx guide wire will already be positioned at the target site after a pre-dilatation procedure. The catheter assembly is advanced over the Rx guide wire so that the catheter distal end is just proximal to the opening to the side branch vessel. Up to this point in time, the OTW guide wire (or mandrel or joining wire) remains within the catheter assembly and within the coupler so that the long balloon and the short balloon of the catheter assembly remain adjacent to one another to provide a low profile and prevent wire wrap. As the catheter assembly is advanced to the bifurcated area, the coupler moves axially relative to the distal end of the OTW guide wire (or mandrel or joining wire) a small distance (approximately 0.5 mm up to about 5.0 mm), but not pull completely out of the coupler, making it easier for the distal end of the catheter to negotiate tortuous turns in the coronary arteries. Thus, the slight axial movement of the coupler relative to the OTW guide wire (or mandrel or joining wire) distal end allows the tips to act or move independently, thereby increasing flexibility over the tips joined rigidly and it aids in the smooth tracking of the catheter assembly over the Rx guide wire. The proximal end of the OTW guide wire is releasably attached to the proximal hub as previously described. The OTW guide wire (or mandrel or joining wire) is removed or withdrawn proximally from the coupler, thereby uncoupling the long balloon and the short balloon. Thereafter, the OTW guide wire is advanced distally into the side branch vessel so that the catheter assembly can next be advanced distally over the Rx guide wire in the main vessel and the OTW guide wire in the side branch vessel. The separation between the Rx guide wire and the OTW guide wire allows the long balloon and the short balloon to separate slightly as the catheter assembly is further advanced over the Rx guide wire and the OTW guide wire. The catheter assembly advances distally until it reaches a point where the central opening on the stent is approximately adjacent to the opening to the side branch vessel, so that the catheter assembly can no longer be advanced distally since the balloons push against the carina and are somewhat constrained by the stent. One or more high percent tungsten/radiopaque markers are placed on the distal portion of the PEBAX balloon catheter assembly to aid in positioning the stent with respect to the bifurcation or target site. Once the long and short balloons with the stent mounted thereon are positioned in the main vessel just proximal to the side branch vessel, the long balloon and the short balloon are next inflated simultaneously or independently (or a combination thereof), to expand the stent in the main vessel and the opening to the side branch vessel. The central section of the stent is expanded into contact with the opening to the side branch vessel and the central opening should substantially coincide with the opening to the side branch vessel providing a clear blood flow path through the proximal opening of the stent and through the central opening into the side branch vessel. By inflating the long balloon and the short balloon substantially simultaneously, plaque shifting is avoided and access to the side branch is better preserved.

As discussed above, as the catheter assembly is advanced through tortuous coronary arteries, over the Rx guide wire, the central opening of the stent may or may not always be perfectly aligned with the opening to the side branch vessel, and may thus be "out of phase," and depending upon how many degrees out of phase, the stent may require repositioning or reorienting so that the central opening more closely coincides with the opening to the side branch vessel. The orientation of the central opening of the stent with respect to the opening to the side branch vessel can range anywhere from a few degrees to 180°. If the central opening of the stent is more than 90° out of phase with respect to the opening to the side branch vessel, it may be difficult to position the radiopaque marker, and thus the linear or longitudinal position of the stent. When the central opening is in the out of phase position, the stent of the invention still can be implanted and the central opening will expand into the opening of the side branch vessel and provide adequate coverage. In cases where the system is more than 90° out of phase, the Rx and OTW guide wires will be crossed causing a distal torque to be applied to help the system to rotate in phase. In the event rotation does not occur, the system can be safely deployed with adequate coverage and support as long as the radiopaque markers located on the distal end of the catheter reach the proper positioning as can be detected under fluoroscopy. The unique and novel design of the catheter assembly and the stent of the present invention minimizes the misalignment so that the central opening of the stent generally aligns with the opening to the side branch vessel, and is capable of stenting the opening to the side branch vessel even if the central opening is out of phase from the opening of the side branch vessel.

One aspect of the invention is directed to a method of delivering a stent to a patient's bifurcated blood vessel, generally comprising introducing and advancing within a patient blood vessel a stent delivery balloon catheter having a polymeric radiopaque distal tip marker secured to the first branch (e.g., side branch), and fluoroscopically imaging the polymeric radiopaque distal tip marker to determine the alignment of the first branch balloon relative to an opening of a side branch of the patient's blood vessel. Under fluoroscopy, the image of the polymeric radiopaque distal tip marker facilitates adjusting the alignment of the first branch balloon relative to the side branch opening of the blood vessel both before and after the two distal tips of the catheter are uncoupled. It also facilitates placement of a wire in the side branch vessel after the joining mandrel is removed by making visible the tip where the wire will exit the catheter.

After the stent of the present invention has been implanted at the bifurcation, if necessary a second stent can be implanted in the side branch vessel so that the second stent abuts the central opening of the stent of the present invention.

As disclosed herein, there are multiple embodiments of a bifurcated stent and stent delivery catheter. The specific embodiments are not intended to be limiting, but have a wide range of applications. Accordingly, the stents disclosed herein can be delivered with other types of balloon catheters, and the balloon catheters disclosed herein can be used for multiple purposes including expanding or dilating an artery or delivering stents having configurations other than those disclosed herein. The stents also can be post-dilated using other catheters of different sizes in either the main branch or the side branch.

BRIEF DESCRIPTION OF THE DRAWINGS

FIGS. 18A, 18B, 18C, and 18D are schematic diagrams of bifurcated vessels showing plaque in the region of the bifurcation.

FIG. 23 is an elevational view of the catheter assembly for delivering and implanting the stent of the invention.

FIG. 24 is a cross-sectional view taken along lines 24-24 depicting the cross-section of the proximal shaft of the catheter.

FIG. 25 is a cross-sectional view taken along lines 25-25 depicting the cross-section of a portion of the catheter shaft.

FIG. 26A is a cross-sectional view taken along lines 26A-26A depicting the cross-section of the Rx catheter shaft.

FIG. 26B is a cross-sectional view taken along lines 26B-26B depicting the cross-section of the over-the-wire shaft.

FIG. 27 is a longitudinal cross-sectional view of the coupler.

FIG. 28A is a longitudinal cross-sectional view depicting a portion of the catheter distal end including the radiopaque markers.

FIG. 28B is a transverse cross-sectional view taken along lines 28B-28B depicting the inner member and long balloon.

FIG. 29 is an elevational view of one embodiment of the catheter assembly for delivering and implanting the stent of the invention.

FIG. 33 is a longitudinal cross-sectional view of the coupler depicting a guide wire slidably positioned in the dead-end lumen of the coupler.

FIG. 50 is an enlarged, longitudinal sectional view of the catheter of FIG. 46 taken within circle 50.

FIG. 51 is a transverse cross section taken along line 51-51 in FIG. 50

FIG. 52 is a longitudinal cross section of a guidewire locking mechanism embodying features of the invention, having a proximal fitting member and a collet member with a radially collapsible slotted head.

FIG. 53 a longitudinal cross section of a guidewire locking mechanism embodying features of the invention, having a fitting with a radially collapsible slotted inner extension.

FIG. 54 is a longitudinal cross section of a guidewire locking torque device embodying features of the invention.

DETAILED DESCRIPTION OF THE PREFERRED EMBODIMENTS

Figure 1:
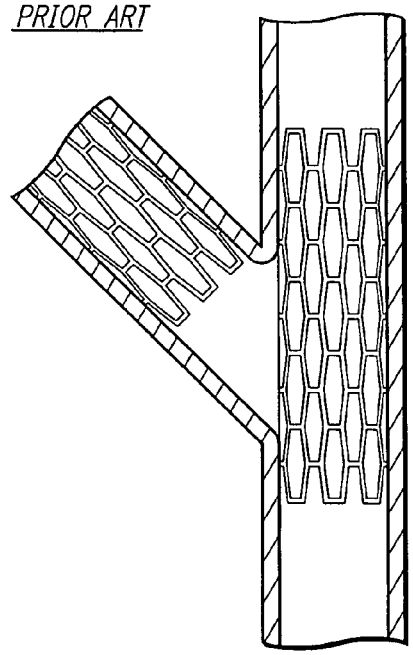
FIG. 1 is an elevational view of a bifurcation in which a prior art "T" stent is in a side branch ostium followed by the stenting of the main vessel across the branch ostium.

The present invention includes a stent and stent delivery catheter assembly and method for treating bifurcations in, for example, the coronary arteries, veins, peripheral vessels and other body lumens. Prior art attempts at implanting intravascular stents in a bifurcation have proved less than satisfactory. For example, FIGS. 1-4 depict prior art devices which include multiple stents being implanted in both the main vessel and a side branch vessel. In FIG. 1, a prior art "T" stent is implanted such that a first stent is implanted in the side branch near the origin of the bifurcation, and a second stent is implanted in the main vessel. With this approach, portions of the side branch vessel are left uncovered, and blood flow to the side branch vessel must necessarily pass through the main vessel stent, causing possible obstructions or thrombosis.

Figure 2:
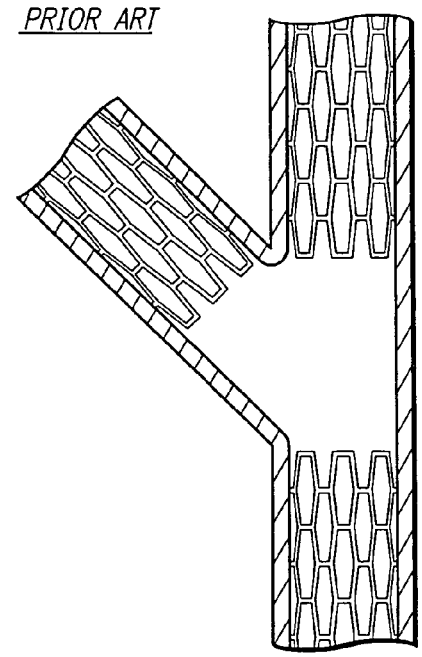
FIG. 2 is an elevational view of a bifurcation in which "touching" prior art stents are depicted in which one stent is implanted in the side branch, a second stent implanted in a distal portion of the main vessel next to the branch stent, with interrupted placement of a third stent implanted more proximally in the main vessel.
Figure 3:
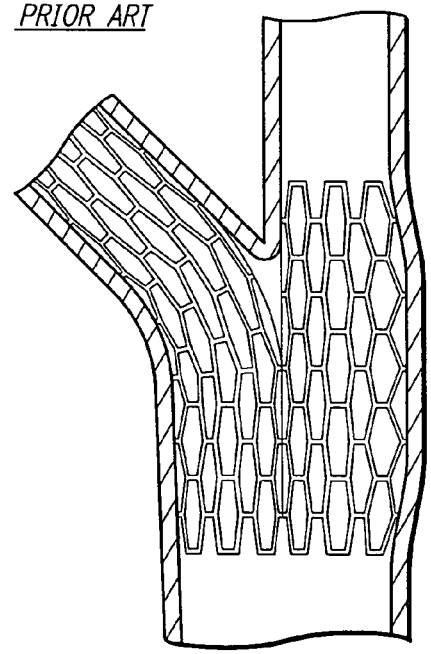
FIG. 3 is an elevational view of a bifurcation depicting "kissing" stents where a portion of one stent is implanted in both the side branch and the main vessel and adjacent to a second stent implanted in the main vessel creating a double-barreled lumen in the main vessel proximal to the bifurcation.
Figure 4:
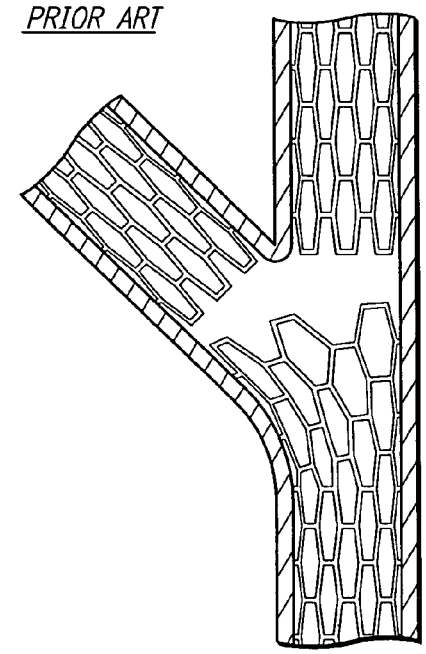
FIG. 4 is an elevational view of a prior art "trouser legs and seat" stenting approach depicting one stent implanted in the side branch vessel, a second stent implanted in a proximal portion of the main vessel, and a close deployment of a third stent distal to the bifurcation leaving a small gap between the three stents of an uncovered luminal area.

Referring to FIG. 2, three prior art stents are required to stent the bifurcation which leaves a large gap in vessel coverage between the stents. In FIG. 3, the prior art method includes implanting two stents side by side, such that one stent extends into the side branch vessel and the main vessel, and the second stent is implanted in the main vessel. This results in a double-barreled lumen which can present problems such as thrombosis and turbulence in blood flow. Referring to the FIG. 4 prior art device, a first stent is implanted in the side branch vessel, a second stent is implanted in a proximal portion of the main vessel, and a third stent is implanted distal to the bifurcation, thereby leaving a small gap between the stents and resulting in an uncovered luminal area.

All of the prior art devices depicted in FIGS. 1-4 have various drawbacks which have been solved by the present invention.

Figure 5A:
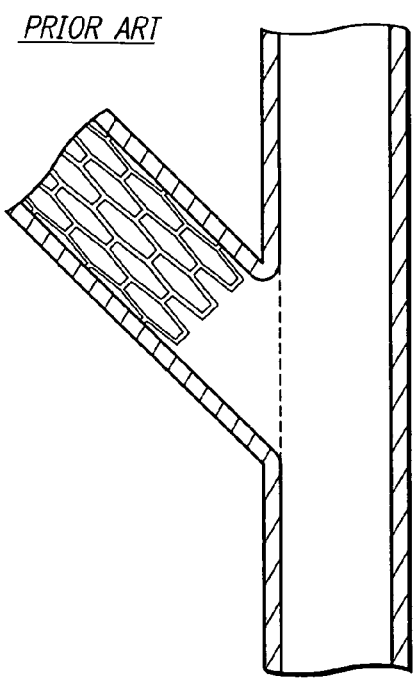
FIG. 5A is an elevational view of a bifurcation in which a prior art stent is implanted in the side branch vessel.
Figure 5B:
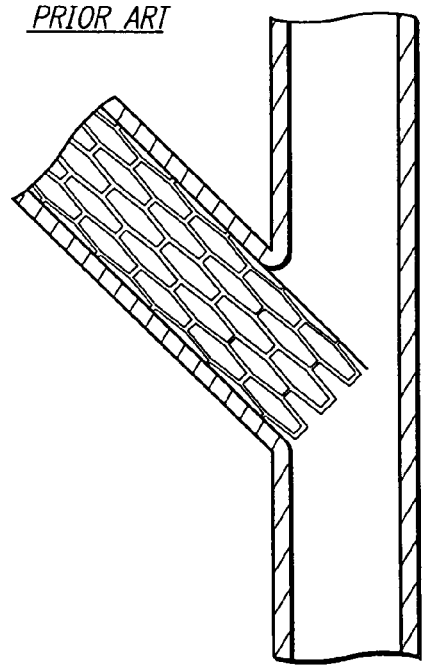
FIG. 5B is an elevational view of a bifurcation in which a prior art stent is implanted in the side branch vessel, with the proximal end of the stent extending into the main vessel.

In treating a side branch, if a prior art stent is used in which there is no acute angle at the proximal end of the stent to match the angle of the bifurcation, a condition as depicted in FIGS. 5A and 5B will occur. That is, a stent deployed in the side branch vessel will leave a portion of the side branch vessel exposed, or as depicted in 5B, a portion of the stent will extend into main vessel.

The stent of the present invention can be implanted in the main or side branch vessels to treat a number of disease configurations at a bifurcation, but not limited to, the following:

1. Treatment of a parent or main vessel and the origin of the side branch at a bifurcation with any angle associated between the side branch and parent vessel.
2. Treatment of a parent vessel proximal to the carina and the side branch vessel simultaneously.
3. Treatment of the proximal vessel extending only into the origin of the side branch and the origin of the distal parent at the bifurcation.
4. Treatment of the area at the bifurcation only.
5. The origin of an angulated posterior descending artery.
6. The origin of an LV extension branch just at and beyond the crux, sparing the posterior descending artery.
7. The origin of a diagonal from the left anterior descending.
8. The left anterior descending at, just proximal to, or just distal to the diagonal origin.
9. The origin of a marginal branch of the circumflex.
10. The circumflex at, just proximal to, or just distal to the marginal origin.
11. The origin of the left anterior descending from the left main.
12. The origin of the circumflex from the left main.
13. The left main at or just proximal to its bifurcation.
14. Any of many of the above locations in conjunction with involvement of the bifurcation and an alternate vessel.
15. Any bifurcated vessels within the body where conventional stenting would be considered a therapeutic means of treatment proximal or distal to the bifurcation.

The present invention solves the problems associated with the prior art devices by providing a stent which adequately covers the main branch vessel and extends partially into the side branch vessel to cover one aspect of the origin of the side branch vessel as well. The invention also includes a stent delivery catheter assembly and the method of crimping the stent on the catheter and delivering and implanting the stent in the body, especially the coronary arteries.

The Stent Pattern

The stent pattern of the present invention is novel in that it provides for vessel wall coverage of the main branch vessel and at least partial coverage of the origin of the side branch vessel. More specifically, in FIGS. 6-22, several embodiments of stent 10 are shown. Once stent 10 is implanted in the main branch vessel and the opening to the side branch vessel, a second, conventional stent can be implanted in the side branch vessel, essentially abutting a portion of stent 11.

The stent 10 of the present invention has a cylindrical body 11 that includes a proximal end 12 and a distal end 13. The stent has an outer surface 14 which contacts the vascular wall when implanted and an inner surface 15 through which blood flows when the stent is expanded and implanted. The stent can be described as having connected rings 16 aligned along a common longitudinal axis of the stent. The rings are formed of undulating portions which include peaks 17 that are configured to be spread apart to permit the stent to be expanded to a larger diameter or compressed tightly toward each other to a smaller diameter when mounted on a catheter. The rings are connected to each other by at least one link 18 between adjacent rings. Typically, there are three links that connect adjacent rings and the links of one ring are generally circumferentially offset from the links of an adjacent ring. While the links 18 typically are offset as indicated, this is not always the case.

A central opening 19 in the stent 10 allows the passage of a balloon contained on the delivery system. The stent is to be crimped tightly onto two separate expandable members or balloons of a catheter. Typically, as will be described in more detail below, the balloons on the catheter are balloons similar to a dilatation-type balloon for conventional dilatation catheters. In the present invention, the stent 10 is configured such that the stent has a distal opening 20 and a proximal opening 21 that are in axial alignment and through which a longer balloon extends. The central opening 19 is adjacent a portal section 22 through which a shorter balloon extends. Although the stent is crimped tightly onto both the long and short balloons as will be described, other delivery catheters can be used to deliver and implant the stent.

With all of the embodiments of the stent 10 disclosed herein, the rings 16 can be attached to each other by links 18 having various shapes, including straight links 23 or non-linear links 24 having curved portions. The non-linear links, as shown in FIGS. 6-13, can have undulating portions 25 that are transverse to the longitudinal axis of the stent and act as a hinge to enhance the flexibility of the stent.

Figure 6A:
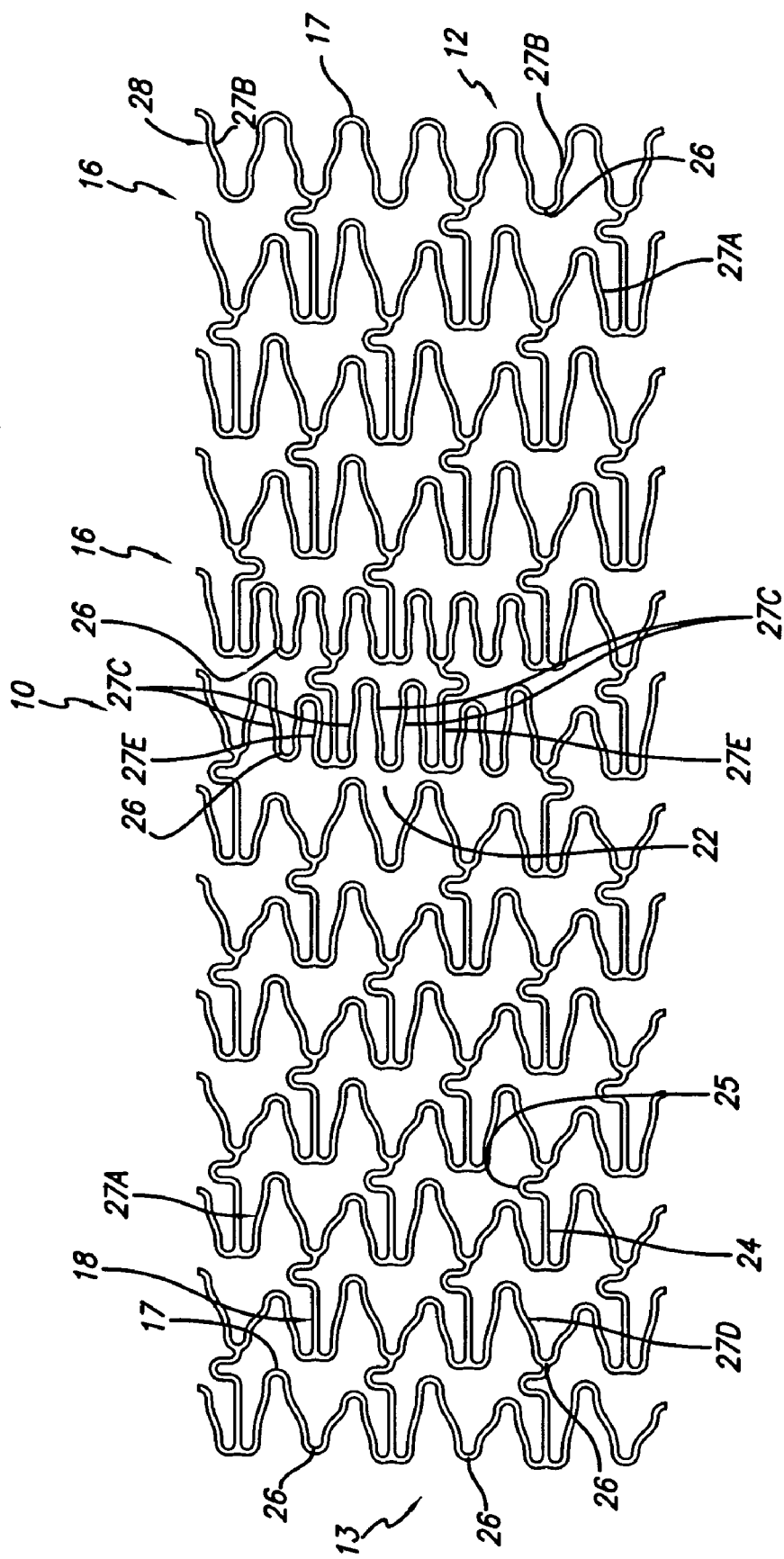
FIG. 6A is an elevational view of a stent in a flattened condition and depicting the portal region of a bifurcated stent.
Figure 6B:
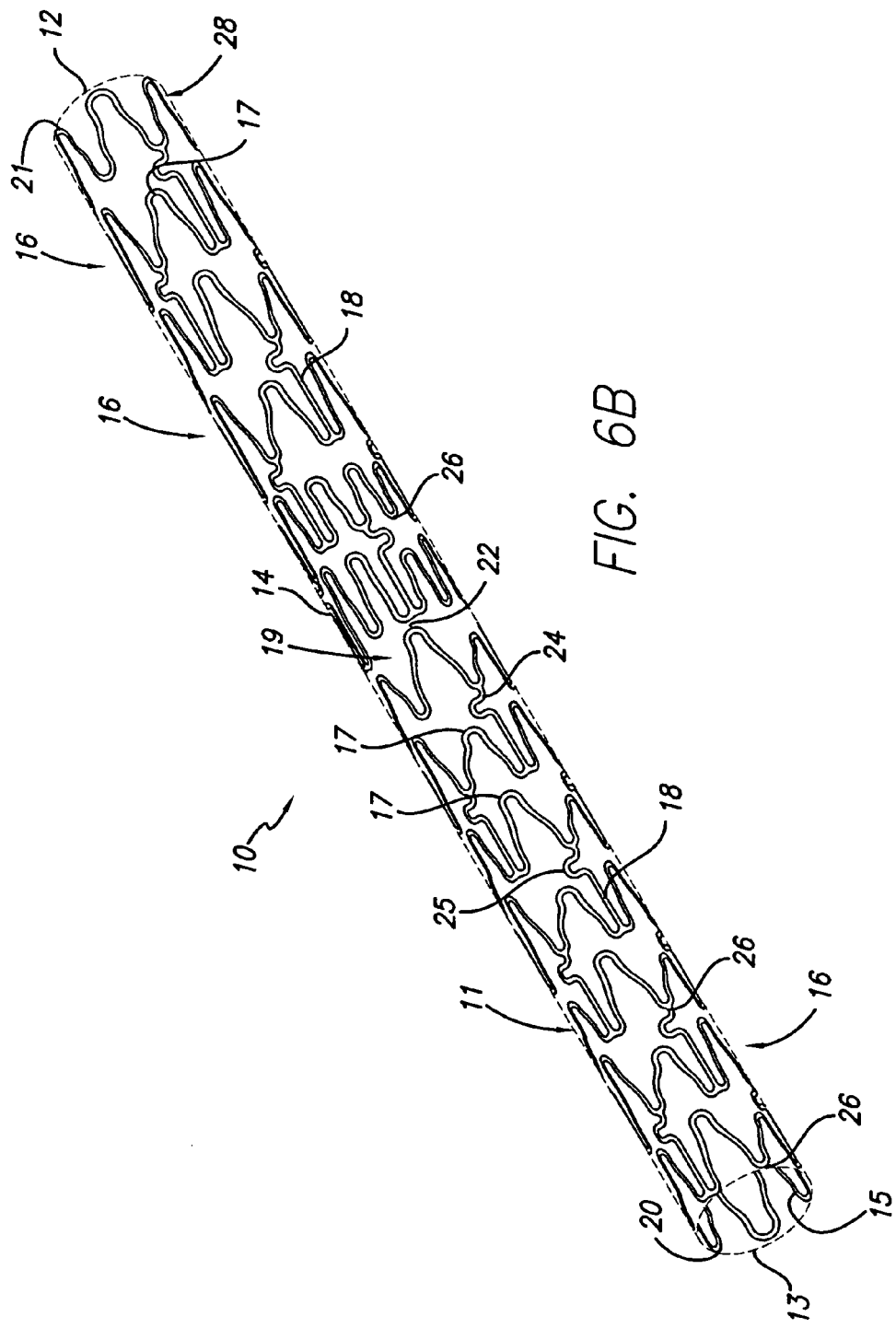
FIG. 6B is a perspective view depicting the stent of FIG. 6A rolled into a cylinder.

In keeping with the invention, and with reference to FIGS. 6A and 6B, stent 10 has a cylindrical body 11 and a proximal end 12 and a distal end 13. The stent outer surface 14 contacts the vessel when the stent is expanded, and the stent inner surface 15 provides a smooth and unobstructed lumen through which blood flows when the stent is expanded in a vessel. Stent 10 is comprised of multiple rings 16 that are connected by nonlinear links 24, each having undulating portions 25. The undulating portions 25 of the nonlinear links 24 extend circumferentially in a direction transverse to the longitudinal axis of the stent. In this embodiment, there are 13 rings, ring No. 1 being at the proximal end 12 of the stent while ring No. 13 is at the distal end 13 of the stent. In this embodiment, there are three nonlinear links 24 connecting each of the rings 16 with the exception of two nonlinear links 24 connecting ring No. 6 to ring No. 7. This area between the sixth and seventh ring 16 is portal section 22 which will expand into the opening of the side branch vessel when the stent is expanded, as will be hereinafter described.

In further keeping with the invention shown in FIGS. 6A and 6B, each of the rings 16 is made up of peaks 17 which point in the direction of the stent proximal end 12, valleys 26 which point in the direction of the stent distal end 13, and bar arms 27A which connect the peaks 17 and the valleys 26. In this embodiment, bar arms 27A have different widths in certain rings and different lengths in certain rings in order to provide specific attributes to stent expansion and vessel wall coverage. For example, bar arms 27B of proximal end ring 28 (ring No. 1) are approximately the same length and each has a width of approximately 0.09144 mm (0.0036 inch). Further, the peaks 17 and valleys 26 of proximal end ring 28 have a greater radius than the peaks and valleys of the other rings in the stent in order to provide a more open area for gripping the balloon when the stent is compressed onto the balloon. In further keeping with the invention, bar arms 27C connect the peaks 17 and valleys 26 of rings in a proximal section of the stent (ring Nos. 2-4) and several of the bar arms 27C in the portal section 22 of the stent. The bar arms 27C are relatively longer than other of the bar arms connecting peaks and valleys in the stent, which allows the portal section 22 to cover more area in the opening to the side branch vessel when the stent is expanded. The portal section rings (rings 5-6) have a greater number of peaks and valleys than in the proximal or distal section rings which also provides for a greater expansion diameter. Bar arms 27D that connect peaks 17 and valleys 26 in the distal section of the stent (ring Nos. 7-13) are relatively shorter than both the bar arms 27C connecting peaks and valleys in the portal section 22 of the stent and the bar arms 27A in the proximal section of the stent. Further, the width of the bar arms in various of the rings 16 can be varied in order to increase or decrease flexibility, with wider bar arms 27A being less flexible than relatively narrower width bar arms. The width of bar arms 27A in rings 16 in the proximal section (ring Nos. 2, 3 and 4) have a width of approximately 0.09652 mm (0.0038 inch). The bar arms 27C in the portal section 22 (ring Nos. 5 and 6) all have a width of approximately 0.09144 mm (0.0036 inch) with the exception of bar arms 27E which have a width of approximately 0.08128 mm (0.0032 inch). The widths of the bar arms 27D in the rings 16 in the distal section (ring Nos. 7-13) are approximately 0.09144 mm (0.0036 inch). The radial thickness of the stent is constant at approximately 0.08128 mm (0.0032 inch). The width of the various bar arms and the radial thickness of the stent all can be varied depending upon a particular application, and the dimensions disclosed herein are exemplary. Further, varying the width of the apex or crest of the peaks and valleys also affects flexibility, with relatively narrower widths providing greater flexibility.

Other features of the invention shown in FIGS. 6A and 6B include a greater number of peaks 17 and valleys 26 in the portal section 22 rings than in other of the rings in the stent. For example, ring No. 5 has eight peaks 17, ring No. 6 has eight peaks 17, proximal end ring 28 has six peaks 17, while all of the other rings in stent 10 have six peaks 17. The greater number of peaks 17 in the portal section 22 provides for greater expansion of the stent in that area and provides more coverage of the opening to the side branch vessel as the portal section 22 expands into and apposes the opening to the side branch vessel. The embodiments shown in FIGS. 6A and 6B can be modified by increasing or decreasing the number of rings 16 on either side of the portal section 22. For example, for a 12 mm long stent (not shown) there are a total of nine rings, with the portal section 22 positioned between the sixth and seventh rings and only three rings positioned in the distal section of the stent.

Figure 7A:
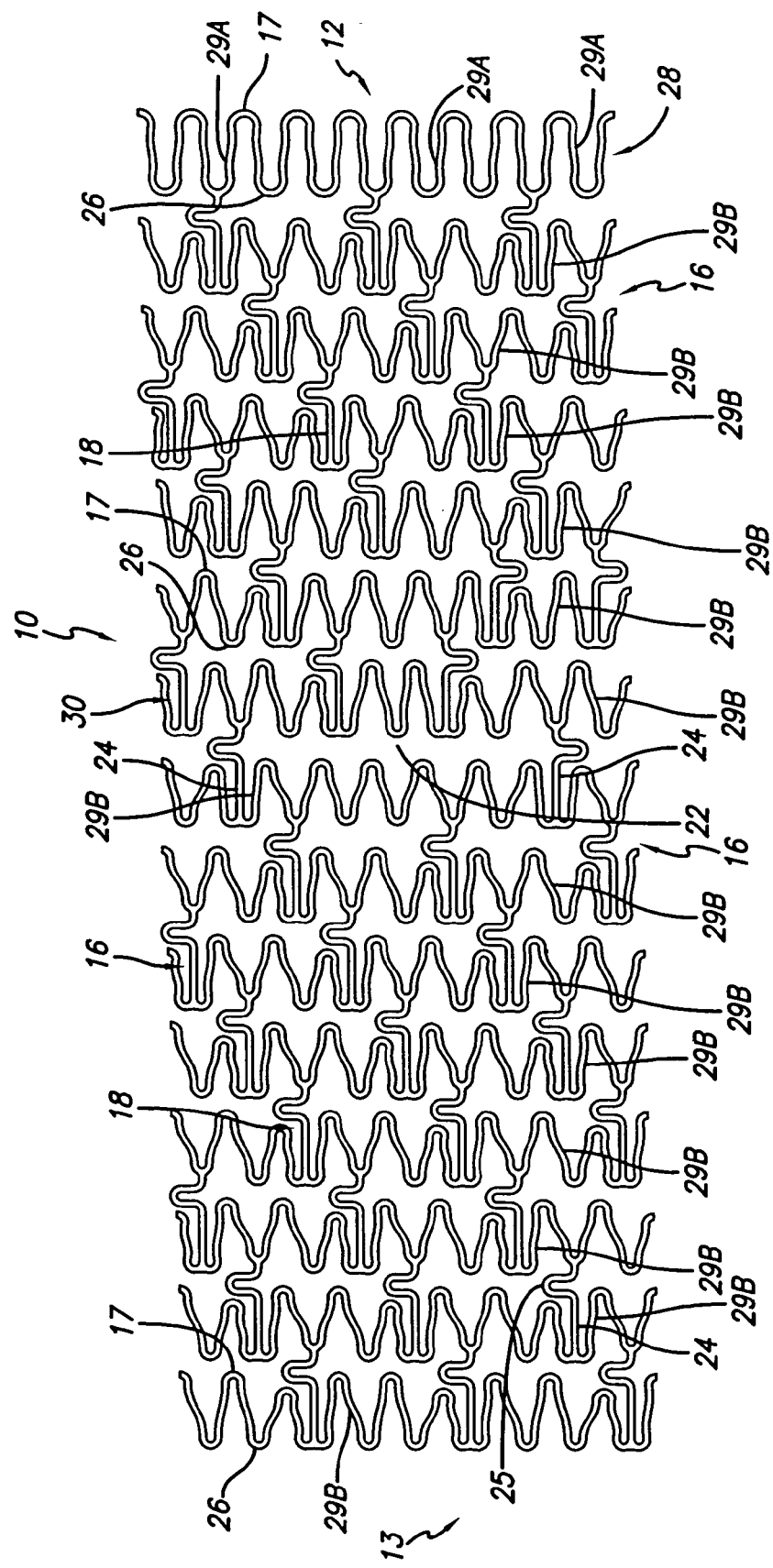
FIG. 7A is an elevational view of a stent in a flattened condition and depicting the portal region of a bifurcated stent.
Figure 7B:
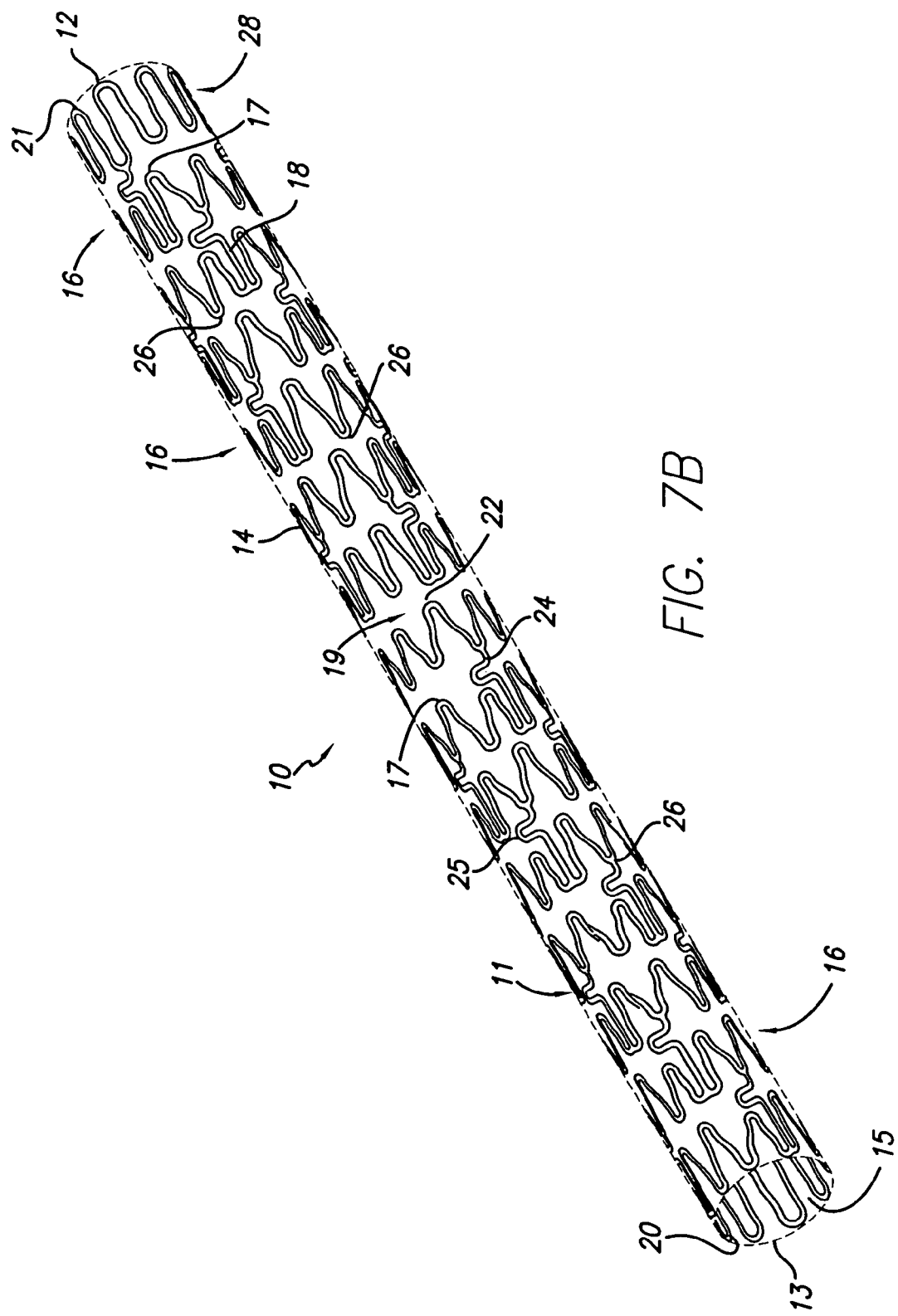
FIG. 7B is a perspective view depicting the stent of FIG. 7A rolled into a cylinder.

In another embodiment, as shown in FIGS. 7A and 7B, stent 10 is substantially similar to that shown in FIGS. 6A and 6B. In FIGS. 7A and 7B, there are fifteen rings 16 with the portal section 22 between ring Nos. 7 and 8, counting from the proximal end 12 toward the distal end 13. In this embodiment, bar arms 29A of the proximal end ring 28 have one length, and bar arms 29B of all of the other rings 16 have substantially the same length, which is shorter than the length of the bar arms 29A. Further, the width of bar arms 29A is approximately 0.09144 mm (0.0036 inch) while all of the other bar arms 29B have a width of approximately 0.08128 mm (0.0032 inch). The radial thickness of stent 10 in this embodiment is constant throughout and is approximately 0.08128 mm (0.0032 inch). One other distinction between the stent 10 of FIGS. 6A and 6B and the stent 10 of FIGS. 7A and 7B is that there are a uniform number of peaks 17 in all of the rings 16 in FIGS. 7A and 7B. Specifically, each of the rings 16 have nine peaks 17, which insures uniform wall coverage throughout the length of the stent. Importantly, the nine peaks 17 in the portal section 22 provide adequate coverage at the opening to the side branch vessel when stent 10 is expanded in the main vessel and into the opening of the side branch vessel as will be described herein. For even greater expansion in the portal section 22, there can be eleven peaks 17 (not shown) which also increases wall coverage. Similar to FIGS. 6A and 6B, the portal ring 30 in FIGS. 7A and 7B is attached to the ring distal of the portal ring by two nonlinear links 24. The undulating portions 25 of the nonlinear links 24 extend in opposite directions transverse to the longitudinal axis of the stent. With only two nonlinear links 24 connecting the portal ring to the ring 16 distal of it, this creates a larger portal section 22 which allows the portal area to be slightly out of alignment with the side branch vessel during delivery and still be acceptable when the portal section 22 expands into the opening of the side branch vessel.

Figure 8A:
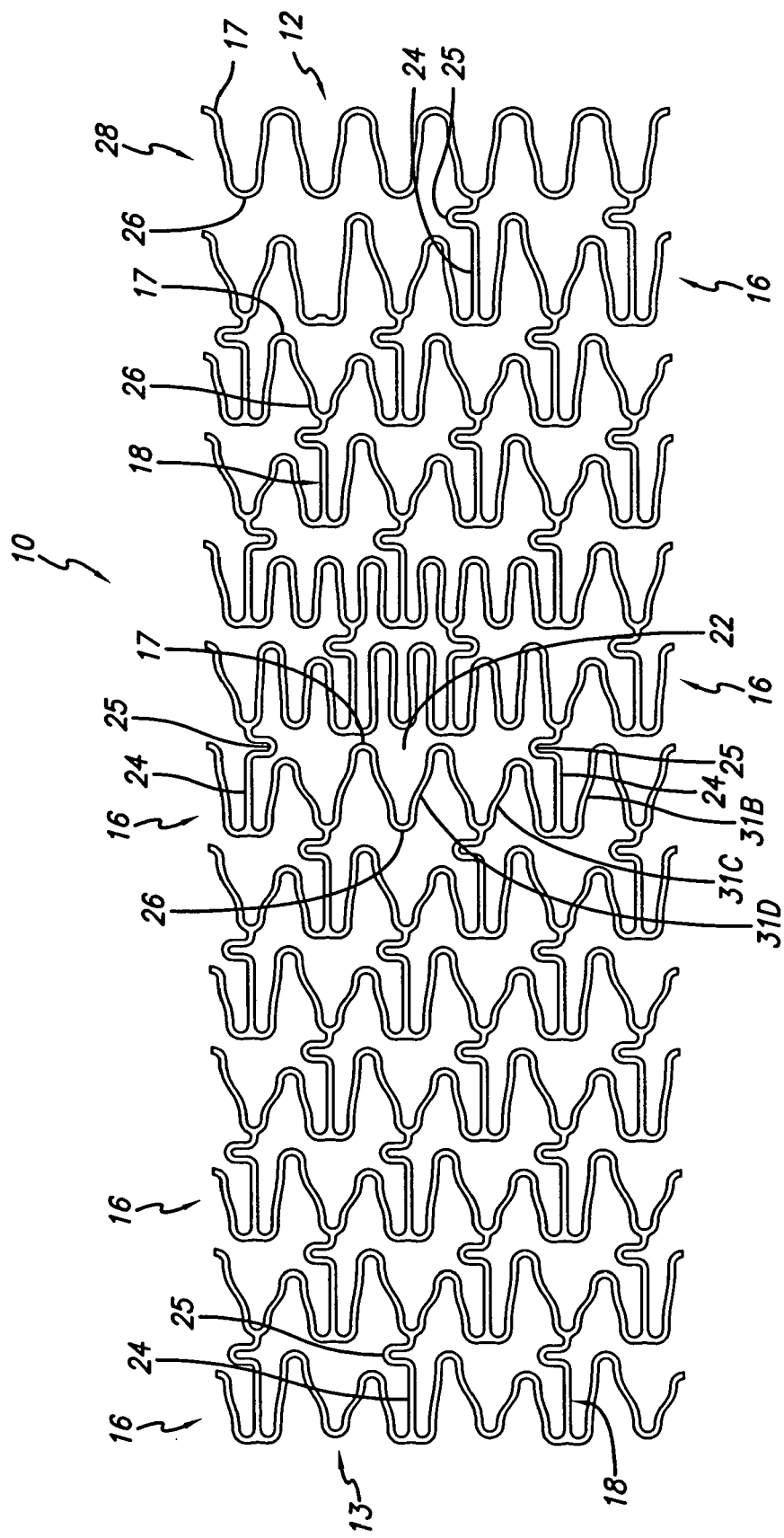
FIG. 8A is an elevational view of a stent in a flattened configuration depicting a bifurcated stent.
Figure 8B:
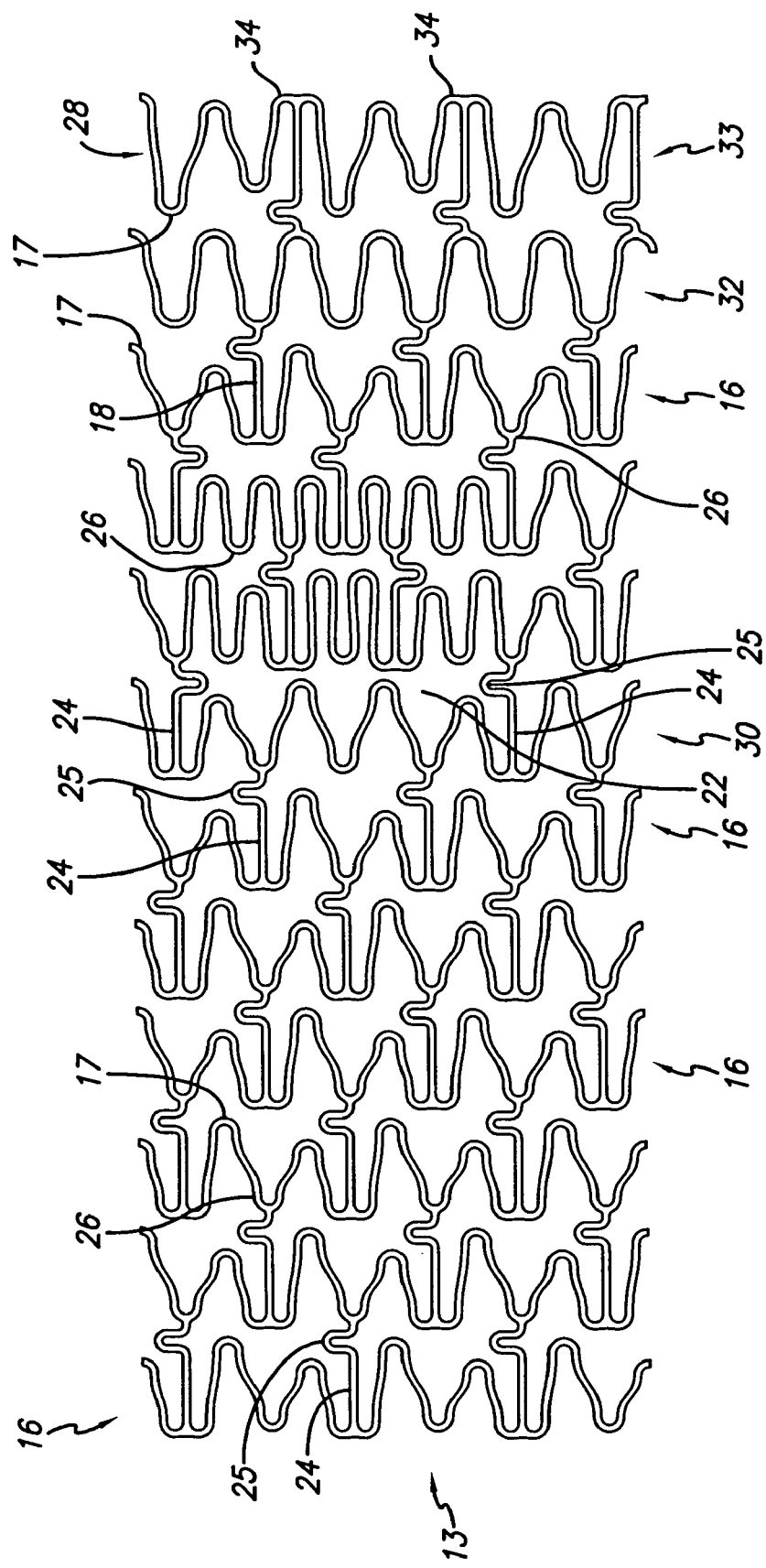
FIG. 8B is an elevational view of a stent in a flattened configuration depicting a bifurcated stent.

In another embodiment, shown in FIG. 8A, stent 10 has a cylindrical body 11 and a proximal end 12 and a distal end 13. Stent 10 is shown in a flattened configuration, however, in use it is in the form of a cylinder (not shown) and typically is formed by laser cutting a tubular member. The stent is comprised of multiple rings 16 that are connected by non-linear links 24, each having undulating portions 25. The undulating portions 25 of the non-linear links 24 extend circumferentially in a direction transverse to the longitudinal axis of the stent. In this embodiment, there are thirteen rings, with ring No. 1 being at the proximal end 12 of the stent while ring No. 13 is at the distal end 13 of the stent. In this embodiment, there are three non-linear links 24 connecting each of the rings 16 with the exception of two non-linear links 24 connecting ring No. 6 to ring No. 7. The area between the sixth and seventh ring is portal section 22 that will expand into the opening into the side branch vessel when the stent is expanded as will be hereinafter described. In keeping with the invention as shown in FIGS. 8A and 8B, each of the rings 16 is formed of peaks 17 which point in the direction of the stent proximal end 12, and valleys 26 which point in the direction of the stent distal end 13. Bar arms 31A connect the peaks 17 and the valleys 26. In this embodiment, the undulating portion 25 of the two links between ring Nos. 6 and 7 (the portal region 22), point toward each other in a direction transverse to the longitudinal axis of the stent. This provides space for bar arm 31B to be more like bar arm 31C instead of bar arm 31D. The bar arms and struts around bar arm 31B will expand more and move the non-linear links 24 in the portal section 22 toward the side branch vessel when the stent is expanded. This will reduce the ring separation between rings 6 and 7, especially when the stent is being deployed in a curved area of the vessel. In an alternative embodiment, the proximal end ring 28 (ring No. 1) is connected to the adjacent cylindrical ring 16 (ring No. 2) by two non-linear links 24 having undulating portions 25. In this embodiment, there is additional flexibility at the proximal end of the stent which will help with preventing strut flaring and will reduce the likelihood of the stent catching on the guide catheter when the stent is pulled back toward the guide catheter during delivery and implantation of the stent.

In another embodiment as shown in FIG. 8B, stent 10 is substantially similar to that shown and described for FIG. 8A. In this embodiment, cylindrical ring 32 (ring No. 2 counting from the proximal end 12 of stent 10) has substantially the same configuration as proximal end ring 28 shown in FIG. 8A. Proximal end ring 33 has a configuration similar to ring No. 3 of stent 10, only the peaks 17 and the valleys 26 point in opposite directions. Proximal end ring 33, due to its configuration having W-shaped elements 34, provides additional support at the proximal end of the stent for increased stent retention on the balloon portion of the catheter and as extra retention as the catheter is pulled back into the guiding catheter (not shown). The W-shaped elements 34 also reduce flaring of proximal end ring 33. In this embodiment, proximal end ring 33 is connected to the adjacent ring 32 by three non-linear links 24 which also provide extra support at the proximal end 12 of the stent. In this embodiment, there are fewer rings proximal to the portal section 22 than in other designs such as shown in FIG. 8A. This provides for more flexibility for treating bifurcations with a short vessel length proximal to the side branch vessel. More specifically, in this embodiment, as shown in FIG. 8B, there are four rings proximal to the portal ring 30, while there are seven rings distal to the portal ring 30. As with previous embodiments, all of the rings are connected to each other by non-linear links 24 having undulating portions 25 that extend transverse to the longitudinal axis of the stent. The portal ring 30 is connected to the ring 16 distal of it by two non-linear links 24, while all other rings are attached to each other by three non-linear links 24.

Figure 9:
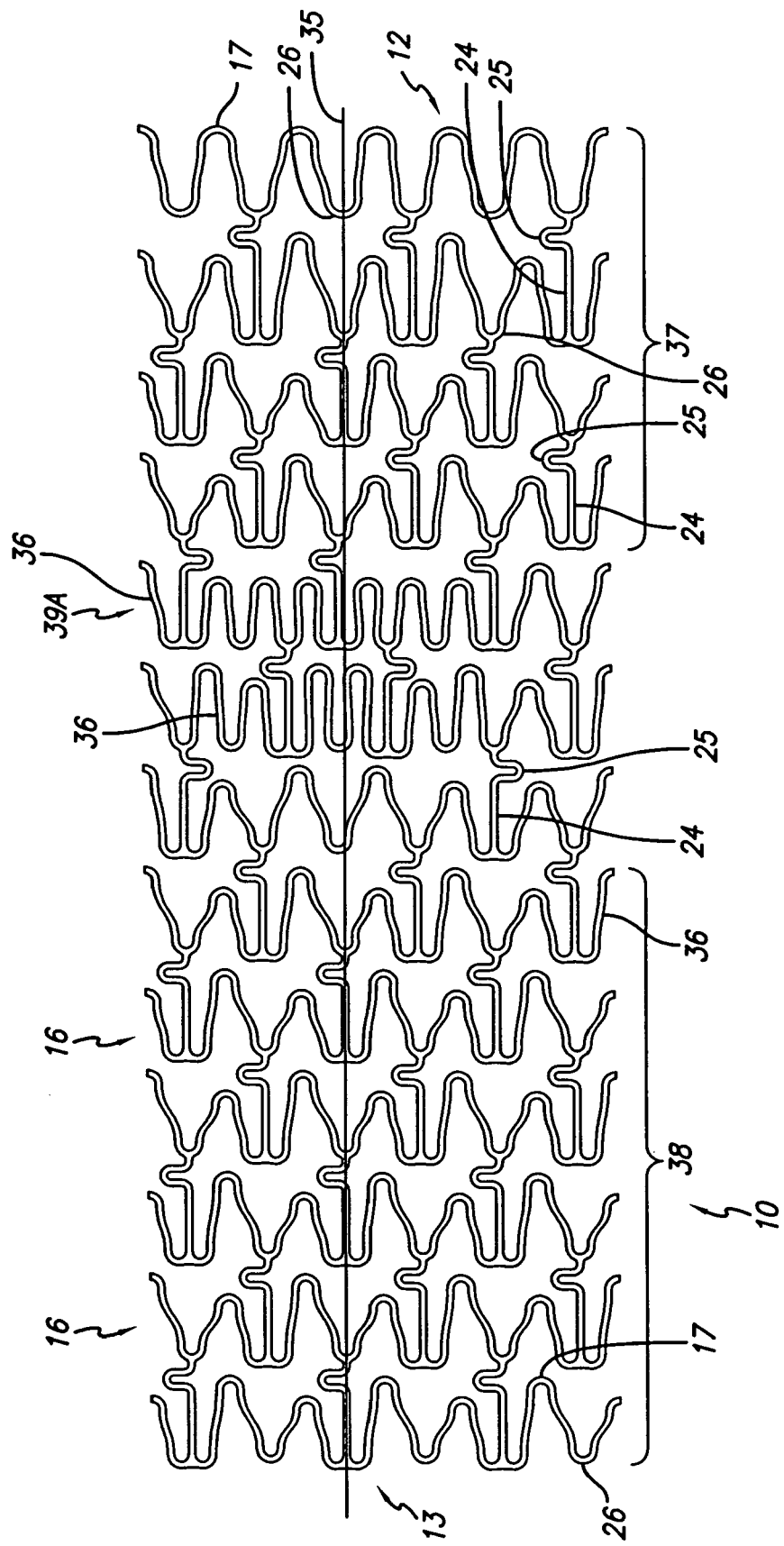
FIG. 9 is an elevational view of a stent in a flattened configuration depicting the portal region of a bifurcated stent.

In another embodiment, as shown in FIG. 9, stent 10 has a cylindrical body 11 (not shown) and a proximal end 12 and a distal end 13. The stent of this embodiment is substantially similar to that shown in FIGS. 6A and 6B. In this embodiment, stent 10 has multiple rings 16 that are connected by non-linear links 24, each of the links having undulating portions 25. The undulating portions 25 of the non-linear links 24 extend circumferentially in a direction transverse to the longitudinal axis 35 of the stent. In this embodiment, there are thirteen rings, ring No. 1 being at the proximal end 12 of the stent while ring No. 13 is at the distal end 13 of the stent. Further, there are three non-linear links 24 connecting each of the rings 16 with the exception of two non-linear links 24 connecting ring No. 6 to ring No. 7. The area between the sixth and seventh ring 16 is portal section 22 that expands into the opening of the side branch vessel when the stent is expanded, as will be further described herein. In further keeping with the invention shown in FIG. 9, each of the rings 16 is made up of peaks 17 which point in the direction of stent proximal end 12, valleys 26 which point in the direction of the stent distal end 13, and bar arms 36 which connect the peaks 17 and the valley 26. In this embodiment, proximal section 37 includes ring Nos. 1-4 and distal section 38 includes ring Nos. 7-13. Portal ring 39A and 39B represent ring Nos. 5 and 6, respectively. Portal rings 39A and 39B have eight peaks, while all of the rings in the proximal section 37 and the distal section 38 have six peaks. The rings in the proximal section 37 have larger expansion diameters than the rings 16 in the distal section 38. The greater expansion diameters in the proximal section 37 rings will accommodate any post-dilatation using a well known kissing-balloon technique.

Figure 10:
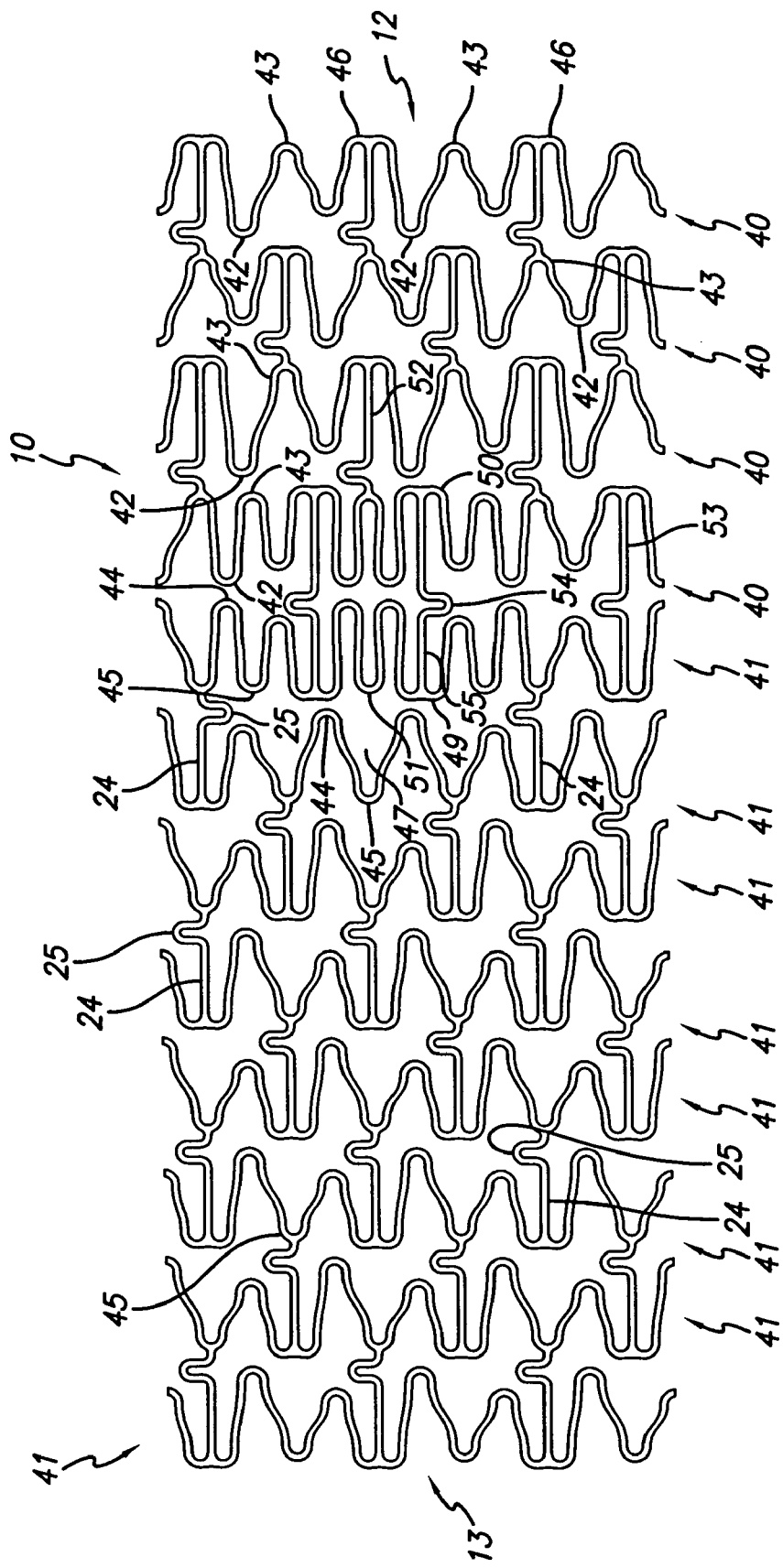
FIG. 10 is an elevational view of a stent in a flattened configuration depicting a bifurcated stent.

In another embodiment, shown in FIG. 10, stent 10 includes rings 16 comprised of first rings 40 and second rings 41. First rings 40 include first peaks 42 and first valleys 43 while second rings 41 include second peaks 44 and second valleys 45. In this embodiment, first peaks 42 of first rings 40 point in a direction toward distal end 13 while second peaks 44 of second rings 41 point toward proximal end 12 of stent 10. Stated differently, stent 10 has thirteen rings, ring No. 1 being at the proximal end 12 and ring No. 12 being at distal end 13 of the stent. Ring Nos. 1 through 4 include first rings 40, while ring Nos. 5 through 12 include second rings 41. In this configuration the W-shaped member 46 at the proximal end 12 of the stent can include two or three non-linear links 24 which allows the flexibility of the proximal end of the stent to be modified to allow a smooth guide pull-back. In the embodiment shown in FIG. 10, there are three non-linear links 24 connecting adjacent links to each other with the exception of the connection between ring Nos. 5 and 6, which have two non-linear links 24 connecting the two rings. The area between ring Nos. 5 and 6 is portal region 47 which is configured to expand into the opening of a side branch vessel when the stent is expanded and implanted in a bifurcated vessel. In further keeping with the invention, non-linear links 55 are substantially longer than non-linear links 24 and are configured to allow ring No. 5 (counting from proximal end 12) to expand and extend further into the side branch vessel in order to provide more coverage at the opening to the side branch vessel. For example, as the stent expands during implantation, the center line of most of the rings stay in the same position. With respect to ring Nos. 4 and 5, as the stent expands W-shaped members 49 and 50 stay approximately the same distance apart which then forces W-shaped member 49 into the side branch vessel along with peak 51. At the same time, non-linear link 52 helps keep the rings from being pushed away from the opening to the side branch vessel. Non-linear link 53 also exhibits similar behavior, but it may not necessarily be aligned with the opening to the side branch vessel and have as significant an impact as does non-linear link 52. The undulating portion 54 of non-linear link 55 adds flexibility to W-shaped members 49 and 50, however, it may reduce the extension of the W-shaped member 49 and peak 51 into the side-branch vessel. As an alternative embodiment, non-linear link 55 can be a straight link which would reduce flexibility, but allow the W-shaped member 49 and peak 51 to extend even further into the side branch vessel.

Figure 11:
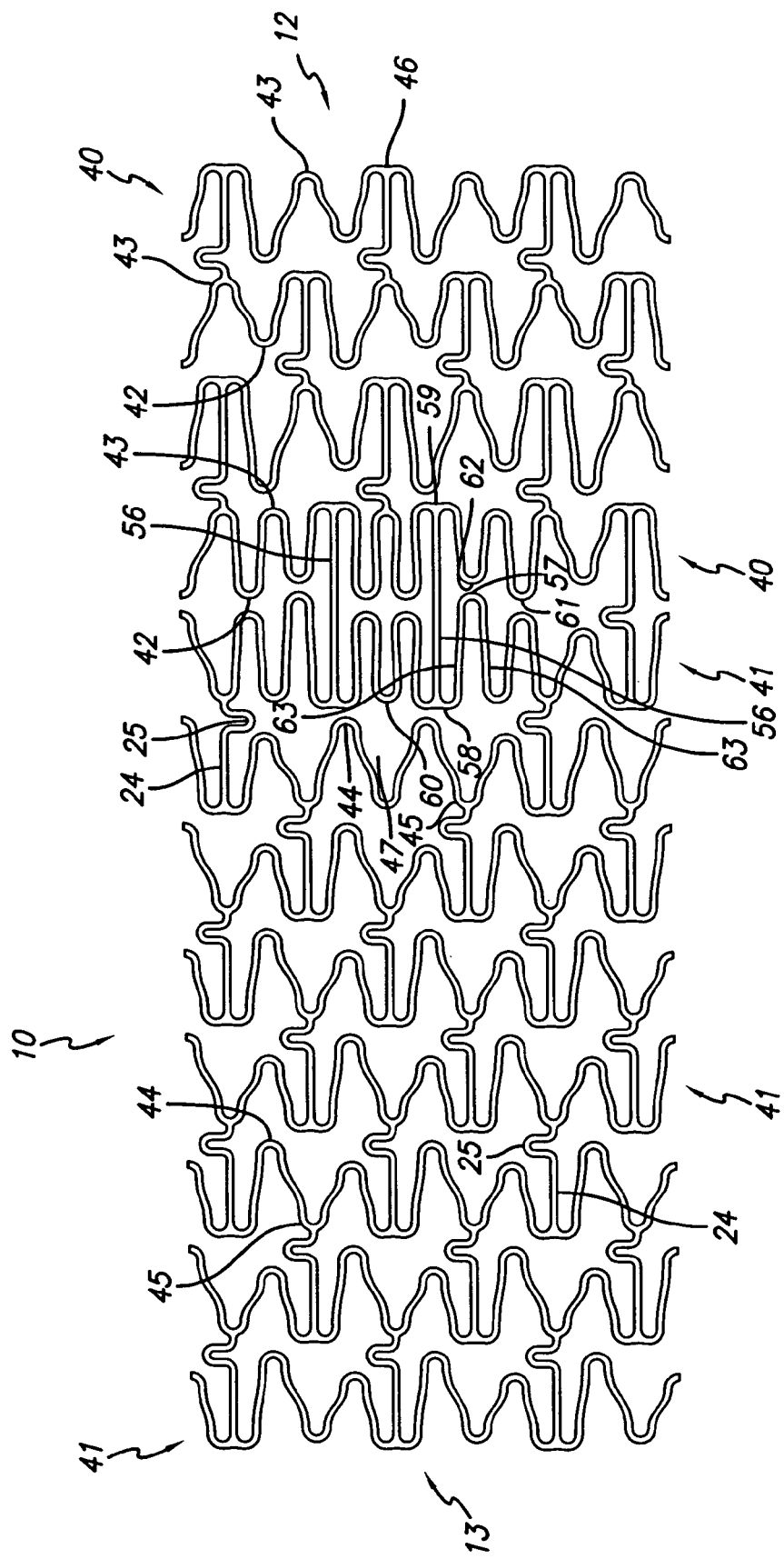
FIG. 11 is an elevational view of a stent in a flattened configuration depicting a bifurcated stent.

In another embodiment, as shown in FIG. 11, stent 10 is substantially the same as the stent depicted in FIG. 10 with two notable exceptions. First, linear links 56 connect the fourth ring (from the proximal end 12) to the No. 5 ring. Secondly, peak 57 extends in a proximal direction toward proximal end 12 since there is no longer an undulating portion from a non-linear link to interfere with peak 57 when the stent is compressed to its crimped state prior to deployment. By replacing the non-linear link in FIG. 10 with linear links 56 in FIG. 11, this increases the axial stiffness in the portal region 47 and the force that moves W-shaped member 58 and 59 apart is maximized. This also enhances protrusion of peak 60 and W-shaped member 58 into the opening of the side branch vessel. While some flexibility is sacrificed in delivery and deployment, the opening to the side branch vessel is adequately covered. By removing the undulating portion of linear links 56 which connect ring Nos. 4 and 5, additional space is created in the pattern. Moving peak 57 proximally toward the proximal end 12 allows the portal region 47 to open further due to the increased bar arm length 63. In this case, peak 57 has been moved proximally to extend beyond peak 61 so that ring Nos. 4 and 5 partially overlap, at least in this area. Peaks 57 and 62 can be adjusted in position to alter the opening characteristics of these rings by the portal region 47.

Figure 12:
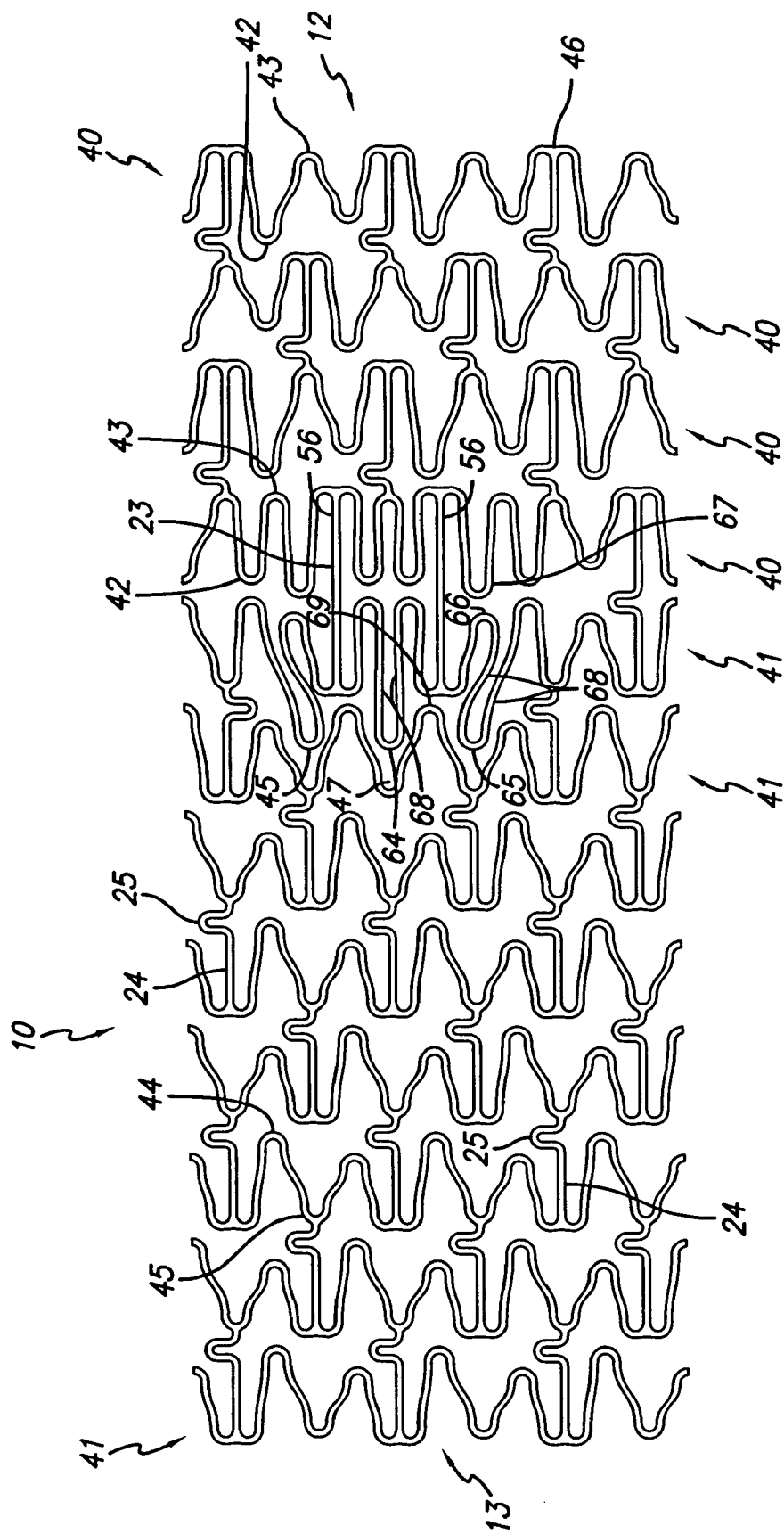
FIG. 12 is an elevational view of a stent in a flattened configuration in which the bar arms of some of the peaks and some of the links in the portal region are substantially longer relative to other embodiments.

In another embodiment, shown in FIG. 12, stent 10 is similar to the configuration and pattern of the stent of FIG. 11. In this embodiment, valley 64 and valley 65 as well as peaks 66 and 67 all have been moved distally toward distal end 13. Each of valleys 64/65 and peaks 66,67 have longer bar arms 68 which will move and extend ring Nos. 4 and 5 (counting from the proximal end 12) further into the opening to the side branch vessel. In this embodiment, ring Nos. 5 and 6 overlap at the portal region 47, however, this does not mean that the various valleys and peaks overlap or cross over each other. In other words, when the stent is mounted on the side branch balloon and the main vessel balloon, valley 64 is mounted on the side branch balloon while peak 69 is on the main vessel balloon which is under the side branch balloon, therefore there is no interference of overlap when the stent is in a crimped configuration. Further, peaks 66 and 67 have been moved toward each other which allows ring No. 4 to open further.

Figure 13:
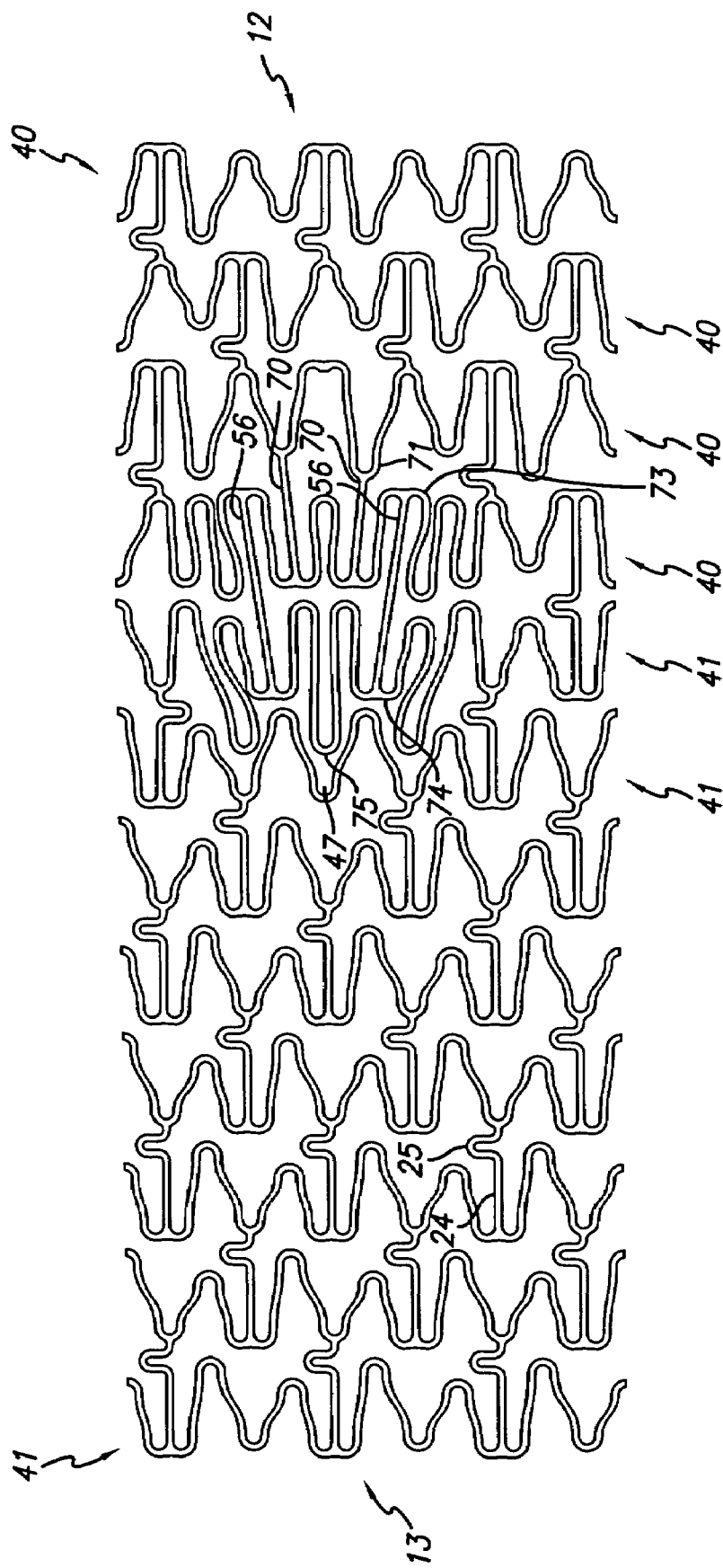
FIG. 13 is an elevational view of a stent in a flattened configuration in which the bar arms of some of the peaks and some of the links in the portal region are substantially longer relative to other embodiments.

In another embodiment, shown in FIG. 13, stent 10 is similar to the stent configuration of FIG. 12. In FIG. 13, linear links 70 connect ring No. 3 to ring No. 4 (counting from proximal end 12 to distal end 13), whereas in FIG. 12 these links were non-linear links having undulating portions. As a result, there is a larger reaction force from the expansion of ring 3 toward ring No. 4 so that point 71 on linear link 70 provides an anchor for point 72 in order to limit any proximal movement to proximal end 12. With point 72 now more stable, point 73 should move more distally toward distal end 13 when the stent is expanded. This movement also causes points 74 and 75 to move more into the opening of the side branch vessel, and even partially into the side branch vessel.

Figure 14:
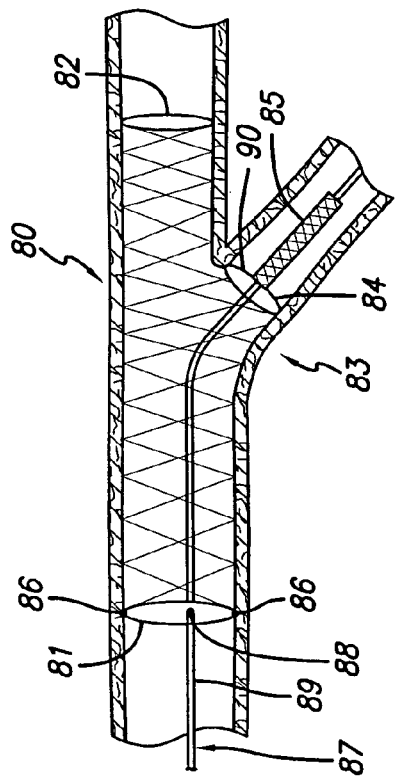
FIG. 14 is a schematic of a bifurcated stent implanted at a bifurcation and a second stent (or side branch stent) being delivered in the side branch vessel.

The present invention stent extends only into the ostium of the side branch vessel while the main body of the stent scaffolds the main branch vessel and the cornea of the bifurcation, but the stent provides no scaffolding into the side branch vessel. In order to stent the side branch vessel, a second stent is implanted so that the proximal end of the second stent abuts the distal end of the portal region of the bifurcated stent. Under fluoroscopy, it is often difficult to align the proximal end of the second stent with the distal end of the portal region of the bifurcated stent. Accordingly, in one embodiment of the present invention, radiopaque markers are positioned to assist in the alignment of the second stent in the side branch vessel so that it abuts the distal end of the portal region of the bifurcated stent and yet the struts of the two stents do not overlap or result in a gap between the stents. In one embodiment, as shown in FIG. 14, bifurcated stent 80 has a proximal end 81 and a distal end 82. A portal region 83 extends into the ostium of the side branch vessel, yet does not extend into the side branch vessel to provide scaffolding to the vessel. The portal region distal end 84 extends only into the ostium of the side branch vessel. In order to accurately deploy and implant second stent 85 in the side branch vessel, a pair of proximal radiopaque markers 86 are positioned approximately 180° apart on proximal end 81 of the bifurcated stent 80. The second stent 85 is delivered by delivery catheter 87 which has a radiopaque marker collar 88 positioned on the catheter shaft 89 of delivery catheter 87. After the bifurcated stent 80 has been implanted, delivery catheter 87 passes through the expanded bifurcated stent 80 so that the second stent 85 can be advanced through the portal region 83 and into the side branch vessel. During delivery of second stent 85 to the side branch vessel, the radiopaque marker collar 88 will come into alignment with the proximal radiopaque markers 86 positioned at the proximal end 81 of the bifurcated stent 80. When the radiopaque markers 86 and 88 come into alignment, the proximal end 90 of the second stent will be in alignment with the distal end 84 of the portal region 83. At that point, the second stent 85 can be expanded and implanted in the side branch vessel so that the proximal end 90 abuts the distal end 84 of the portal region 83.

Figure 15:
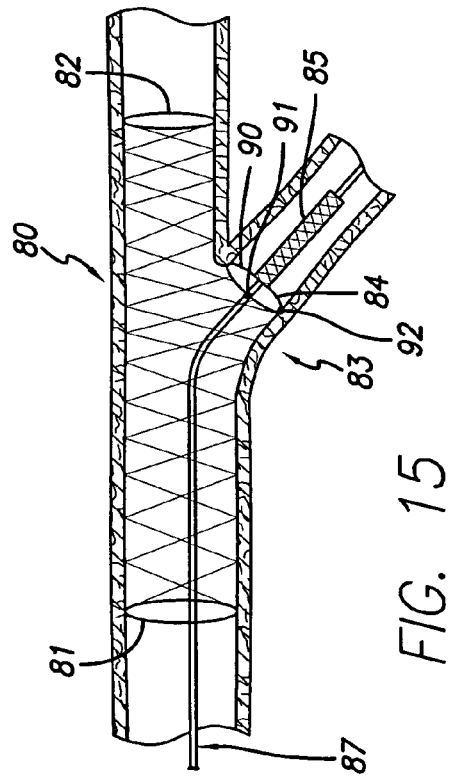
FIG. 15 is a schematic of a bifurcated stent implanted at a bifurcation and a second stent (or side branch stent) being delivered in the side branch vessel.
Figure 16:
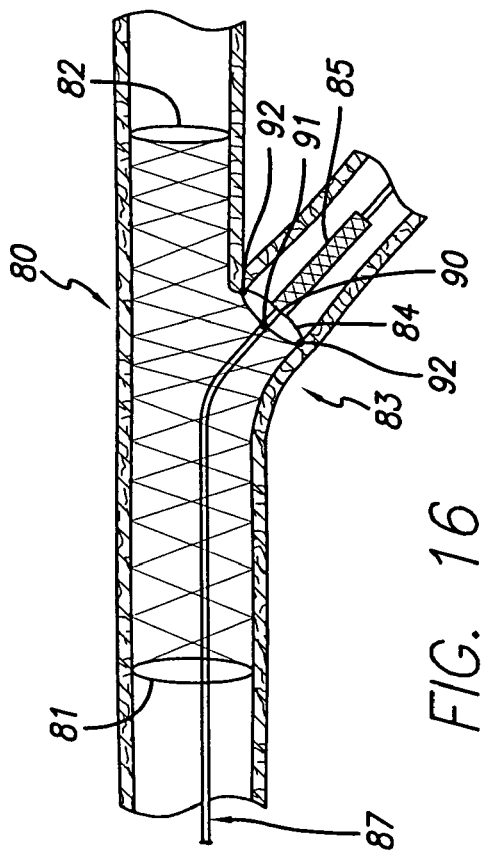
FIG. 16 is a schematic of a bifurcated stent implanted at a bifurcation and a second stent (or side branch stent) being delivered in the side branch vessel.

In another embodiment, as shown in FIG. 15, the bifurcated stent 80 has a proximal end 81 and a distal end 82 with portal region 83 extending into the ostium of the side branch vessel. The distal end 84 of the portal region 83 has a radiopaque marker 91 that is visible under fluoroscopy. In this embodiment, second stent 85 is delivered by delivery catheter 87 which has radiopaque marker collar 91 positioned just proximal of the proximal end 90 of the second stent 85. When the second stent 85 is being delivered to the side branch vessel, the radiopaque marker collar 91 comes into alignment with radiopaque marker 92 positioned at the distal end 84 of portal region 83. Once radiopaque markers 91 and 92 are aligned, the second stent 85 is properly positioned in the side branch vessel where it can be expanded and implanted. The proximal end 90 of the second stent 85 will abut the distal end 84 of the portal region 83. Similarly, as shown in FIG. 16, a second radiopaque marker 92 is positioned on the distal end 84 of portal region 83 to assist in aligning the second stent 85 in the side branch vessel. With two radiopaque markers 92, any errors due to parallax based on an angiographic view under fluoroscopy are eliminated.

Figure 17:
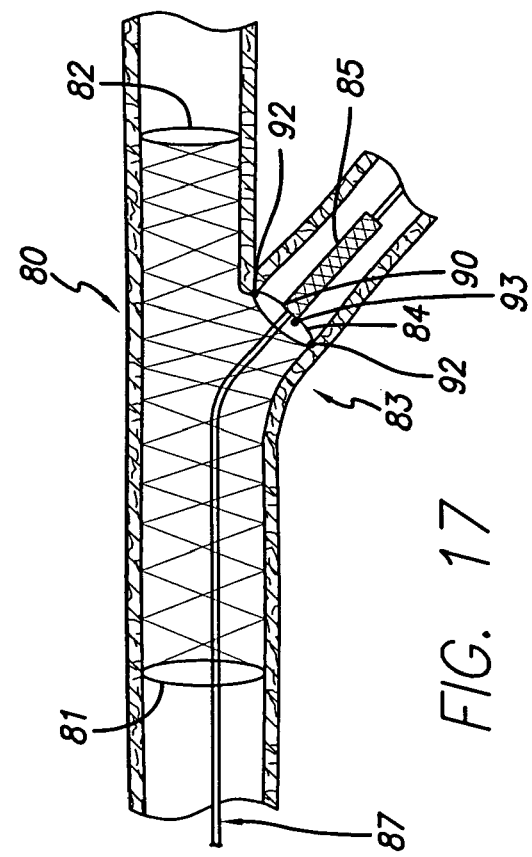
FIG. 17 is a schematic of a bifurcated stent implanted at a bifurcation and a second stent (or side branch stent) being delivered in the side branch vessel.
Figure 18E:
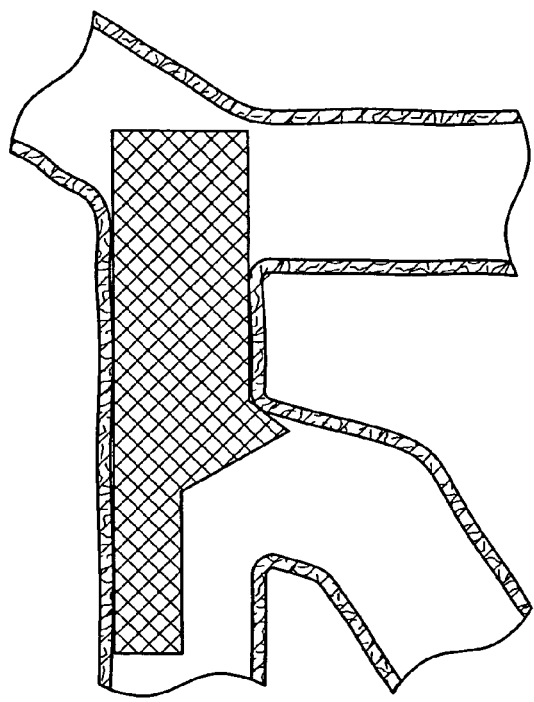
FIGS. 18E, 18F, 18G, and 18H show various embodiments of prior art stents for treating bifurcated vessels.
Figure 18F:
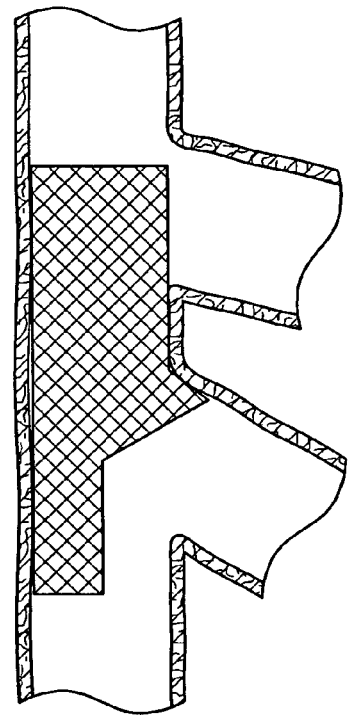
Figure 18G:
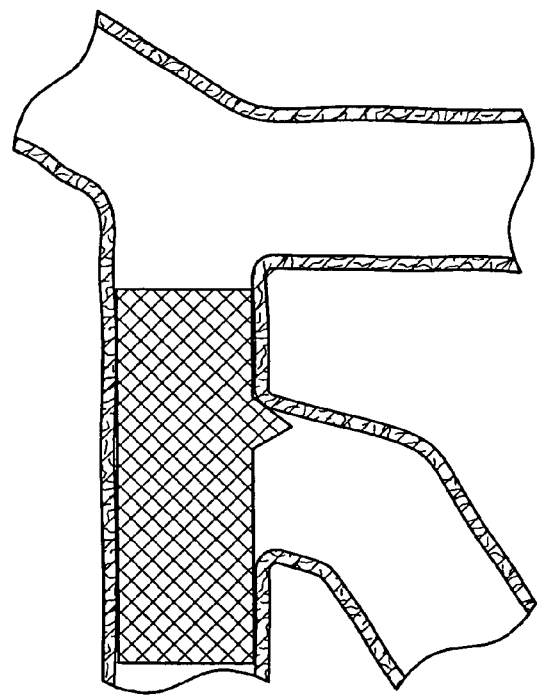
Figure 18H:
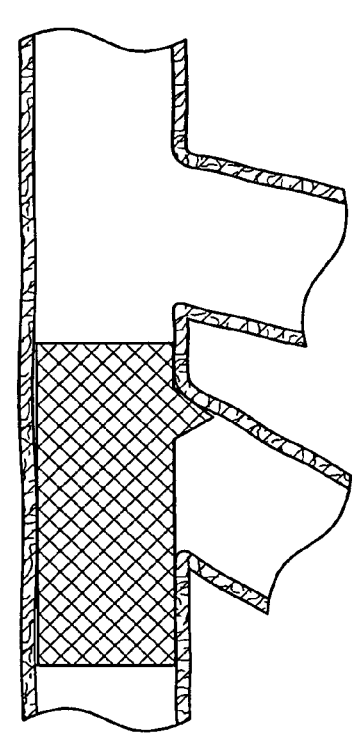
Figure 19:
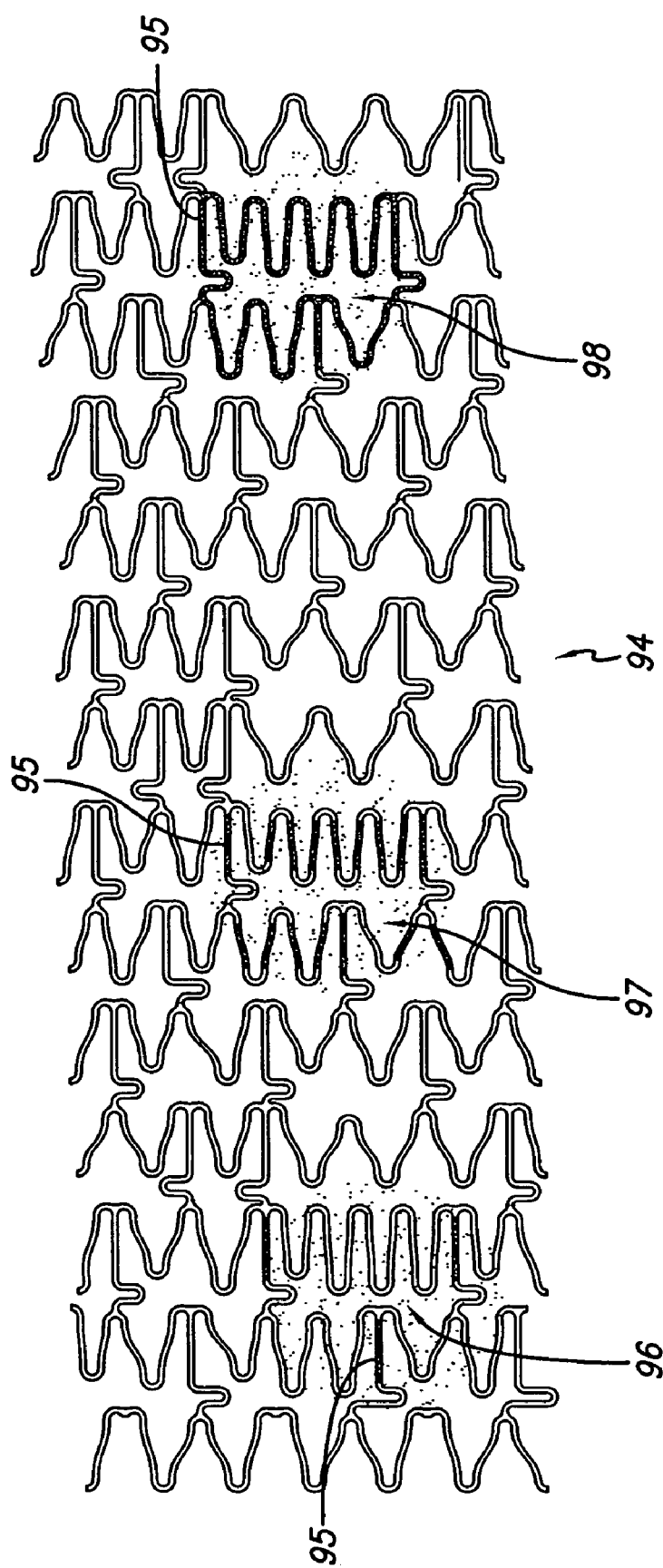
FIG. 19 is a schematic view of a bifurcated stent in a flattened configuration depicting radiopaque markers in the portal region.
Figure 20:
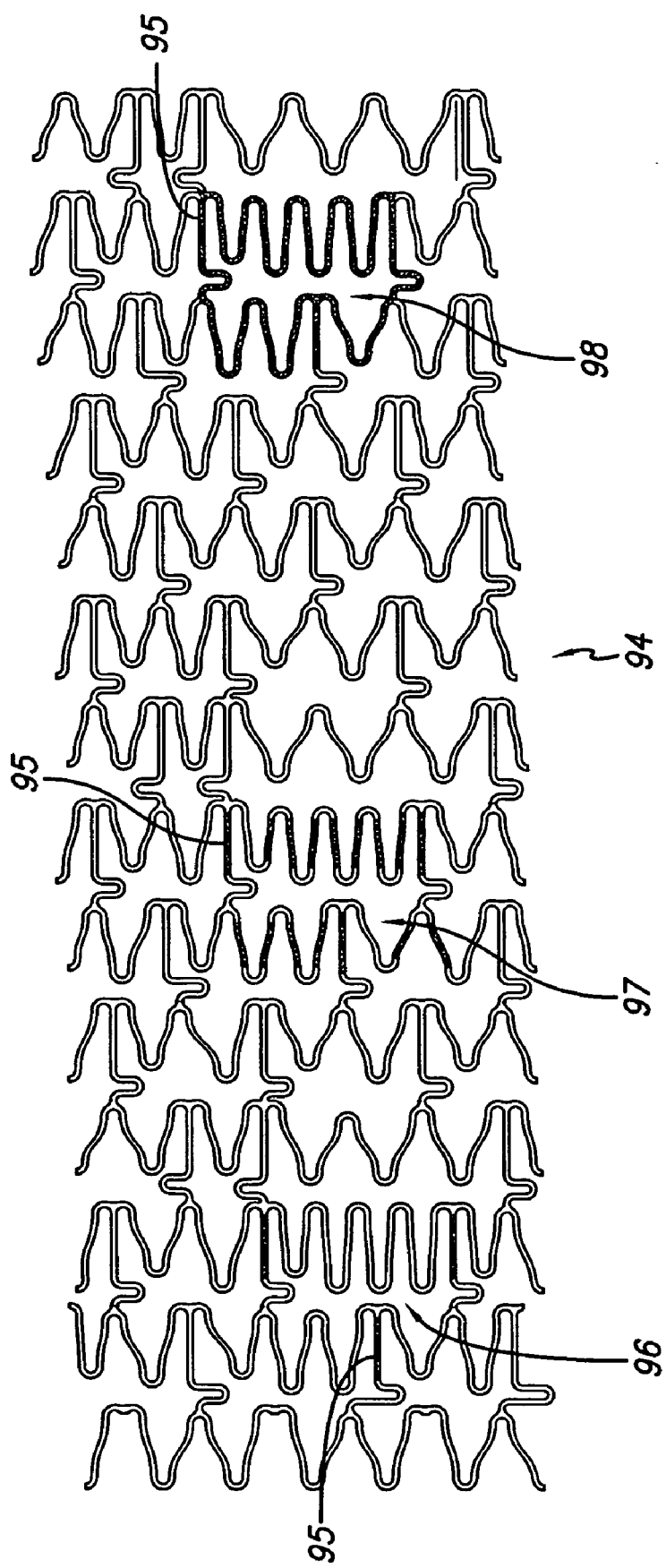
FIG. 20 is a schematic view of a bifurcated stent in a flattened configuration depicting radiopaque markers in the portal region.
Figure 21:
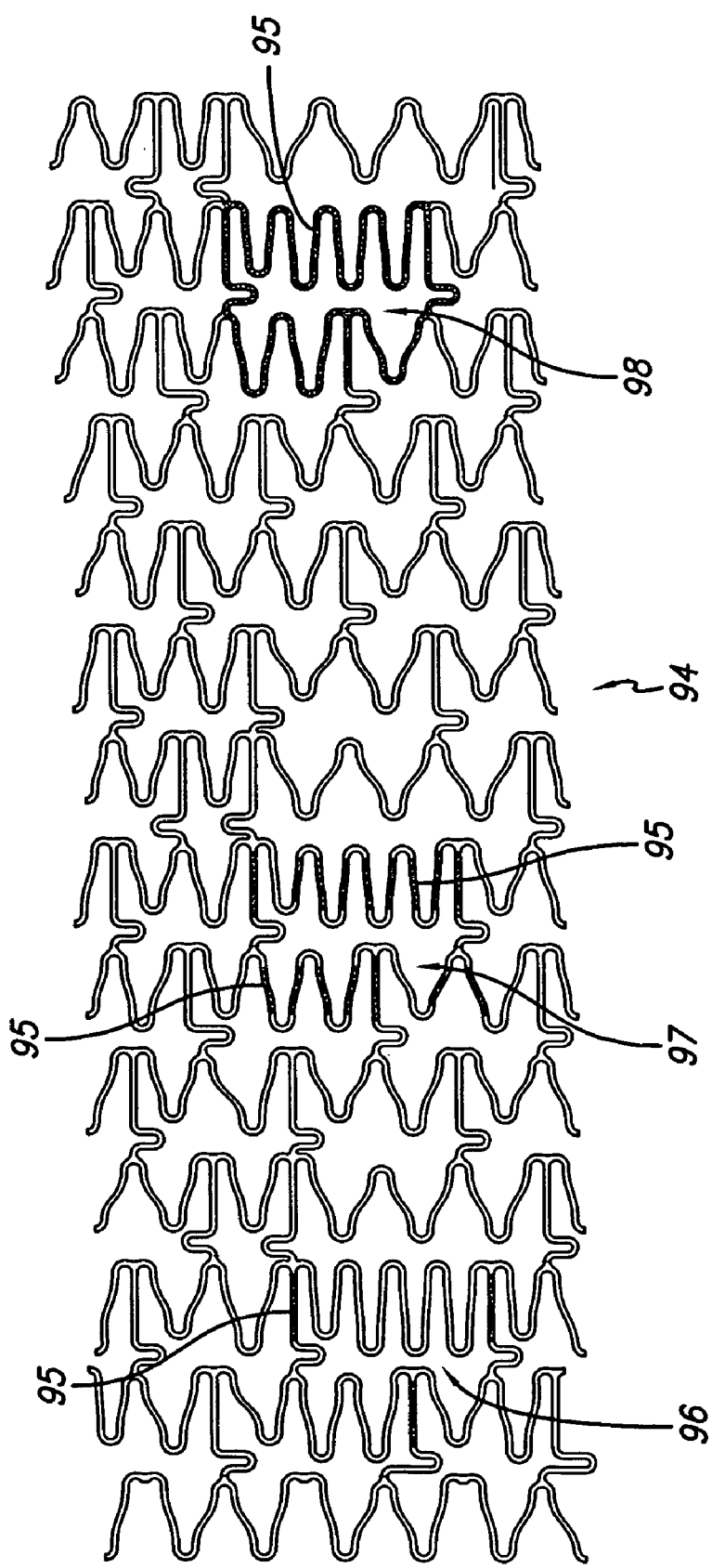
FIG. 21 is a schematic view of a bifurcated stent in a flattened configuration depicting radiopaque markers in the portal region.

In another embodiment used for aligning the side branch stent, as shown in FIG. 17, the bifurcated stent 80 has proximal end 81 and distal end 82 with a portal region 83 extending into the ostium of the side branch vessel. In this embodiment, radiopaque markers 92 are positioned on the distal end 84 of portal region 83. Second stent 85 has a radiopaque marker 93 on the proximal end 90 of the second stent 85. As the delivery catheter 87 advances the second stent 85 into the side branch vessel, the radiopaque marker 93 located on the proximal end 90 of the second stent 85 comes into alignment with the radiopaque markers 92 positioned on the distal end 84 of the portal region 83. At that point, the proximal end 90 of the second stent 85 is properly aligned with the distal end 84 of the portal region so that the second stent 85 can be expanded and implanted in the side branch vessel and the proximal end 90 of the second stent 85 will abut distal end 84 of the portal region 83.

In one aspect of the invention, plaque or lesions can accumulate at various locations in and around a bifurcated vessel. For example, in FIGS. 18A-18D, plaque or lesions are shown in black as representing areas where plaque can accumulate. Various prior art stents have been used to treat plaque in and around the bifurcated vessel with varying results. Often, the prior art stents are unable to fully cover the bifurcated vessel area to adequately scaffold the bifurcated vessel. In one embodiment of the present invention, as shown in FIGS. 18E, 18H, and 19-21, stent 94 has a number of radiopaque markers 95 that are positioned to identify a distal portal region 96, a mid-portal region 97, and a proximal portal region 98. In these embodiments, stent 94 can be customized to allow any of the distal, mid and proximal portal regions 96, 97, 98 to be used to align with and partially expand into the opening of the side branch vessel, depending upon the location of the side branch vessel relative to the main vessel, and the accumulation of plaque as previously described. Thus, and as will be hereinafter described, the balloon portion of a catheter extends through stent 94, and a second balloon extends through any of the distal portal region 96, mid-portal region 97, or proximal portal region 98. Typically, the physician would determine through fluoroscopic imaging the portal region that would best fit the anatomy of the patient based on the location of the bifurcated vessel, and the plaque or lesions to be treated. The radiopaque markers 95 on stent 94 will be visible under fluoroscopy or other imaging procedures in order to properly align any of the distal portal region 96, mid-portal region 97, or proximal portal region 98 with the opening to the side branch vessel of the bifurcation. Typically, radiopaque markers 95 can be platinum iridium, tungsten, or silver, and be coated onto the struts of stent 94 in a known manner.

Figure 22:
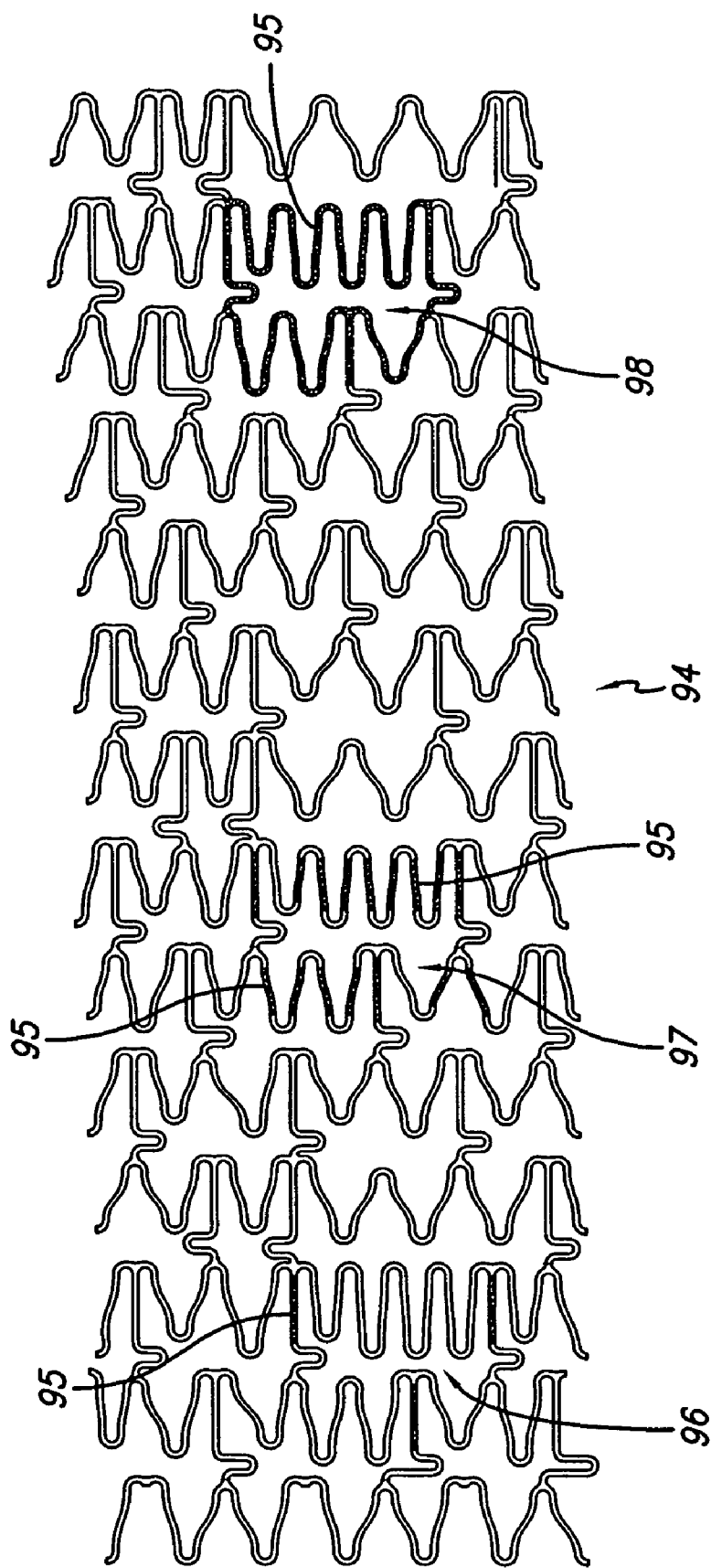
FIG. 22 is an elevational view of a stent in a flattened configuration depicting portions of a metallic stent covered with a tungsten loaded polymer to increase radiopacity.
Figure 30:
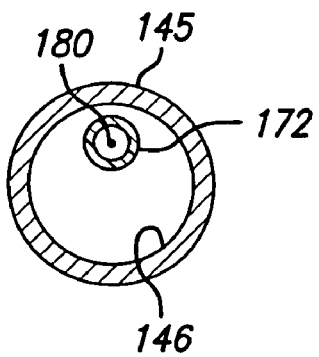
FIG. 30 is a transverse cross-sectional view taken along lines 30-30 depicting the proximal shaft section of the catheter.
Figure 31:
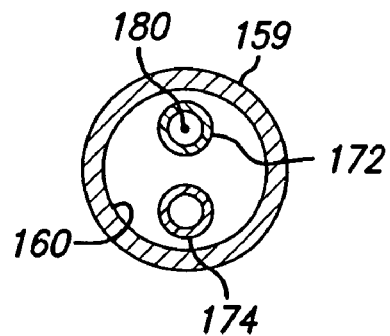
FIG. 31 is a transverse cross-sectional view taken along lines 31-31 depicting the mid- or intermediate shaft section of the catheter.
Figure 31A:
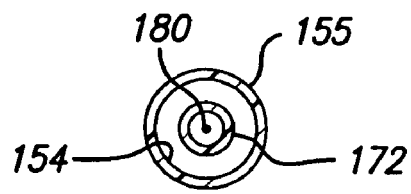
FIG. 31A is a transverse cross-sectional view taken along lines 31A-31A depicting the first distal outer member.
Figure 31B:
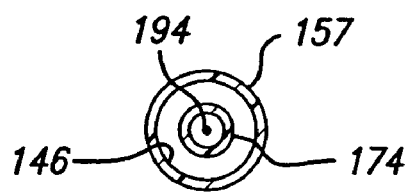
FIG. 31B is a transverse cross-sectional view taken along lines 31B-31B depicting the second distal outer member.
Figure 32:
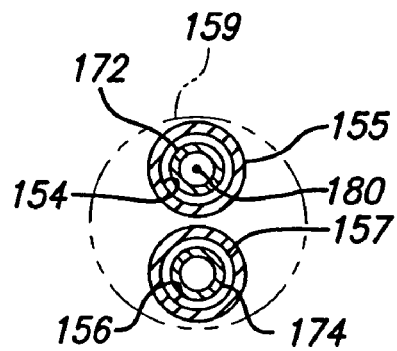
FIG. 32 is a transverse cross-sectional view taken along lines 32-32 depicting the multifurcated distal section of the catheter.
Figure 34:
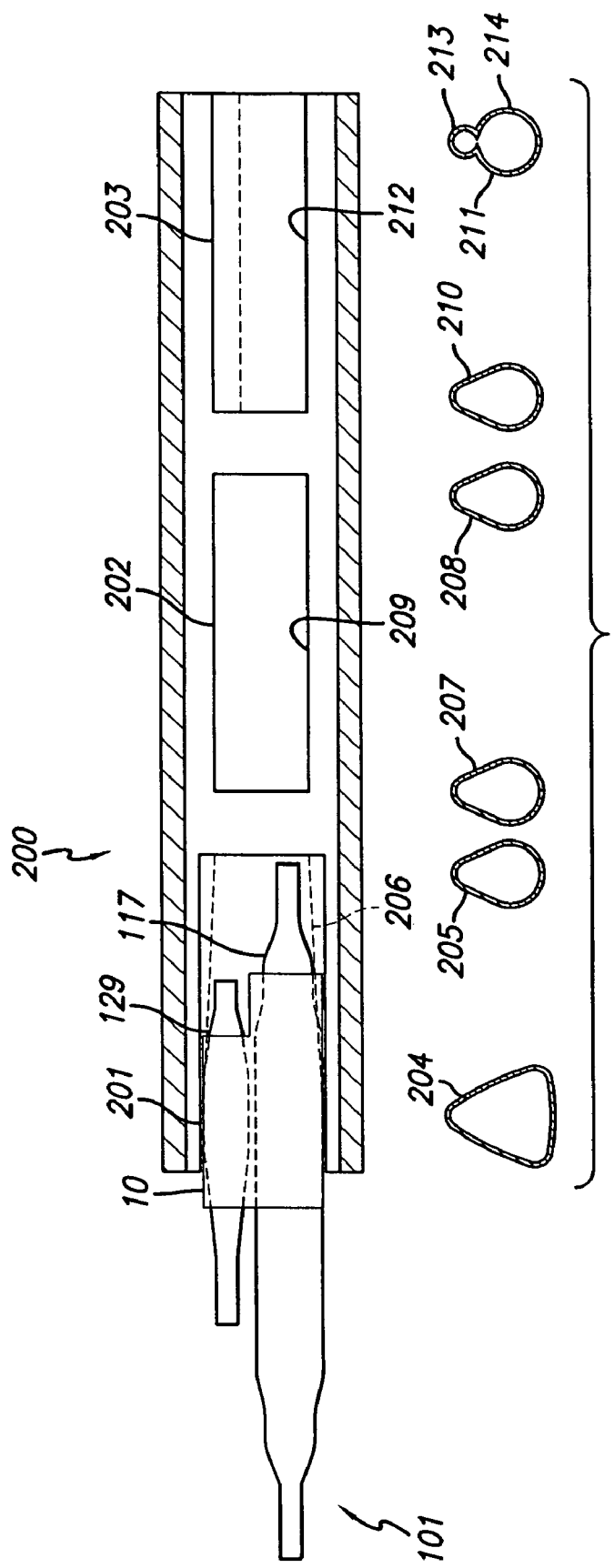
FIG. 34 is an elevational view and a partial longitudinal cross-sectional view of the crimping mold assembly.

The radiopaque markers 95 of stent 94 can be formed in numerous ways in order to identify the portal regions on the stent. For example, as shown in FIG. 22, a high percentage tungsten material is loaded into a polymer to form a polymer coating which is then applied to the struts of the stents to form radiopaque markers 95. A high percentage, typically greater than 60% tungsten, is loaded into a polymer such as PEBAX, which is then formed or coated onto the struts to form the radiopaque markers. The tungsten loaded polymers must be able to expand so that as the stent is expanded, there is no adverse effect on the ability of the stent to expand or an adverse affect on the integrity of the coating. Other metals can be used in place of tungsten to be loaded into the polymer, such as platinum, platinum iridium, and silver.

Each embodiment of the stent 10 also can have rings 16 and links 18 that have variable thickness struts, at various points in order to increase the radial strength of the stent, provide higher radiopacity so that the stent is more visible under fluoroscopy, and enhance flexibility in the portions where the stent has the thinnest struts. The stent also can have variable width struts to vary flexibility, maximize vessel wall coverage at specific points, or to enhance the stent radiopacity. The variable thickness struts or variable width struts, which may be more radiopaque than other struts, can be positioned along the stent to help the physician position the stent during delivery and implantation in the bifurcated vessel.

The stent 10 can be formed in a conventional manner typically by laser cutting a tubular member or by laser cutting a pattern into a flat sheet, rolling it into a cylindrical body, and laser welding a longitudinal seam along the longitudinal edges of the stent. The stent can also be fabricated using conventional lithographic and etching techniques where a mask is applied to a tube or flat sheet. The mask is in the shape of the final stent pattern and is used for the purpose of protecting the tubing during a chemical etching process which removes material from unwanted areas. Electro-discharge machining (EDM) can also be used for fabricating the stent, where a mold is made in the negative shape of the stent and is used to remove unwanted material by use of an electric discharge. The method of making stents using laser cutting processes or the other described processes are well known. The stent of the invention typically is made from a metal alloy and includes any of stainless steel, titanium, nickel-titanium (NiTi or nitinol of the shape memory or superelastic types), tantalum, cobalt-chromium, cobalt-chromium-vanadium, cobalt-chromium-tungsten, gold, silver, platinum, platinum-iridium or any combination of the foregoing metals and metal alloys. Any of the listed metals and metal alloys can be coated with a polymer containing fluorine-19 (19F) used as a marker which is visible under MRI. Portions of the stent, for example some of the links, can be formed of a polymer impregnated with 19F so that the stent is visible under MRI. Other compounds also are known in the art to be visible under MRI and also can be used in combination with the disclosed metal stent of the invention.

The stent of the invention also can be coated with a drug or therapeutic agent to assist in repair of the bifurcated vessel and may be useful, for example, in reducing the likelihood of the development of restenosis. Further, it is well known that the stent (usually made from a metal) may require a primer material coating to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Examples of therapeutic agents that are available as stent coatings include rapamycin, ererolimus clobetasol, actinomycin D (ActD), or derivatives and analogs thereof. ActD is manufactured by Sigma-Aldrich, 1001 West Saint Paul Avenue, Milwaukee, Wis. 53233, or COSMEGEN, available from Merck. Synonyms of actinopmycin D include dactinomycin, actinomycin IV, actinomycin 11, actinomycin X1, and actinomycin C1. Examples of agents include other antiproliferative substances as well as antineoplastic, antiinflammatory, antiplatelet, anticoagulant, antifibrin, antithomobin, antimitotic, antibiotic, and antioxidant substances. Examples of antineoplastics include taxol (paclitaxel and docetaxel). Examples of antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein, llb/llla platelet membrane receptor antagonist, recombinant hirudin, thrombin inhibitor (available from Biogen), and 7E-3B® (an antiplatelet drug from Centocore). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as Captopril (available from Squibb), Cilazapril (available from Hoffman-LaRoche), or Lisinopril (available from Merck); calcium channel blockers (such as Nifedipine), colchicine fibroblast growth factor (FGF) antagonists, fish oil (omega 3-fatty acid), histamine antagonist, Lovastatin (an inhibitor of HMG-CoA reductase, a cholesterol lowering drug from Merck), monoclonal antibodies (such as PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

It should be understood that any reference in the specification or claims to a drug or therapeutic agent being coated on the stent is meant that one or more layers can be coated either directly on the stent or onto a primer material on the stent to which the drug or therapeutic agent readily attaches.

The Stent Delivery Catheter Assembly

Any of the stents of the present invention can be delivered by any of the catheter assemblies disclosed herein. As shown in FIGS. 23-28A, the stent 10 is mounted on catheter assembly 101 which has a distal end 102 and a proximal end 103. The catheter assembly includes a proximal shaft 104 which has a proximal shaft over-the-wire (OTW) guide wire lumen 105 and a proximal shaft inflation lumen 106 which extends therethrough. The proximal shaft OTW guide wire lumen is sized for slidably receiving an OTW guide wire. The inflation lumen extends from the catheter assembly proximal end where an indeflator or similar device is attached in order to inject inflation fluid to expand balloons or expandable members as will be herein described. The catheter assembly also includes a mid-shaft 107 having a mid-shaft OTW guide wire lumen 108 and a mid-shaft rapid-exchange (Rx) guide wire lumen 109. The proximal shaft OTW guide wire lumen 105 is in alignment with and an extension of the mid-shaft OTW guide wire lumen 108 for slidably receiving an OTW guide wire. The mid-shaft also includes a mid-shaft inflation lumen 110 which is in fluid communication with the proximal shaft inflation lumen 106 for the purpose of providing inflation fluid to the expandable balloons. There is an Rx proximal port or exit notch 115 positioned on the mid-shaft such that the Rx proximal port is substantially closer to the distal end 102 of the catheter assembly than to the proximal end 103 of the catheter assembly. While the location of the Rx proximal port may vary for a particular application, typically the port would be between 10 and 50 cm from the catheter assembly distal end 102. The Rx proximal port or exit notch 115 provides an opening through which an Rx guide wire 116 exits the catheter and which provides the rapid exchange feature characteristic of such Rx catheters. The Rx port 115 enters the mid-shaft such that it is in communication with the mid-shaft Rx guide wire lumen 109.

The catheter assembly 101 also includes a distal Rx shaft 111 that extends from the distal end of the mid-shaft and which includes an Rx shaft Rx guide wire lumen 112, to the proximal end of the inner member 111A inside balloon 117. The distal Rx shaft 111 also contains an Rx shaft inflation lumen 114. The Rx shaft Rx guide wire lumen 112 is in alignment with the Rx guide wire lumen 109 for the purposes of slidably carrying the Rx guide wire 116. The Rx shaft inflation lumen 114 is in fluid communication with the mid-shaft inflation lumen 110 for the purposes of carrying inflation fluid to the long expandable member or long balloon.

The catheter assembly also contains an Rx inner member 111A that extends from the distal end of the distal Rx shaft 111 to the Rx shaft distal port 113. The Rx inner member 111A contains an Rx guide wire lumen 111B. The Rx inner member guide wire lumen 111B is in alignment with the Rx shaft Rx guide wire lumen 112 for the purpose of slidably carrying the Rx guide wire 116. The Rx guide wire will extend through the Rx proximal port 115 and be carried through Rx guide wire lumen 109 and Rx shaft Rx guide wire lumen 112, and through Rx guide wire lumen 111B and exit the distal end of the catheter assembly at Rx shaft distal port 113.

The catheter assembly further includes a long balloon 117 positioned adjacent the distal end of the catheter assembly and a distal tip 118 at the distal end of the Rx shaft. Further, a coupler 119 is associated with distal Rx shaft 111 such that the Rx shaft Rx guide wire lumen 112 extends through the coupler, with the distal port 113 being positioned at the distal end of the coupler. The coupler has an Rx guide wire lumen 120 that is an extension of and in alignment with Rx lumen 111B. The coupler 119 further includes a blind lumen 121 for receiving and carrying an OTW guide wire (or joining mandrel) 125. The blind lumen includes a blind lumen port 122 for receiving the distal end of the OTW guide wire (or joining mandrel) 125 and a dead-end lumen 124 positioned at the coupler distal end 123. The coupler blind lumen 121 will carry the distal end of a guide wire (either the distal end of the OTW guide wire (or joining mandrel) 125 or an Rx guide wire (or joining mandrel) 116 as will be further described herein) during delivery of the catheter assembly through the vascular system and to the area of a bifurcation. The blind lumen is approximately 3 to 20 mm long, however, the blind lumen can vary in length and diameter to achieve a particular application or to accommodate different sized guide wires having different diameters. Since the coupler moves axially relative to the shaft it is not connected to, the guide wire that resides in the blind lumen 121 of the coupler slides axially relative to the coupler during delivery of the catheter assembly through the vascular system and tortuous anatomy so that, additional flexibility is imported to the tips making it easier to track through tortuous circuitry. A distance "A" should be maintained between the distal end 126 of the OTW guide wire 125 and the dead end 124 of the blind lumen. The distance "A" can range from approximately 0.5 to 5.0 mm, however, this range may vary to suit a particular application. Preferably, distance "A" should be about 0.5 mm to about 2.0 mm.

The catheter assembly 101 also includes an OTW shaft 128 which extends from the distal end of mid-shaft 107. The OTW shaft carries a short balloon 129 that is intended to be shorter than long balloon 117 and positioned substantially adjacent to the long balloon. The OTW shaft 128 also includes an OTW lumen 130 that is in alignment with the mid-shaft OTW guide wire lumen 108 and proximal shaft OTW guide wire lumen 105. Thus, an OTW lumen extends from one end of the catheter assembly to the other and extends through the OTW shaft 128. An OTW shaft distal port 131 is at the distal end of the OTW lumen 130 and the OTW shaft 128 also includes an OTW shaft inflation lumen 132. Inflation lumen 132 is in alignment and fluid communication with inflation lumens 110 and 106 for the purpose of providing inflation fluid to the long balloon 117 and the short balloon 129. In this particular embodiment, an OTW guide wire 125 would extend from the proximal end 103 of the catheter assembly and through proximal shaft OTW guide wire lumen 105, mid-shaft OTW guide wire lumen 108, OTW lumen 130 and out distal port 131 where it would extend into the coupler 119, and more specifically into blind lumen 121 through blind lumen port 122.

In order for the catheter assembly 101 to smoothly track and advance through tortuous vessels, it is preferred that the OTW lumen 130 be substantially aligned with the blind lumen 121 of coupler 119. In other words, as the OTW guide wire extends out of the OTW lumen 130, it should be aligned without bending more than about ±10° so that it extends fairly straight into the coupler blind lumen 121. If the OTW lumen 120 and the coupler blind lumen 121 are not substantially aligned, the pushability and the trackability of the distal end of the catheter assembly may be compromised and the physician may feel resistance as the catheter assembly is advanced through tortuous vessels, such as the coronary arteries.

In an alternative embodiment, as will be explained more fully herein, a mandrel (stainless steel or nickel titanium wire is preferred) resides in the OTW guide wire lumens 105, 108, 130, and extends into blind lumen 121. The mandrel is used in place of an OTW guide wire until the catheter assembly has been positioned near the bifurcated vessel, at which time the mandrel can be withdrawn from the vascular system and the OTW guide wire advanced through the OTW guide wire lumens to gain access to the side branch vessel. This will be described more fully in the section related to delivering and implanting the stent.

The catheter assembly 101 of the present invention can be dimensioned for various applications in a patient's vascular system. Such dimensions typically are well known in the art and can vary, for example, for various vessels being treated such as the coronary arteries, peripheral arteries, the carotid arteries, and the like. By way of example, the overall length of the catheter assembly for treating the coronary arteries typically is approximately 135 to 150 cm. Further, for stent delivery in the coronary arteries at a bifurcated vessel, the working surface or the stent carrying surface of the long balloon 117 can be about 18.5 mm for use with an 18 mm-long stent. The short balloon 129 typically will be about 6 to 9 mm, depending on the type of trap door stent 20 that is being implanted. The lengths of the various shafts, including proximal shaft 104, mid-shaft 107, distal Rx shaft 111, and OTW shaft 128 are a matter of choice and can be varied to suit a particular application.

As shown in FIG. 28A, radiopaque markers 135 are placed on the catheter assembly to help the physician identify the location of the distal end of the catheter in relation to the target area for stent implantation. While the location of the radiopaque markers is a matter of choice, preferably the long balloon 117 will have three radiopaque markers on the inner shaft of the guide wire lumen 112 and the short balloon 129 will have one radiopaque marker on the inner member of the OTW guide wire lumen 130. Preferably, the middle radiopaque marker on the inner shaft of the long balloon is aligned with the opening of the trap door. One or more of the radiopaque markers may coincide with the alignment of the stent on the balloons which will be described more fully herein.

FIG. 29 illustrates another embodiment of a bifurcated catheter 140 which embodies features of the invention. As with catheter 101, the bifurcated catheter 140 can be used for a variety of procedures such as dilatation, drug delivery, and delivering and deploying a stent, including a stent of the invention, in a body lumen. Bifurcated catheter 140 generally comprises an elongated shaft 142 having a proximal shaft section 144 with a first inflation lumen 146, and a multifurcated distal shaft section 148 with a first branch 150 and at least a second branch 152. The first branch 150 has a second inflation lumen 154 within at least a portion thereof in fluid communication with the first inflation lumen 146 and the second branch 152 has a third inflation lumen 156 within at least a portion thereof in fluid communication with the first inflation lumen 146. An intermediate shaft section 158 joins the proximal and distal sections together and defines a fourth inflation lumen 160 in fluid communication with the first, second, and third inflation lumens 146/154/156. A joining wire lumen 162 extends within the proximal section, the intermediate section, and the first branch 150 of the multifurcated distal section 148. The guide wire lumen 164 extends within the intermediate section 158 and the second branch 152 of the multifurcated distal section 148. A guide wire lumen 164 extends within the intermediate section 158 and the second branch 152 of the multifurcated distal section 148. A first balloon 166 is on the first branch 150 and a second balloon 168 is on the second branch 152, with interiors in fluid communication with the inflation lumens. An adapter 169 on the proximal end of the catheter is configured to direct inflation fluid into the inflation lumens and to provide access to joining wire lumen 162. A coupler 170 on the second branch, distal to the second balloon 168, is configured for releasably coupling the first and second branches 150/152 together to form a coupled configuration, as discussed in more detail below. The bifurcated catheter 140 is illustrated in the coupled configuration in FIG. 29.

In the embodiment illustrated in FIG. 29, the joining wire lumen 162 is defined by a first inner tubular member 172, and the guide wire lumen 164 is defined by a second inner tubular member 174. In a presently preferred embodiment, the first inner tubular member 172 is formed of a single tubular member, which may comprise one or more layers as is conventionally known in the art. However, in alternative embodiments, the first inner tubular member 172 may be formed of separate longitudinal members joined together, end to end, along the length of the first inner tubular member 172. Similarly, the second inner tubular member 174 is preferably a single or multi-layered, single tubular member, although a plurality of separate members may be joined together to form the second inner tubular member 174.

The present invention provides a radiopaque marker for use on a variety of devices that is flexible, highly radiopaque and is easily attachable to such devices by melt bonding. These properties allow markers to be of minimal thickness and thereby minimize the effect the marker has on the overall profile and stiffness of the device to which it is to be attached.

In order to achieve the high fill ratios that are necessary to attain the desired radiopacity and in order to do so without compromising the compoundability and workability of the polymeric material nor its ultimate strength and flexibility, a number of different parameters have been found to be of importance. More specifically, both the particle shape and particle size of the radiopaque agent must be carefully controlled while the inclusion of a wetting agent such as MA-g-PO in the polymer blend is critical. An antioxidant may additionally be included in an effort to reduce the adverse effect the high processing temperatures and shear stresses may have on polymer properties.

A number of polymeric materials are well suited for use in the manufacture of the markers of the present invention. The material preferably comprises a low durometer polymer in order to render the marker sufficiently flexible so as not to impair the flexibility of the underlying medical device component to which the finished marker is to be attached. Additionally, in one embodiment, the polymer is preferably compatible with the polymeric material of which the component is constructed so as to allow the marker to be melt bonded in place. For example, in one embodiment, the polymeric marker and at least an outer layer of the catheter shaft are formed of the same class of the polymers (e.g., polyamides) so that they are melt bondable together. In another embodiment, the polymeric markers are installed on a dissimilar class of polymeric substrate, and are retained in position by adhesion or dimensional interference. The polymer must also impart sufficient strength and ductility to the marker compound so as to facilitate its extrusion and forming into a marker, its subsequent handling and attachment to a medical device and preservation of the marker's integrity as the medical device is flexed and manipulated during use. Examples of such polymers include but are not limited to polyamide copolymers like Pebax, polyetherurethanes like Pellethane, polyester copolymers like Hytrel, olefin derived copolymers, natural and synthetic rubbers like silicone and Santoprene, thermoplastic elastomers like Kraton and specialty polymers like EVA and ionomers, etc. as well as alloys thereof. A Shore durometer of not greater than about 63D to about 25D is preferred. The preferred polymer for use in the manufacture of a marker in accordance with the present invention is polyether block polyamide copolymer (PEBAX), with a Shore durometer of about 40D. However, other classes of polymers allowing for lower durometers may be used in the radiopaque markers, such as polyurethanes, which may provide greater flexibility.

A number of different metals are well known to be radiographically dense and can be used in a pure or alloyed form to mark medical devices so as to render them visible under fluoroscopic inspection. Commonly used metals include but are not limited to platinum, gold, iridium, palladium, rhenium and rhodium. Less expensive radiopaque agents include tungsten, tantalum, silver and tin, of which tungsten is most preferred for use in the markers of the present invention.

The control of particle size has been found to be of critical importance for achieving the desired ultra high fill ratios. While efforts to increase fill ratios have previously utilized small average particle sizes (1 micron or less) so as to minimize the ratio of particle size to as-extruded wall thickness, it has been found that higher fill percentages can be realized with the use of somewhat larger average particles sizes. It is desirable in the formulation of high fill ratio compounds to have the following attribute: 1) uniform distribution of the filler particles, and 2) continuity of the surrounding polymer matrix, and 3) sufficient spacing between filler particles so that the polymer matrix provides ductility to the bulk mixture to impart processability in both the solid and molten state.

The use of larger average particle sizes results in greater spacing between filler particles at a given percentage, thus maintaining processability during compounding and especially subsequent extrusion coating. The upper limit of average particle size is determined by the wall thickness of the coating and the degree of non-uniformity tolerable (i.e., surface defects). It has been found that a particle size distribution having an average particle size range of at least 2 microns to 10 microns and a maximum particle size of about 20 microns yields the desired fill ratio and provides for a smooth surface in the marker made therefrom.

The control of particle shape has also been found to be of critical importance for achieving the desired ultra high fill ratios. Discrete particles of equiaxed shape have been found to be especially effective, as individual particles of irregular shape, including agglomerations of multiple particles, have been found to adversely impact the surface, and thus, the maximum fill ratio that is attainable.

It has also been found that the process by which certain metal powders are produced has a profound effect on the shape of the individual particles. In the case of metallic tungsten, the powders may be formed by the reduction of powdered oxides through either "rotary," "pusher" or "atomization" processing. Of these processes, "rotary" processing has been found to yield the least desirable shape and size distribution as partial sintering causes coarse agglomerates to be formed which do not break up during compounding or extrusion and thus adversely effect the marker manufactured therefrom. Atomized powders have been reprocessed by melting and resolidifying "rotary" or "pusher" processed powders and result in generally equiaxed, discrete particles which are suitable for use in the present invention. "Pusher" processed powders are preferred due to their low cost and discrete, uniformly shaped particles.

In order for the polymer to most effectively encapsulate individual radiopaque particles, it is necessary for a low-energy interface to exist between such particles and the polymer so as to enable the polymer to "wet" the surface of the particles. The materials should have similar surface energies to be compatible. For materials which do not naturally have similar surface energies, compatibility can be promoted by generating a similar surface energy interface, i.e., a surface energy interface which is intermediate between the natural surface energies of the materials. Certain additives such as surfactants and coupling agents may serve as wetting agents and adhesion promoters for polymer/metal combinations that are not naturally compatible. It has been found that additives containing maleic anhydride grafted to a polyolefin backbone provide a significant benefit in this regard wherein materials commercially available as Lotader 8200 (having LLDPE Backbone) and Licomont AR504 (having PP backbone) were found to be particularly effective for use with tungsten/Pebax combinations. Emerging extrusions were found to be less susceptible to breakage, and the melt viscosity during compounding was lower as was manifested by a reduction in torque exerted during the extrusion process. The use of such additives allowed compounds with higher fill ratios to be successfully produced.

The inclusion of an antioxidant in the marker composition has also been found to be of benefit. Commercially available antioxidants such as Irganox B225 or Irganox 1010, have been found to minimize degradation (i.e., reduction in molecular weight) of the polymer matrix as it is exposed to the multiple heat and shear histories associated with the compounding, extrusion, and bonding processes.

The compound used for the manufacture of the marker of the present invention is preferably made by first blending the polymer resin and wetting agent, and optionally, an antioxidant such as by tumble mixing after which such blend is introduced into a twin-screw extruder via a primary feeder. The feed rate is carefully controlled in terms of mass flow rate to ensure that a precise fill ratio is achieved upon subsequent combination with the radiopaque agent. The heat that the materials are subjected as they are conveyed through the extruder causes the polymer to melt to thereby facilitate thorough homogenization of all of the ingredients. The radiopaque agent powder, selected for its uniform particle shape and controlled particle size distribution as described above is subsequently introduced into the melt stream via a secondary feeder, again at a carefully controlled mass flow rate so as to achieve the target fill ratio. The solid powder, molten polymer and additives are homogenized as they are conveyed downstream and discharged through a die as molten strands which are cooled in water and subsequently pelletized. The preferred extrusion equipment employs two independent feeders as introduction of all components through a single primary feeder would require significantly higher machine torques and result in excessive screw and barrel wear. The powder feeder is preferentially operated in tandem with a sidefeeder device, which in turn conveys the powder through a sealed main barrel port directly into the melt stream. A preferred composition comprises a fill ratio of at least 90.8 weight percent of tungsten (H.C. Starck's Kulite HC600s, HC180s and KMP-103JP) to Pebax 40D. A maleic anhydride source in the form of Licomont AR504 is initially added to the polymer resin at the rate of approximately 3 pphr while an antioxidant in the form of Ciba Geigy Irganox B225 at the rate of approximately 2 pphr (parts per hundred relative to the resin). The temperature to which materials are subjected to in the extruder is about 221° C.

Once the marker material has been compounded, the marker can be fabricated in suitable dimensions by an extrusion coating process. While free extrusion is possible, this method is problematic due to the high fill ratios of the polymeric materials. Extrusion onto a continuous length of beading has been found to lend the necessary support for the molten extrudate to prevent breakage. The support beading may take the form of a disposable, round mandrel made of PTFE (Teflon) coated stainless steel wire or other heat resistant material that does not readily bond to the extrudate. By additionally limiting the area draw down ratio (ADDR) to below 10:1 the tungsten-laden melt can successfully be drawn to size by an extrusion puller. The beading provides the added benefit of fixing the inner diameter and improving overall dimensional stability of the final tungsten/polymer coating. Extrusions of a 91.3 weight percent fill ratio tungsten/Pebax composition described above over 0.0215" diameter PTFE beading were successfully drawn down to a wall thickness of 0.0025" to yield a marker properly sized for attachment to for example a 0.022" diameter inner member of balloon catheter. Also, extrusion coatings of 91% compound over 0.007" teflon coated stainless steel wire were successfully drawn down to single wall thicknesses of 0.002" to make guidewire coatings.

In one embodiment, once the extrudate has cooled, the extrusion is simply cut to the desired lengths (e.g., 1 to 1.5 mm) of the individual markers, such as with the use of a razor blade and reticle, preferably with the beading still in place to provide support during cutting. The beading remnant is subsequently ejected and the marker is slipped onto a medical device or a particular component thereof. In one embodiment, a segment of the extrudate is hot die necked with the beading inside to resize the outer diameter and wall thickness of the extrudate prior to cutting into individual markers. For example, an extrudate, having an inner diameter of about $0.0215 \pm 0.0005$ inch and an outer diameter of about $0.0275 \pm 0.001$ inch, is hot die necked to an outer diameter of about 0.0265 inch to produce a double wall thickness of about $0.005 \pm 0.005$ inch. To minimize part to part variability in double wall thickness, the actual hot die size may be selected based upon the actual beading diameter prior to hot die necking.

Finally, the marker is attached to the underlying substrate, preferably with the use of heat shrink tubing and a heat source (hot air, laser, etc.) wherein the heat (~171-210° C.) simultaneously causes the marker to melt and the heat shrink tubing to exert a compressive force on the underlying molten material. To prevent extensive dimensional changes (e.g., thinning) of the polymeric marker, the temperatures used are below the melting temperature, thereby relying on heat and pressure to soften the marker and generate an adhesive bond with the underlying substrate. For markers formed of PEBAX 40D, the temperature used is about 120°-135° C. Heat bonding a marker onto an underlying component provides the added benefit of slightly tapering the edges of the marker to reduce the likelihood of catching an edge and either damaging the marker or the medical device during assembly or handling of the medical device.

A marker formed as per the above described compounding, fabricating and assembling processes, having a fill ratio of 91.3 weight percent (36.4 volume percent) with a wall thickness of 0.0025" has been shown to have dramatically more radiopacity than commercially available 80 weight percent compounds and comparable to the radiopacity of 0.00125 inch thick conventional Platinum/10% Iridium markers. The radiopacity is a function of the total volume of radiopaque material present in the marker (i.e., the product of the volume % and the volume of the marker). In a presently preferred embodiment, the marker is about 1.5 mm long and has a double wall thickness of about 0.0045 to about 0.0055 inch and a fill ratio of about 90.8 to about 93.2 weight percent of tungsten, which provides a volume of radiopaque material substantially equal to the volume of Platinum/10% Iridium in a 1.0 mm long, 0.0025 inch thick (double wall) conventional Platinum/Iridium marker band. Preferably, the volume of radiopaque material is not less than about 30%, and the double wall thickness of the marker is at least about 0.004 inch, to provide sufficient radiopacity. However, as discussed above, the ability to increase the volume of the marker by increasing the wall thickness of the marker is limited by the resulting increase in profile and stiffness. In a presently preferred embodiment, the double wall thickness of the marker is not greater than about 0.006 inch.

In the embodiment illustrated in FIG. 29, three radiopaque marker bands are provided on the second inner tubular member 174, to facilitate positioning the distal end of the catheter 140 in place in the patient's vasculature. In an alternative embodiment (not shown), a single radiopaque marker is provided on the first or second inner tubular member 172 or 174 as a carina marker band. The single radiopaque marker is secured to the first or second inner tubular member 172 or 174, preferably by adhesive bonding or crimping, such that it is aligned with the proximal end of the first balloon 166 or preferably aligned on the trap door opening of the stent. The single radiopaque marker provides improved manufacturability and flexibility compared to multiple markers.

Bifurcated catheter 140 is similar in many respects to the catheter assembly 101 disclosed herein, and it should be understood that the disclosure and individual features of the bifurcated catheter 140 and catheter assembly 101 discussed and illustrated with respect to one of the embodiments applies to the catheter assembly 101 discussed and illustrated with respect to one of the embodiments applies to the other embodiment as well. To the extent not discussed herein, the various components of catheter 140 can be formed of conventional materials used in the construction of catheters, and joined together using conventional methods such as adhesive bonding and fusion bonding. In one embodiment, the proximal outer tubular member is formed of a relatively high strength material such as a relatively stiff nylon material or a metal hypotube. The intermediate tubular member and distal outer tubular members are preferably formed of a polymeric material including polyamides such as nylon or urethanes. The inner tubular members preferably have at least an outer layer which is fusion bondable (i.e., compatible) with the polymeric material of the balloons and the coupler. In one embodiment, the coupler and distal tip members are formed of a polyamide such as polyether block amide (PEBAX) or blend thereof.

The materials used to construct the catheter assembly 101 or 140 are known in the art and can include for example various compositions of PEBAX, PEEK (polyetherketone), urethanes, PET or nylon for the balloon materials (polyethylene terephathalate) and the like. Other materials that may be used for the various shaft constructions include fluorinated ethylene-propylene resins (FEP), polytetrafluoroethylene (PTFE), fluoropolymers (Teflon), Hytrel polyesters, aromatic polymers, block co-polymers, particularly polyamide/polyesters block co-polymers with a tensile strength of at least 6,000 psi and an elongation of at least 300%, and polyamide or nylon materials, such as Nylon 12, with a tensile strength of at least 15,000 psi. The various shafts are connected to each other using well known adhesives such as Loctite or using heat-shrink tubing over the joint of two shafts, of which both methods are well known in the art. Further, any of the foregoing catheter materials can be combined with a compound that is visible under MRI, such as 19F, as previously discussed herein.

Delivering and Implanting the Stent

Referring to FIGS. 35-41, the bifurcated catheter assembly of the present invention provides two separate balloons in parallel which can be advanced into separate passageways of an arterial bifurcation and inflated either simultaneously or independently to expand and implant a stent. As shown in the drawings, bifurcation 300 typically includes a main vessel 301 and a side branch vessel 302 with the junction between the two referred to as the carina 304. Typically, plaque 305 will develop in the area around the junction of the main vessel and the side branch vessel and, as previously described with the prior art devices, is difficult to stent without causing other problems such as portions of the stent extending into the blood flow path jailing a portion of the side branch vessel, or causing plaque to shift at the carina and subsequently occlude the vessel.

In keeping with the invention, the catheter assembly 101 or 140 is advanced through a guiding catheter (not shown) in a known manner. Once the distal end 102 of the catheter reaches the ostium to the coronary arteries, the Rx guide wire 310 is advanced distally into the coronary arteries (or any other bifurcated vessel) so that the Rx guide wire distal end 311 extends past the opening to the side branch vessel 303. (In most cases, the main vessel will have been predilated in a known manner prior to delivery of the trap door stent. In these cases, the Rx guide wire will have been left in place across and distal to the target site prior to loading the catheter assembly onto the Rx guide wire for advancement to the target site.) After the distal end of the Rx guide wire is advanced into the main vessel past the opening to the side branch vessel, the catheter is advanced over the Rx guide wire so that the catheter distal end 102 is just proximal to the opening to the side branch vessel. Up to this point in time, the OTW guide wire 312 (or mandrel) remains within the catheter and within coupler 119 keeping the tips and balloons joined. More specifically, the OTW guide wire remains within the OTW guide wire lumens 105, 108, and 130 as previously described. The distal end of the OTW guide wire 313 is positioned within coupler blind lumen 121 during delivery and up to this point in time. As the catheter is advanced through tortuous coronary arteries, the OTW guide wire distal end 313 should be able to slide axially a slight amount relative the coupler blind lumen to compensate for the bending of the distal end of the catheter. As the catheter distal end moves through tight twists and turns, the coupler moves axially relative to the balloon shaft that it is not attached to thereby creating relative axial movement with the OTW guide wire. Stated differently, the coupler moves axially a slight amount while the OTW guide wire remains axially fixed (until uncoupled) relative to the catheter shaft. If the OTW guide wire were fixed with respect to the coupler at the distal end, it would make the distal end of the catheter stiffer and more difficult to advance through the coronary arteries, and may cause the distal end of the catheter to kink or to be difficult to push through tight turns. Thus, the coupler moves axially relative to the distal end of the OTW guide wire in a range of approximately 0.5 mm up to about 5.0 mm. Preferably, the coupler moves axially relative to the OTW guide wire distal end 313 about 0.5 mm to about 2.0 mm. The amount of axial movement will vary depending on a particular application and the severity of the tortuousity. The proximal end of the OTW guide wire (or joining wire or mandrel) should be removably fixed relative to the catheter shaft during delivery so that the distal end of the OTW guide wire does not prematurely pull out of the coupler. The distal end of the OTW guide wire still moves axially a small amount within the coupler as the distal end of the catheter bends and twists in negotiating tortuous anatomy.

As previously disclosed and as shown in FIG. 28A, radiopaque markers 140 are positioned on the inner shaft and coincide or align with the long balloon 117 and the short balloon 129. The radiopaque markers will assist the position in positioning the catheter assembly 101, and more specifically the long balloon and short balloon with respect to the opening to the side branch vessel 303. Typically, it is desirable to have one radiopaque marker centered with respect to the length of the long balloon, and perhaps several other radiopaque markers defining the overall length of the long balloon, or defining the length of the unexpanded or expanded stent 20. Similarly, a radiopaque marker associated with the short balloon is preferably aligned with the center radiopaque marker of the long balloon.

Figure 36:
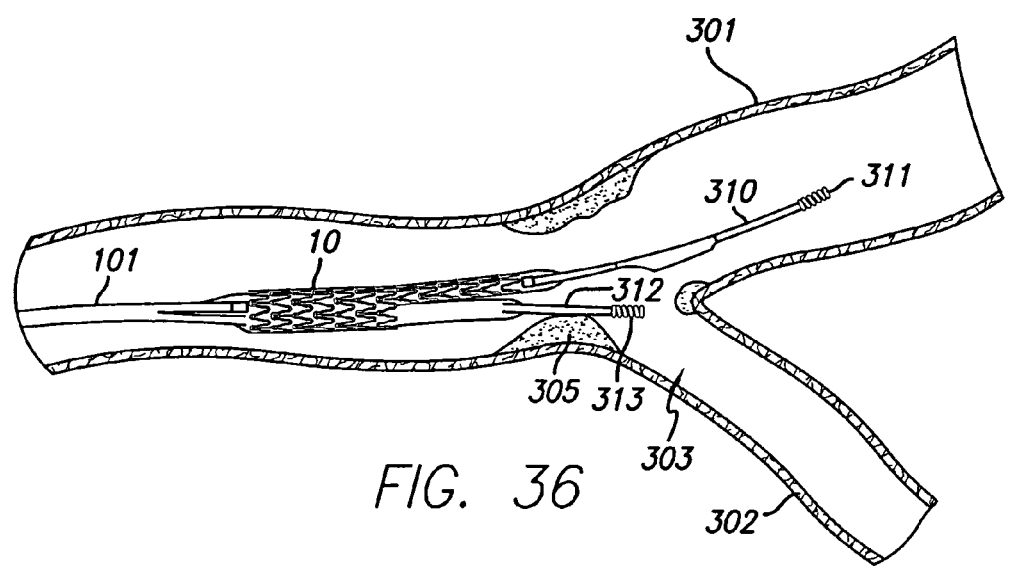
FIG. 36 is an elevational view of the catheter assembly in the main vessel prior to advancement into the side branch vessel.
Figure 37:
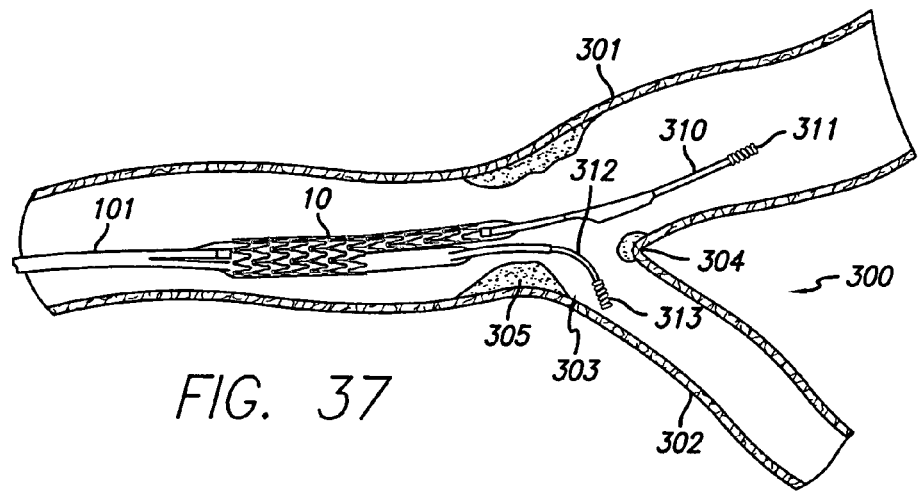
FIG. 37 is an elevational view of the catheter assembly as the over-the-wire guide wire is being advanced into the side branch vessel.
Figure 38:
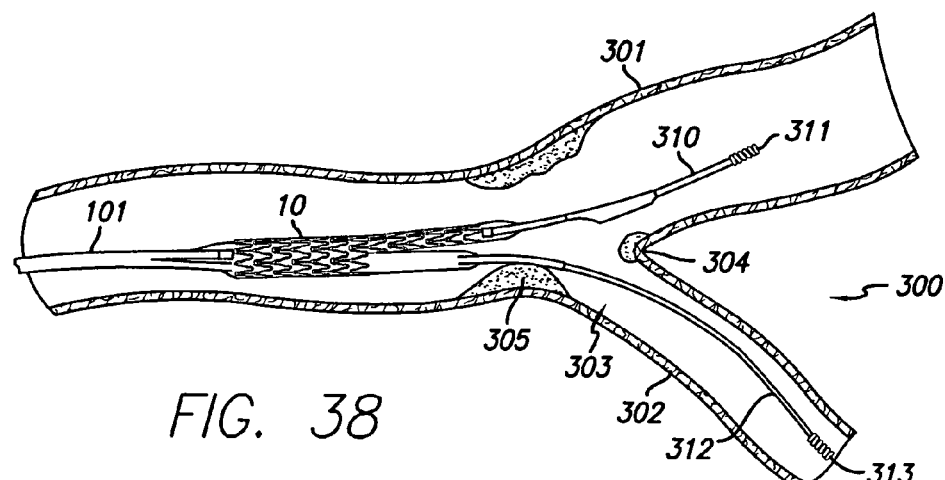
FIG. 38 is an elevational view of the catheter assembly positioned in the main vessel and the over-the-wire guide wire advanced and positioned in the side branch vessel.
Figure 39:
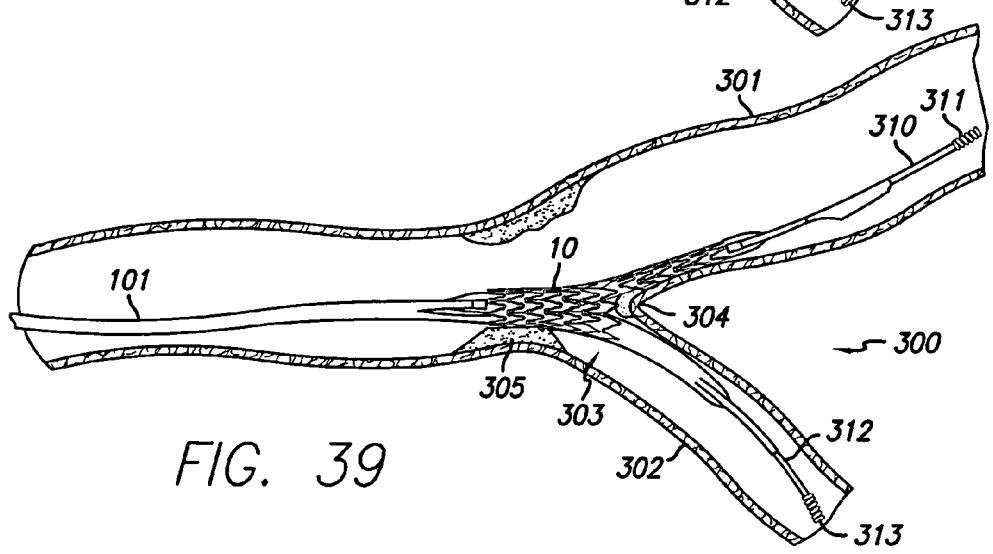
FIG. 39 is an elevational view of the catheter assembly advanced so that the long balloon is in the main vessel and a portion of the short balloon is positioned in the side branch vessel.
Figures 40, 41:
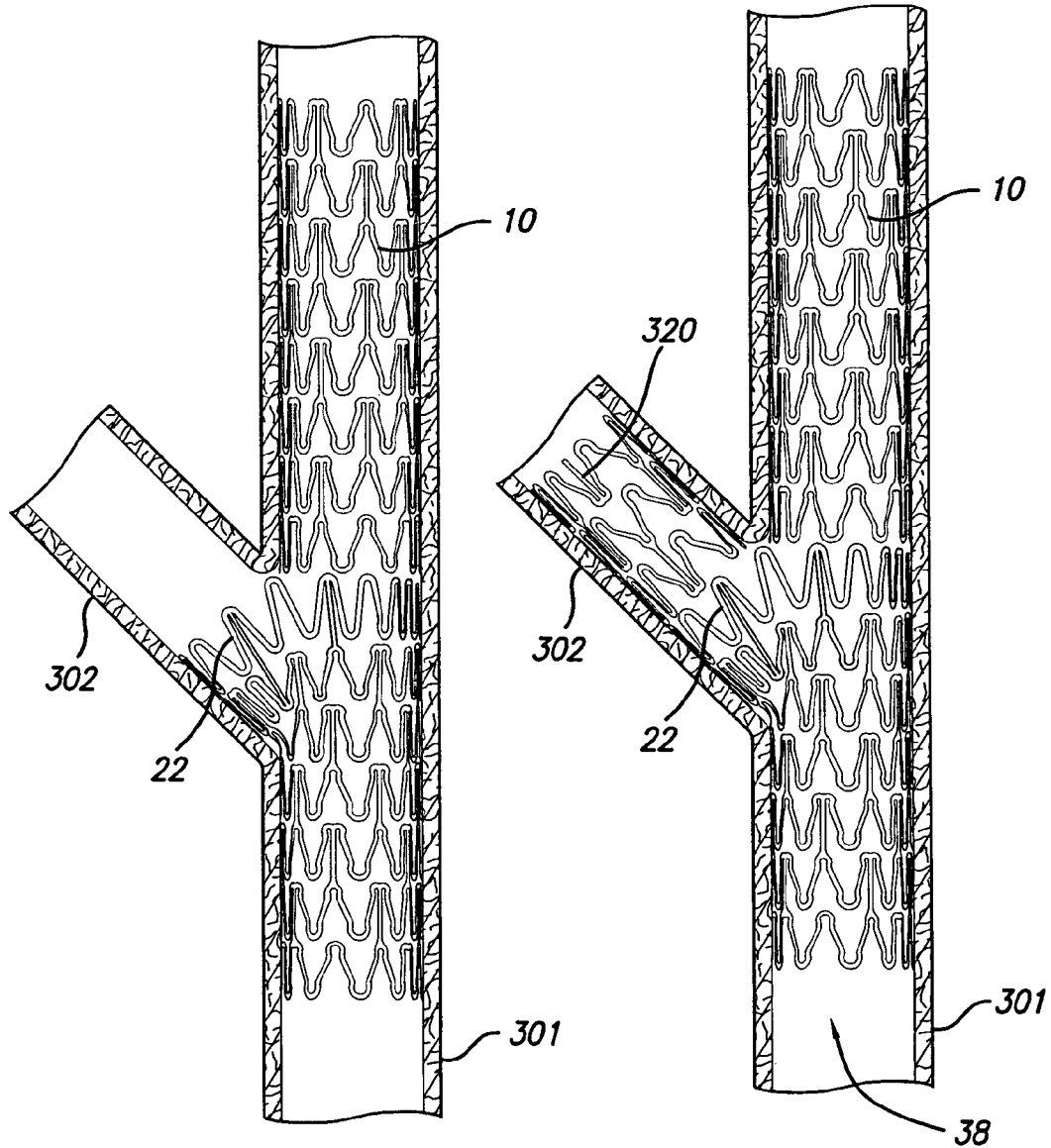
FIG. 40 is an elevational view of a bifurcation depicting the stent of the invention implanted in the main vessel and the opening to the side branch vessel.
FIG. 41 is an elevational view of a bifurcation in which the stent of the present invention is implanted in the main vessel, and a second stent is implanted in the side branch vessel.
Figure 42:
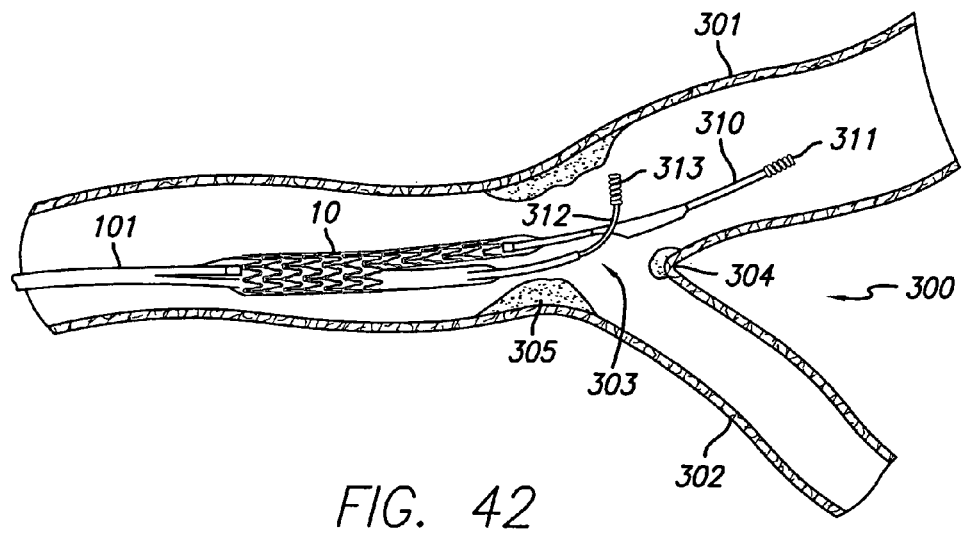
FIG. 42 is an elevational view depicting the catheter assembly positioned in the main vessel and the over-the-wire guide wire advancing out of the catheter.
Figure 43:
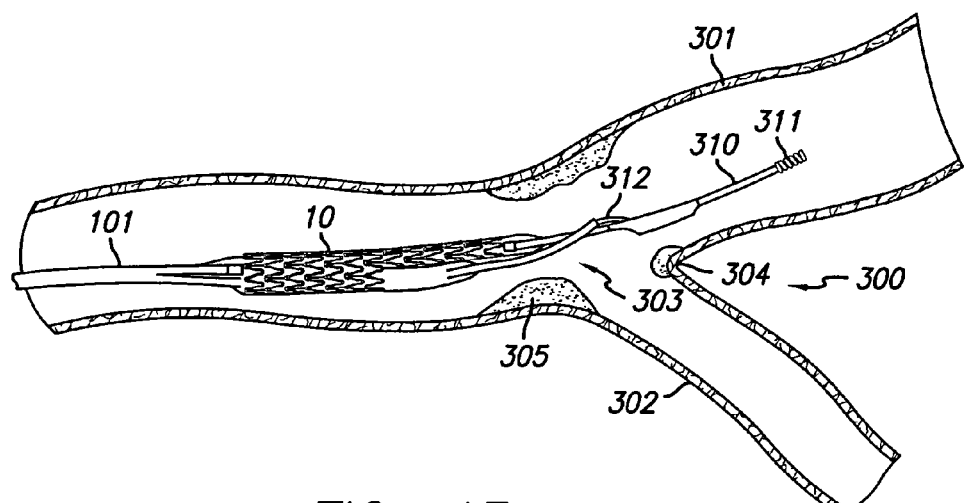
FIG. 43 is an elevational view of the catheter assembly positioned in the main vessel and the over-the-wire guide wire wrapping around the coupler.
Figure 44:
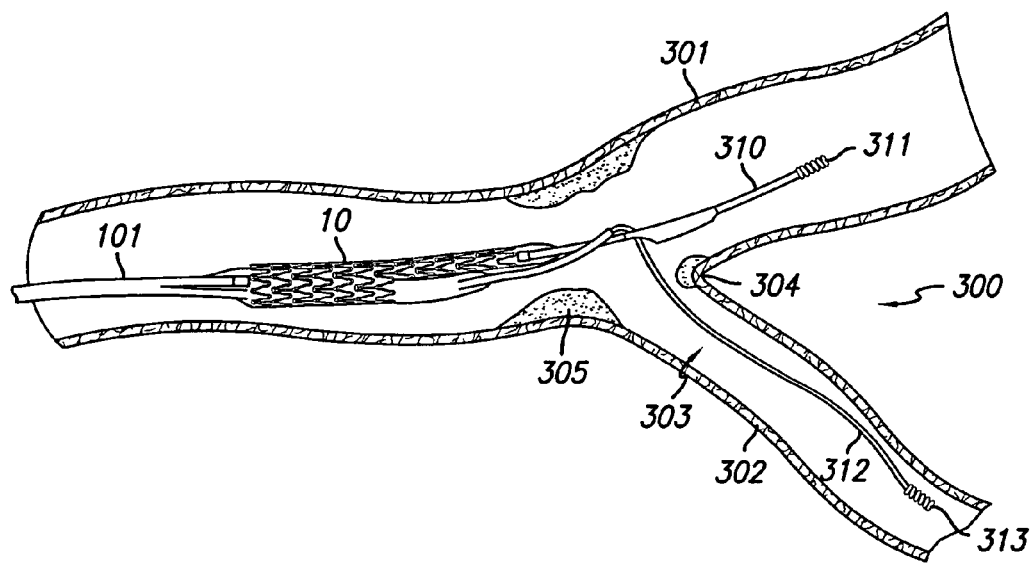
FIG. 44 is an elevational view showing the catheter assembly positioned in the main vessel and the over-the-wire guide wire wrapped over the coupler and positioned in the side branch vessel.

As shown for example in FIG. 36, the OTW guide wire 312 next is withdrawn proximally so that the OTW guide wire distal end 313 is removed from the coupler blind lumen 121. As shown in FIG. 37, the OTW guide wire next is advanced distally into the side branch vessel 302, extending past the opening to the side branch vessel 303 and advancing distally into the vessel for a distance as shown in FIG. 38. Once the Rx guide wire 310 is in position in the main vessel, and the OTW guide wire 312 is in position in the side branch vessel, this will have a tendency to impart a slight separation between the long balloon 117 and the short balloon 129. As shown in FIG. 39, the catheter assembly 101 is advanced distally over the Rx guide wire and the OTW guide wire and, as the assembly is further advanced, the long balloon 117 continues to separate from the short balloon 129 as each advances into the main vessel 301 and the side branch vessel 302 respectively. As the assembly continues to advance distally, it will reach the point where portal section 22 on the stent 10 is adjacent the opening to the side branch vessel 303. At this point, the catheter assembly can no longer be advanced distally since the stent is now pushing up against the opening to the side branch vessel. The long balloon 117 and the short balloon 129 are next inflated simultaneously to expand the stent 10 into the main vessel and into the opening to the side branch vessel. As shown in FIG. 40, a portion of the portal section 22 of the stent will expand into contact with the opening to the side branch vessel and the portal section 22 of the stent should coincide with the opening to the side branch vessel providing a clear blood flow path through the proximal end 12 of the stent and through the portal section 22 into the side branch vessel. The expanded stent 10 is shown in FIG. 40 covering a portion of the main vessel and the opening to the side branch vessel.

In keeping with the invention, as the catheter assembly is advanced through tortuous coronary arteries, the portal section 22 of the stent 10 may or may not always be perfectly aligned with the opening to the side branch vessel 303. If the portal section of the stent is in rotational alignment with the opening to the side branch vessel, the stent is said to be "in phase" and represents the ideal position for stenting the main branch vessel and the opening to the side branch vessel. When the portal section and the opening to the side branch vessel are not rotationally aligned it is said to be "out of phase" and depending upon how may degrees out of phase, may require repositioning or reorienting the portal section 22 with respect to the opening to the side branch vessel. More specifically, the mis-alignment can range anywhere from a few degrees to 360°. If the central opening is in excess of 90° out of phase with respect to the opening to the side branch vessel, it may be difficult to position the stent with respect to the longitudinal axis. When the out of phase position is approximately 270° or less, the stent 10 still can be implanted and the portal section will expand into the opening to the side branch vessel and provide adequate coverage provided that the stent and radiopaque markers can be positioned longitudinally. Due to the unique and novel design of the catheter assembly and the stent of the present invention, this misalignment is minimized so that the portal section 22 generally aligns with the opening to the side branch vessel, even if the central opening is out of phase approximately 90° from the opening of the side branch vessel 303. Typically, the alignment between the portal section 22 and the opening to the side branch vessel will be less than perfect, however, once the OTW guide wire 312 is advanced into the side branch vessel 302, as previously described, the assembly will slightly rotate the portal section 22 into better alignment with the opening to the side branch vessel. As can be seen in FIGS. 35-39, after the stent has been properly oriented, it is expanded into contact with the main branch vessel and the portal section 22 expanded to contact with the opening to the side branch vessel.

As shown in FIG. 41, a second stent 320 can be implanted in the side branch vessel 302 such that it abuts portal section 22 of stent 10. The second stent can be delivered and implanted in the following manner. After implanting stent 10, the long balloon 117 and the short balloon 119 are deflated and catheter assembly 101 (or 140) are removed from the patient by first withdrawing the Rx guide wire 310 and then withdrawing the catheter assembly over the in-place OTW guide wire 312 (an extension guide wire which is known in the art may be required), which remains in the side branch vessel 302. Alternatively, the catheter assembly can be withdrawn from the patient while leaving both the Rx and OTW guide wires in place in their respective vessels. Next, a second catheter assembly (not shown) on which second stent 320 is mounted, is backloaded onto the proximal end of the OTW guide wire 312. The catheter assembly is next advanced through the guiding catheter and into the coronary arteries over the OTW guide wire, and advanced such that it extends into proximal end 12 of the expanded and implanted stent 10. The second catheter assembly is advanced so that it extends through the opening to the side branch vessel and advances over the OTW guide wire 312 and into the side branch vessel where second stent 320 can be expanded and implanted in the side branch vessel to abut the portal section 22 of stent 10. Alternatively, the catheter assembly 101 can be withdrawn to just proximal of the bifurcation, the Rx guide wire 310 withdrawn proximally into the catheter, and then the catheter assembly advanced into the side branch vessel over the in-place OTW guide wire 312. The Rx guide wire can then be advanced into the side branch vessel, the OTW guide wire safely withdrawn into the catheter assembly, and the catheter assembly then safely removed in an Rx exchange over the Rx guide wire which remains in place in the side branch vessel. Thereafter the second catheter assembly can be advanced over the in-place Rx guide wire 310 and into the side branch vessel where the second stent is implanted as previously described. Care must be taken in this approach to avoid wire wrapping, that is avoiding wrapping the Rx and OTW guide wires in the side branch vessel.

In another alternative embodiment for implanting second stent 320, the long balloon 117 and the short balloon 119 are deflated and catheter assembly 101 is removed from the patient by first withdrawing OTW guide wire 312 so that it resides within the catheter assembly, and then withdrawing the catheter assembly over the in-place Rx guide wire 310, which remains in the main vessel 301. Next, a second catheter assembly (not shown) on which second stent 320 is mounted, is back loaded onto the proximal end of Rx guide wire 310, advanced through the guiding catheter into the coronary arteries, and advanced such that it extends into the proximal end 12 of the expanded and implanted stent 10. The Rx guide wire is then withdrawn proximally a short distance so that the Rx guide wire distal end 311 can be torqued and rotated so that it can be advanced into the side branch vessel 302. Once the Rx guide wire is advanced into the side branch vessel, the second catheter is advanced and the second stent 320 is positioned in the side branch vessel where it is expanded and implanted in a conventional manner as shown in FIG. 41. The second catheter assembly is then withdrawn from the patient over the Rx guide wire.

Figure 35:
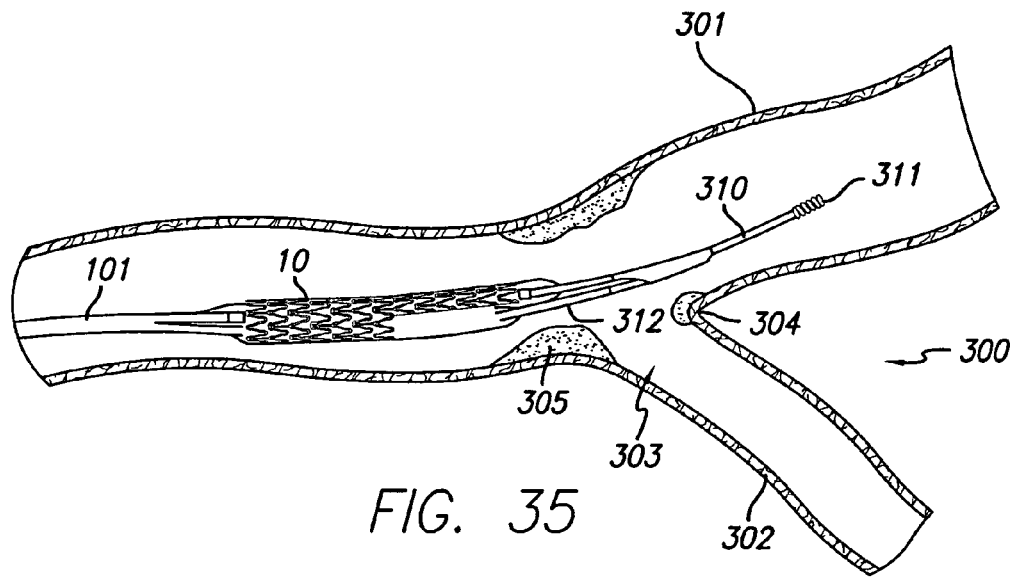
FIG. 35 is an elevational view of the catheter assembly being advanced into the main vessel.

In an alternative method of deploying and implanting stent 10, the catheter assembly 101 as shown in FIGS. 35-41 can be adapted to carry a mandrel (not shown) instead of the OTW guide wire. For example, during delivery and positioning of the stent in the main branch vessel 301, a mandrel resides in the OTW guide wire lumens 105, 108, and 130, and the distal end of the mandrel extends into and resides in coupler blind lumen 121. As the catheter assembly is positioned just proximal to the bifurcation, such as shown in FIGS. 35 and 36, the mandrel is withdrawn proximally from the catheter assembly allowing the long balloon 117 and the short balloon 129 to slightly separate. Thereafter, an OTW guide wire 312 is front-loaded into the proximal end of the catheter assembly and advanced through the OTW guide wire lumens and into the side branch vessel 302 as shown in FIGS. 37 and 38. After this point, the delivery and implanting of the stent is the same as previously described.

In an alternative method of delivering and implanting the stent of the invention, the catheter assembly 101 or 140 is advanced through a guiding catheter (not shown) in a known manner. Once the distal end 102 of the catheter reaches the ostium to the coronary arteries, the Rx guide wire 310 is advanced out of the Rx shaft 111 and advanced distally into the coronary arteries (or any other bifurcated vessels) so that the Rx guide wire distal end 311 extends through the opening to the side branch vessel 303. (As noted above, the Rx guide wire may already be positioned in the main vessel or side branch vessel as a result of a pre-dilatation procedure). After the distal end of the Rx guide wire is advanced into the side branch vessel, the catheter is advanced over the Rx guide wire so that the catheter distal end 102 is positioned distal to the opening to the side branch vessel and partially within the side branch vessel. More specifically, the short tip of the short balloon 129 should be distal to the carina 304. Up to this point in time, the OTW guide wire 312 remains within the catheter and within coupler 119. More specifically, the OTW guide wire remains within the OTW guide wire lumens 105, 108, 130 as previously described. The distal end of the OTW guide wire 313 is positioned within coupler blind lumen 121 during delivery and up to this point in time. As the catheter is advanced through tortuous coronary arteries, for example, the OTW guide wire distal end 313 should be able to move axially a slight amount within the coupler blind lumen to compensate for the bending of the distal end of the catheter. If the OTW guide wire were fixed with respect to the catheter shaft and the coupler at the distal end, it would make the distal end of the catheter stiffer and more difficult to advance through the coronary arteries, and may cause the distal end of the catheter to kink or be more difficult to push through tight turns. Thus, the distal end of the OTW guide wire will move axially in a range of approximately 0.5 mm up to about 5.0 mm. Preferably, the OTW guide wire distal end 313 will move back and forth axially about 0.5 mm to about 2.0 mm. The amount of axial movement depends on a particular application or vessel tortuousity. The proximal end of the OTW guide wire should be removably fixed relative to the catheter shaft during delivery so that the distal end of the OTW guide wire does not prematurely pull out of the coupler. The distal end of the OTW guide wire still moves axially a small amount within the coupler as the distal end of the catheter bends and twists in negotiating tortuous anatomy.

The OTW guide wire 312 next is withdrawn proximally so that the OTW guide wire distal end 313 is removed from the coupler blind lumen 121. The OTW guide wire next is advanced distally into the side branch vessel 302 a short distance. The catheter assembly is next withdrawn proximally so the long balloon 117 and the short balloon 129 are in the main vessel just proximal of the opening of the side branch vessel. More specifically, the coupler distal tip is proximal to vessel carina 304. As the catheter assembly is withdrawn from the side branch vessel, the long balloon and short balloon will begin to separate slightly. Thereafter, the Rx guide wire 310 is withdrawn proximally until it is clear of the opening to the side branch vessel, whereupon it is advanced distally into the main branch vessel for a distance. The catheter assembly next is advanced distally over the Rx guide wire in the main branch vessel and the OTW guide wire in the side branch vessel. As the catheter advances distally, the long balloon and short balloon will separate at least partially until the short balloon enters the side branch vessel and the long balloon continues in the main branch vessel. As the balloons and stent push up against the ostium of the bifurcation, the catheter assembly cannot be advanced further and the stent is now in position to be expanded and implanted. At this point the radiopaque markers should be appropriately positioned. The portal section 22 on the stent 10 should be approximately adjacent the opening to the side branch vessel 303. The long balloon 117 and the short balloon 129 are next inflated simultaneously to expand the stent 10 into the main vessel and into the opening into the side branch vessel respectively. A portion of the portal section 22 of the stent will expand into contact with the opening to the side branch vessel and the portal section 22 of the stent should coincide to the opening of the side branch vessel providing a clear blood flow path through the proximal end 12 of the stent and through the portal section 22 into the side branch vessel. When fully expanded, stent 10 should cover at least a portion of the main vessel and the opening to the side branch vessel. After the stent has been expanded and implanted, the balloons are deflated and the assembly is withdrawn from the vascular system over the Rx and OTW guide wires. The Rx and OTW guide wires remain in place in the main and side branch vessels for further procedures.

The above procedures can also be performed with a spare safety wire placed in the alternate vessel. The safety wire is removed from the patient after the OTW guide wire has been advanced into the side branch vessel (first case) or the Rx guide wire has been advanced into the distal main vessel (second case). The safety wire allows access to the vessel should closure from a dissection or spasm occur.

Figure 45:
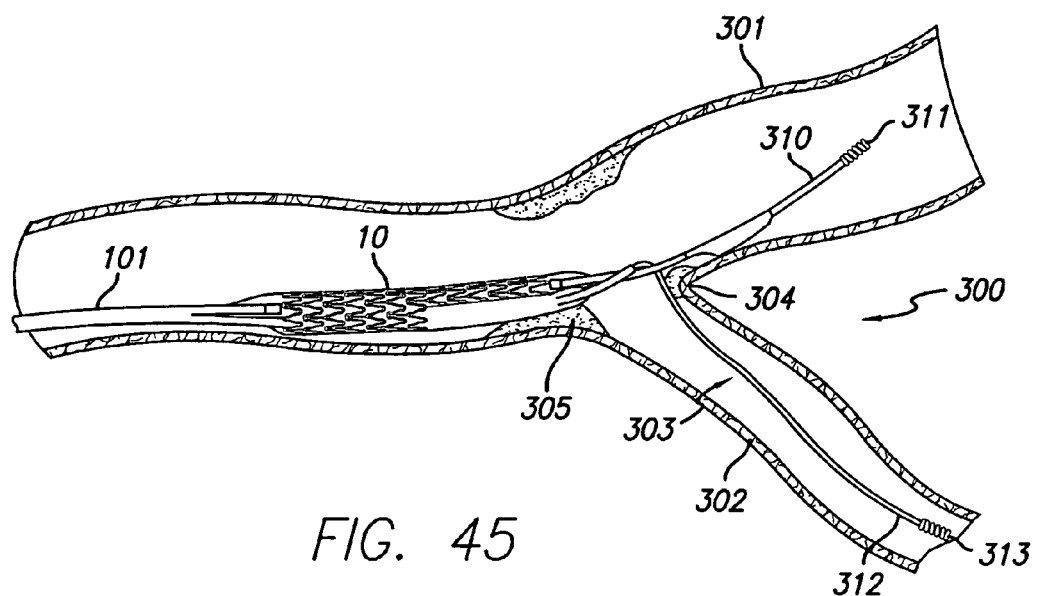
FIG. 45 is an elevational view of the catheter assembly advanced toward the carina or bifurcation junction but unable to advance further due to the over-the-wire guide wire wrapped over the coupler and/or the long tip.

As can be seen in FIGS. 42-45, the OTW guide wire 312 on occasion can be inadvertently torqued in the wrong direction and wrap around the distal end 102 of the catheter or around the coupler 119 prior to advancing into the side branch vessel 302. If this occurs, and the OTW guide wire is advanced into the side branch vessel, the catheter assembly can be advanced distally only a certain distance before the crossed wires reach the junction or carina of the main vessel and the side branch vessel and the catheter can no longer be advanced distally. At this point, the physician knows that the wires are wrapped or that the central opening is severely out of alignment with the opening of the side branch vessel, in which cases the OTW guide wire 312 is withdrawn proximally into the catheter and the catheter assembly is reoriented by rotating the assembly to better position the portal section 22 with respect to the opening to the side branch vessel prior to advancing the OTW guide wire 312. Thus, as shown in FIG. 45, once the guide wires are wrapped, the OTW guide wire must be withdrawn proximally, and then readvanced into the side branch vessel taking care to avoid wrapping. The catheter assembly would then be readvanced in an effort to reorient the portal section 22 with the opening to the side branch vessel.

If it becomes impossible to deliver the stent for whatever reason, including that described above with respect to the wrapped guide wires, the catheter assembly 101 can be withdrawn into the guiding catheter and removed from the patient.

Typically, the OTW guide wire 312 would be withdrawn proximally into the catheter and the catheter assembly would be withdrawn proximally over the Rx guide wire which remains in place in the main vessel 301. Alternatively, as the catheter assembly is withdrawn, the stent can be safely implanted proximal to the bifurcation. If desired, a second catheter assembly can be backloaded over in-place Rx guide wire 310 and advanced through the guiding catheter and into the coronary arteries as previously described to implant another stent.

Figure 46:
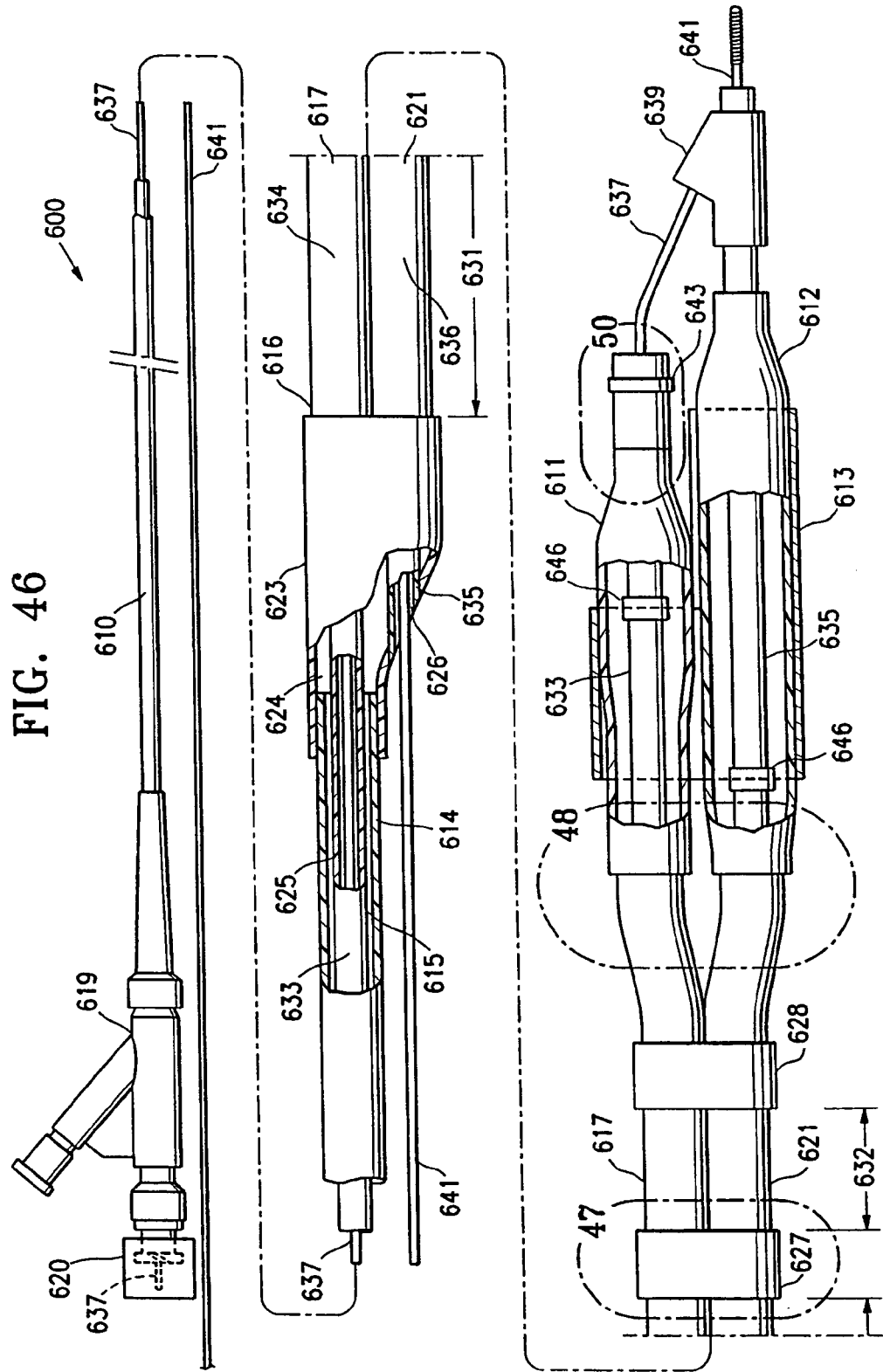
FIG. 46 is an elevational view, partially in section, of a stent delivery balloon catheter embodying features of the invention, having secured portions along which the first and second branches of the catheter are permanently secured together, and having a polymeric radiopaque distal tip marker.
Figure 48:
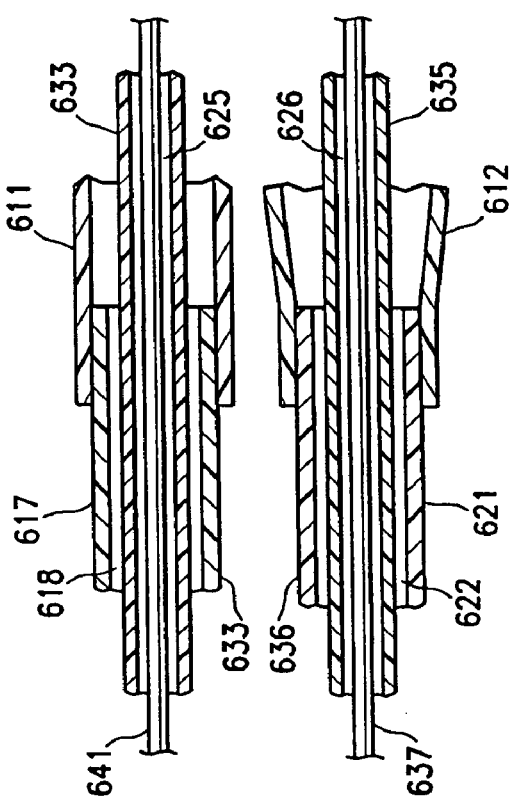
FIGS. 47 and 48 are enlarged, longitudinal sectional views of the catheter of FIG. 46, taken within circles 47 and 48, respectively.
Figure 47:
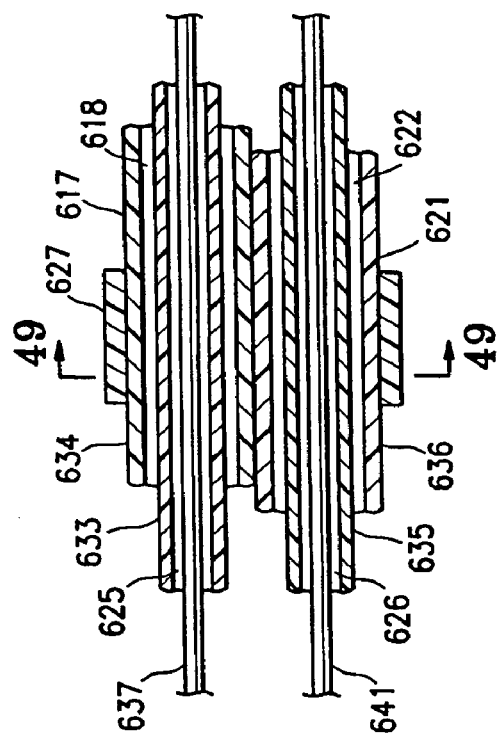
Figure 49:
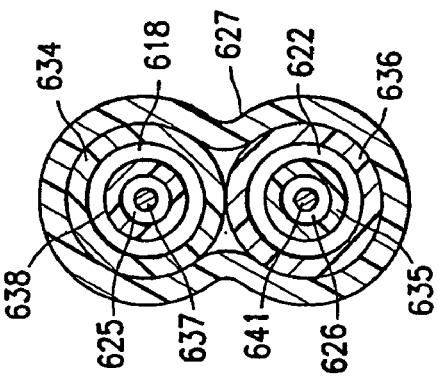
FIG. 49 is a transverse cross section of the catheter of FIG. 48, taken along line 49-49.

FIG. 46 illustrates an alternative embodiment of a stent delivery balloon catheter 600 embodying features of the invention, generally comprising an elongated shaft 610, a first balloon 611, a second balloon 612, and a stent 613 releaseably mounted on the first and second balloons for delivery and deployment within a patient's bifurcated body lumen. The elongated shaft 610 has a proximal section 614 having a first inflation lumen 615, and a bifurcated distal section 616 having a first branch 617 with a second inflation lumen 618 within at least a portion thereof and a second branch 621 with a third inflation lumen 622 within at least a portion thereof, as best illustrated in FIGS. 47-49, illustrating cross sectional views of the catheter of FIG. 46. The second and third inflation lumens 618, 622 are each in fluid communication with the first inflation lumen 615. An intermediate section 623 extends between the proximal section and the branched distal section, and has a fourth inflation lumen 624 in fluid communication with the first, second, and third inflation lumens.

In the embodiment illustrated in FIG. 46, the proximal shaft section 614 comprises a proximal outer tubular member defining the first inflation lumen 615, the first branch 617 of the bifurcated distal shaft section 616 is formed in part by a first distal outer tubular member 634, and the second branch 621 is formed in part by a second distal outer tubular member 636. The intermediate shaft section 623 comprises an intermediate outer tubular member defining the fourth inflation lumen 624. In the embodiment illustrated in FIG. 46, the intermediate outer tubular member is a separate tubular member secured to the distal end of the proximal outer tubular member. However, a variety of suitable configurations can be used to transition from the proximal shaft section to the bifurcated distal shaft section, including alternative embodiments (not shown) in which the intermediate section 623 (or intermediate outer tubular member) is an integral, one piece unit with the proximal section 614, formed by a distal end portion of the proximal section 614.

A joining wire lumen 625 extends within the proximal section, the intermediate section, and the first branch, and a rapid exchange guidewire lumen 626 extends within the intermediate section and the second branch. A proximal adapter 619 is secured to the proximal end of the catheter shaft, which has an arm configured for connecting to a source of inflation fluid for inflating the balloons 611, 612, and which provides access to joining wire lumen 625.

In the illustrated embodiment, the first branch 617 comprises an inner tubular member 633 defining the joining wire lumen 625 and outer tubular member 634 defining, together with the outer surface of the inner tubular member 625 therein, the second inflation lumen 618 in the annular space between the inner and outer tubular members 633, 634 (see FIG. 49). The second branch 621 similarly comprises an inner tubular member 635 defining the guidewire lumen 626 and outer tubular member 636 defining, together with the outer surface of the inner tubular member 625 therein, the third inflation lumen 622.

In a presently preferred embodiment, the first balloon 611 is a shorter balloon on an OTW branch of the catheter 600 and the second balloon 612 as a longer balloon on a Rx branch of the catheter 600. However, in an alternative embodiment (not shown), the shorter balloon is on an Rx branch and the longer balloon is on an OTW branch of the catheter 600. In the embodiment of FIG. 46, the proximal ends of the first and second balloons 611, 612 are radially aligned. Specifically, although the inflatable length of the first balloon 611 is substantially shorter than that of the second balloon 612, the first balloon has an extended proximal skirt section sealingly secured to the shaft, which extends proximally to a location radially aligned with the proximal end of the proximal skirt section of the second balloon 612, in the embodiment of FIG. 46. In the embodiment of FIG. 46, the distal ends of the first and second branch outer tubular members 634, 636 are radially aligned. In an alternative embodiment (not shown), the first branch outer tubular member 634 has a distal end section which extends longitudinally along the extended proximal skirt section of the first (shorter) balloon 611, to a location distal to the distal end of the second branch outer tubular member 636.

The bifurcated distal section has a first secured portion and a second secured portion along which the first and second branches are permanently secured together, and which in the illustrated embodiment are formed at least in part by first and second tubular outer band members 627, 628 which surround and thereby constrain the first and second branches of the distal shaft section together. FIGS. 47 and 48 illustrate enlarged, longitudinal sectional views of the catheter of FIG. 46, taken within circles 47 and 48, respectively FIG. 47 illustrates the first tubular outer band member 627 on the first and second branches 617, 621 of the catheter. The tubular outer band members 627, 628 constrain the first and second branches together, thus bringing and holding the first and second branches in contact with one another along the secured portions formed thereby, when the balloons are in a deflated or inflated configuration (see, e.g., FIG. 55 which illustrates the inflated balloons and which is discussed in more detail below). The tubular outer band members are preferably a solid-walled length of tubing, and thus extend continuously around the circumference thereof.

The secured portions 627, 628 are located proximal to the proximal end of the stent 613 mounted on the first and second balloons. The first secured portion 627 is located approximately midway between a proximal end of the first and second balloons and a proximal end of the branched distal shaft section. A first unsecured portion 631, along which the first and second branches are not secured together, is proximally adjacent to the first secured portion. The second secured portion is distally spaced apart from the first secured portion by an unsecured portion 632. In the embodiment illustrated in FIG. 46, the second secured portion 628 is located adjacent to but proximally spaced apart from the proximal end of the first and second balloons. In one embodiment (not shown), the first and second branches have a single tubular outer band member securing the branches together, and generally located approximately midway between the location of the first and second bands 627, 628 in the embodiment of FIG. 46 such that unsecured portions are adjacent to the proximal and the distal end of the single tubular outer band member.

In a presently preferred embodiment, the tubular outer band members are a heat shrinkable polymer such as polyester heat shrink tubing, which is heat shrunk onto the first and second branches. Preferably, adhesive (not shown) is provided under the outer band members to adhesively secure the band members to the first and second branches of the distal shaft section.

The outer band members are preferably molded or otherwise caused to conform to the shape of the first and second outer tubular members secured together. For example, in a presently preferred embodiment, with the outer band members 627, 628 in place on the first and second branches, each secured portion (i.e., at the location of each outer band member 627, 628) is heated in a mold with an internal chamber configured to force the band member against the underlying shaft surface, thereby causing the band member to conform to outer surfaces of the first and second outer tubular members, 634, 636, secured together. Preferably, the assembly inside the mold is heated by conduction, i.e., from the heated mold wall. As best illustrated in FIG. 49, showing a transverse cross section taken along lines 49-49 in FIG. 48, the resulting applied outer band member has an hourglass shape corresponding the shape of the exposed surfaces of the first and second outer tubular members 634, 636, brought together. The molding process thus avoids the tendency of shrink tubing to shrink down to an oval, non-hourglass, transverse cross-sectional shape around the two outer tubular members 634, 636. As a result, a potential gap between a part of the inner surface of the heat shrunk outer band member and the outer surface of the outer tubular members thereunder is thus avoided, for improved catheter performance. In a presently preferred embodiment, the outer band members 627, 628 are heat shrunk onto the outer tubular members 634, 636, with adhesive therebetween, and molded to conform to the outer surfaces of the outer tubular members 634, 636, to form a secure, low profile attachment with no gaps between the adjacent surfaces.

FIG. 46 illustrates the first and second branches joined together by a joining guidewire 637, and with the balloons in a deflated configuration prior to being inflated. For ease of illustration a space is shown between the inner surfaces of the balloons and the inner members therein, although it should be understood that the inner surface of the balloon along the inflatable interior is typically collapsed down to the inner member of the shaft in the deflated configuration to minimize the profile of the device during positioning in the body lumen. The distal end of the joining guidewire 637 is positioned within coupler 639 which is secured to the second branch and which is located distal to the inflatable interior of the second balloon 612, configured for releasably coupling the first and second branches together to form a coupled configuration. A second guidewire 641 is illustrated slidably disposed in the guidewire lumen 626.

The catheter 600 further includes a polymeric radiopaque distal tip marker 643 surrounding a distal end section of the first 617 lumen, formed of a blend of polymeric and radiopaque material. A presently preferred blend has about 91 weight percent of a radiopaque material such as tungsten. In the illustrated embodiment, the polymeric radiopaque distal tip marker 643 is an annular ring on an outer surface of a distal end section of the first branch 617 (see FIG. 50 illustrating an enlarged longitudinal cross section of the distal end of the first branch 617 taken within circle 50 in FIG. 46, and FIG. 51 illustrating a transverse cross section taken along line 51-51 in FIG. 50).

In embodiment of FIG. 50, the first branch includes a distal tip member 644 at the distal end of the first branch 617 having a joining wire lumen therein (i.e., the distal tip member 644 defines the distal-most end section of the joining wire lumen, in communication with the section of the joining wire lumen defined by the first inner tubular member 633) The polymeric radiopaque tip marker 643 surrounds and is secured to an outer surface of a section of an outer sheath on the distal tip member 644. However, in an alternative embodiment (not shown), the annular ring marker 643 is omitted, and the distal tip member 644 is formed of the blend of polymeric and radiopaque materials to thereby function as the polymeric radiopaque distal tip marker. In the embodiment of FIG. 50, the distal tip member 644 is butt-joined to the distal end of the first inner tubular member 633, and an outer sheath surrounds the distal end of the first branch and the proximal end of the distal tip member 644, although a variety of suitable configurations can be used. In the illustrated embodiment, the outer sheath is a polymeric sleeve member 645 extending from the distal end of the balloon 611 and sealingly surrounding the butt-joint. In an alternative embodiment, the sleeve member 645 is omitted and the balloon distal skirt section, sealingly secured to the shaft, forms the outer sheath extending over the butt-joint. The outer sheath is preferably nonradiopaque. In the illustrated embodiment, the polymeric sleeve member 645 extends distally to the distal end of the distal tip member 644, although in alternative embodiments (not shown) the length of the sleeve member 645 can vary.

The distal tip member 644 is typically formed of a relatively soft polymeric material, to provide an atraumatic distal tip. The soft distal tip member 644 and/or polymeric sleeve member 645 typically have at least an outer layer formed of a polymeric material compatible with the polymeric material of the polymeric radiopaque tip marker 643. For example, in a presently preferred embodiment, the soft distal tip member, polymeric sleeve, and the polymeric radiopaque distal tip marker are formed of polyether block amide copolymers (PEBAX) having the same or different durometer hardnesses. In one embodiment, the distal tip member 644 and marker 643 are formed of PEBAX 63D.

The polymeric radiopaque distal tip marker 643 is typically heat fusion bonded to the first branch of the catheter. During heat fusion, e.g. laser, bonding, the polymeric radiopaque distal tip marker 643 typically softens and flows. Although allowed to flow during bonding, the marker 643 typically retains a band-like shape. The marker shown in FIG. 50 has sharp edges for ease of illustration, however, it should be understood that the laser bonded polymeric radiopaque distal tip marker 643 typically has rounded edges, and preferably provides a gradual stiffness transition, unlike a metal marker band. Although not illustrated, in one embodiment the polymeric radiopaque tip marker 643 is shaped so that after being bonded to the shaft it has a distally tapering wall thickness for improved tip entry/track performance.

The catheter includes one or more balloon radiopaque markers 646 on the inner tubular members 633, 636, located within the inflatable interiors of the balloons 611, 612. The balloon radiopaque markers 646 indicate the proximal end, the distal end and the central opening of the stent 613. In a presently preferred embodiment, the polymeric radiopaque tip marker 643 appears under fluoroscopy with a shape that is visually different than balloon radiopaque markers 646. For example, in a presently preferred embodiment, the balloon radiopaque markers 646 are metallic radiopaque rings (i.e., they consist essentially of metal such as Pt/Ir, and not a polymeric radiopaque blend), which appear under fluoroscopy with a sharper, less rounded image than the polymeric radiopaque distal tip ring 643 Additionally, depending on the radiopacity/percent loading of the polymeric radiopaque blend, the metallic radiopaque rings 646 are typically brighter (more highly radiopaque) than the polymeric radiopaque blend Because the balloon metal markers are typically very bright with distinct edges compared to the polymeric blend marker on the tip, the ability to tell the different markers apart under fluoroscopy is facilitated. In an alternative embodiment, the balloon radiopaque markers 646 are also formed of a blend of polymeric and radiopaque materials, so that the polymeric radiopaque distal tip marker 643 preferably has a different physical characteristic such as length or shape than the balloon markers 646 or has a different radiopacity/percent loading than the balloon markers 646, to thereby appear visually different under fluoroscopy.

The polymeric radiopaque distal tip marker 643 has a length shorter than the length of the distal tip member 644, and is spaced apart from and between the distal end of the sleeve member 645 and from the distal end of the distal tip member 644. However, the polymeric radiopaque distal tip marker 643 can have a variety of suitable lengths. In one embodiment, the polymeric radiopaque distal tip marker 643 has a length which is about 0.5 mm to about 2 mm, preferably about 1 mm, and which is the same as the length of the balloon radiopaque markers 646. The polymeric radiopaque distal tip marker 643 typically has a relatively thin wall thickness, thinner than the underlying section of the shaft.

In the embodiment of FIG. 46, the joining wire 637 has a proximal end fixedly secured to a connector 620 connected to the proximal adapter 619. Thus, the joining wire 637 cannot be used to access the side branch of the patient's bifurcated body lumen and position the stent within the bifurcation, and the joining wire 637 is therefore removed from the catheter prior to stent deployment and replaced with a new guidewire having a torquer thereon for use in positioning the first balloon 611 in the side branch of the patient's body lumen.

In an alternative embodiment illustrated in FIG. 52, the catheter includes a guidewire locking mechanism 650 located proximal to the catheter shaft, having a locked mode in which the catheter is releasably locked to a joining guidewire 651, so that joining guidewire 651 does not have to be replaced with a new guidewire for accessing the side branch of the patient's body lumen. In the embodiment of FIG. 52, the guidewire locking mechanism 650 comprises a collet member 652 having a radially collapsible slotted head 653 positioned within the proximal adapter 619 (at least when in the locked mode), and a proximal fitting 654 (i.e., a luer cap) connected to the proximal adapter 619 and which tightens down onto the proximal adapter to place the guidewire locking mechanism in the locked mode. Specifically, as the proximal fitting 654 is rotated to tighten onto the proximal Y-arm adapter 619 luer connector, the jaws of the collet head are radially compressed on the joining guidewire, locking it in place. In the illustrated embodiment, the collet member is facing distally with the body of the collet member housed at least in part in the proximal fitting 654, although it can alternatively face proximally with the body housed in the guidewire lumen of the proximal adapter. The joining guidewire 651 is disposed in lumen 655 in the proximal fitting 654 and in the collet member 652 lumen, and has a proximal end extending proximally from the proximal end of the proximal fitting 654.

However, a variety of suitable guidewire locking mechanisms can be used, including forming the radially collapsible slotted head as an integral (e.g., molded) part of the proximal fitting 654. For example, FIG. 53 illustrates an embodiment in which the guidewire locking mechanism 650 is a proximal fitting 656 releasably connected to the proximal adapter 619 luer fitting, and having an inner extension member 657 with a radially collapsible slotted head 658 configured to releasably lock to joining guidewire 651 when the proximal fitting is tightened onto the proximal adapter.

FIG. 54 illustrates an alternative embodiment in which the guidewire locking mechanism 650 includes a guidewire locking torque handle 663 The guidewire locking torque handle 663 is releasably connected to a proximal end of the proximal adapter 619, to lock the joining guidewire 651 to the catheter as discussed above in relation to the guidewire locking mechanism of FIG. 52. Thus, the releasable connection between the proximal adapter 619 and the fitting 662 of the handle assembly in the embodiment illustrated in FIG. 50 is formed by a threaded luer type fitting. Additionally, with the guidewire locking torque handle 663 and proximal fitting 662 tightened together, the slotted head of the collet 665 reversibly engages the joining guidewire 651, such that the body 663 extending therealong provides a finger hold for use as a torque handle for manipulating the joining guidewire 651. The proximal fitting 662 can alternatively be a rotating type of luer fitting, allowing the joining guidewire 651 to be rotated while fixing the axial position of the wire 651.

In the embodiment of FIG. 54, the joining guidewire 651 can be unlocked from the catheter by disconnecting the proximal fitting 662 from the proximal adapter 619 (by rotating the proximal fitting 662 off the proximal adapter 619), and/or by disengaging the guidewire locking torque handle from the joining guidewire 651. For example, the collet can first be loosened, and then the device unlocked from the sidearm proximal adapter and slid along the joining guidewire, thus leaving the joining guidewire in place. The handle 663 is disengaged from the joining guidewire 651 the handle 663 from the cap formed by the proximal fitting 662. The location of the handle 663 on the joining guidewire 651 can be adjusted by sliding the disengaged handle along the joining guidewire, and then reengaging the handle onto the joining guidewire in the desired location by tightening the proximal fitting onto the handle. The handle 663, engaged on the joining guidewire 651, is then grasped during positioning of the joining guidewire in the patient's branch vessel. The joining guidewire 651 distal tip can be fixed in a retracted position within the lumen 625 of the catheter or in an extended position distally outside the catheter distal tip. Although discussed primarily in term of use with a bifurcated stent delivery catheter, it should be understood that the guidewire locking torque handle can be used with a variety of suitable catheters to provide a slidable guidewire in a stable and fixed position relative to the catheter in the releaseably locked configuration.

Figure 55:
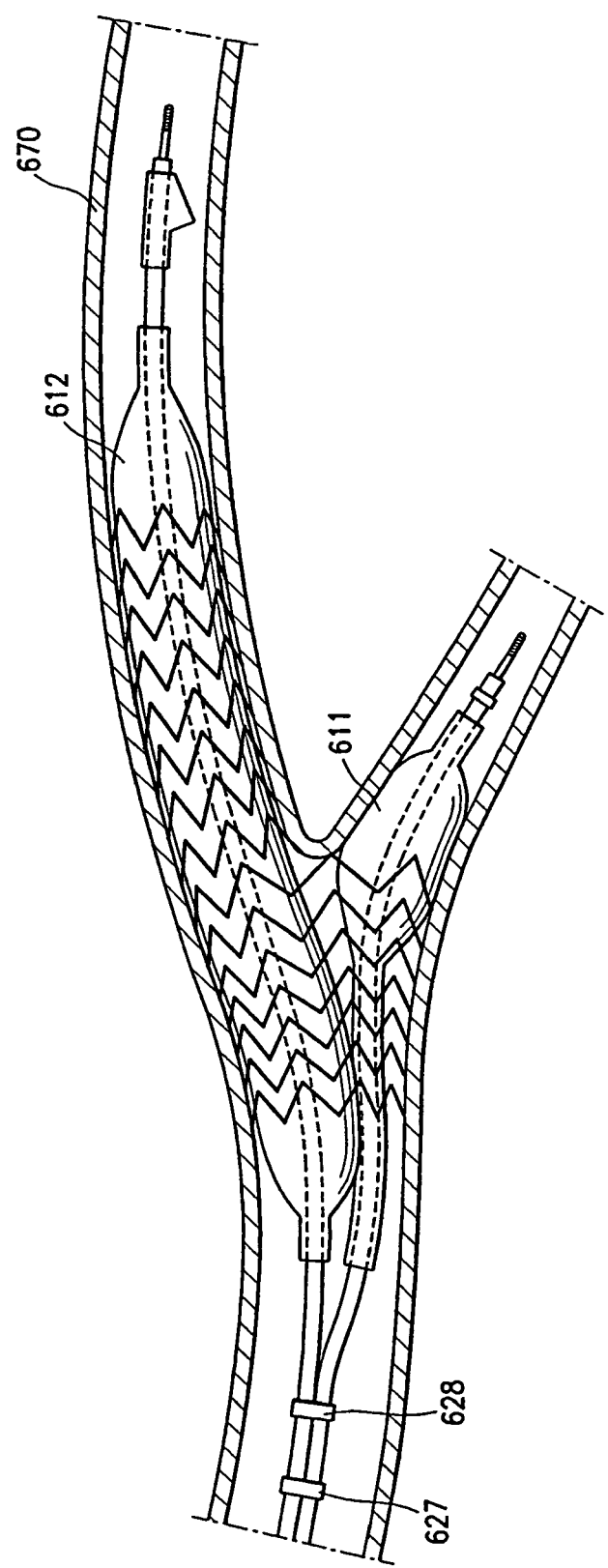
FIG. 55 illustrates the balloon catheter of FIG. 46 with the first branch of the catheter positioned within the side branch of the blood vessel, and with the balloons 611, 612 inflated to radially expand the stent at the blood vessel bifurcation.

A method of delivering a stent to a patient's bifurcated blood vessel generally comprises introducing within the blood vessel a stent delivery balloon catheter of the invention (e.g., catheter 600). The catheter is advanced within the patient's blood vessel towards a opening of a side branch of the patient's blood vessel, with the first and second branches of the catheter distal section in a reversibly coupled configuration. The method includes fluoroscopically imaging the polymeric radiopaque distal tip marker to determine the alignment of the first branch balloon relative to the opening of the side branch of the patient's blood vessel, uncoupling the first and second branches to an uncoupled configuration, positioning the uncoupled first branch of the catheter within the side branch of the patient's blood vessel, and expanding the stent. If necessary for proper placement, the alignment of the first branch balloon relative to the side branch opening of the patient's blood vessel is adjusted by fluoroscopically imaging the polymeric radiopaque distal tip marker either before or after the first and second branches are uncoupled. In the embodiment of FIG. 46, the first and second branches are held together at the secured portions 627, 628 to advance together as a unit within the body lumen. With the catheter advanced to the location of the opening of a side branch of the patient's blood vessel, the first branch is positioned in the side branch blood vessel by advancing the catheter in the uncoupled configuration, so that a distal tip of the uncoupled first branch advances radially away from the second branch into the side branch of the patient's blood vessel and the first and second branches advance together at the secured portion. FIG. 55 illustrates the an elevational view of balloon catheter 600 within a patient's bifurcated blood vessel 670, with the first branch of the catheter positioned within the side branch of the blood vessel, and with the balloons 611, 612 inflated to radially expand the stent at the blood vessel bifurcation.

In one embodiment, a method of the invention includes positioning the joining guidewire 651 distal end distal to the distal end of the first branch and placing the guidewire locking mechanism 650 in the locked mode to lock the catheter to the joining guidewire, so that the joining guidewire functions as a fixed guidewire. The catheter is then advanced together with the fixed guidewire to the opening of the branch vessel. In the unlocked mode, the joining guidewire is slidably disposed in the joining wire lumen and thus no longer functions as a fixed wire.

While particular forms of the invention have been illustrated and described, it will be apparent to those skilled in the art that various modifications can be made without departing from the scope of the invention. Accordingly, it is not intended that the invention be limited except by the appended claims.

What is claimed is:

1. A stent for treating a bifurcated vessel having a main vessel and a side branch vessel, comprising:
   cylindrical body having a proximal end, a distal end, and a plurality of rings;
   each ring having a delivered diameter, an implanted diameter and a plurality of peaks and a plurality of valleys, the peaks and the valleys being connected by bar arms;
   each ring being attached to an adjacent ring by more than one undulating link;
   a portal section comprised of one or more rings of the plurality of rings; and
   at least some of the bar arms connecting the peaks and the valleys of the one or more rings in the portal section have a length that is relatively longer than the bar arms connecting the peaks and the valleys of rings in a distal section of the stent, wherein at least a portion of a ring of said portal section is nested within a ring in said distal section of the stent such that spaces between adjacent said relatively longer bar arms of said ring of said portal section are circumferentially aligned with spaces between adjacent bar arms of said ring of said distal section so that upon stent expansion the portal section will extend into the side branch vessel.

2. The stent of claim 1, wherein two undulating links connect a portal ring to the adjacent ring distal to the portal ring.

3. The stent of claim 2, wherein the two undulating links comprise undulating portions that point in a direction away from a portal area and transverse to a longitudinal axis of the stent.

4. The stent of claim 1, wherein at least two undulating links connect adjacent rings.

5. The stent of claim 1, wherein three undulating links connect adjacent rings except that two links connect a portal ring to the adjacent ring distal to the portal ring.

6. The stent of claim 1, wherein at least some of the bar arms in the one or more rings of the portal section have a width that is less than a width of the bar arms in the rings not in the portal section.

7. The stent of claim 1, wherein the stent includes a proximal end ring, each of the peaks and the valleys of the proximal end ring having a radius that is greater than a radius of each of the peaks and the valleys of all of the other rings of the stent to improve stent retention and reduce flaring.

8. The stent of claim 1, wherein the stent is formed from a metal.

9. The stent of claim 8, wherein the metal is taken from the group of metals including stainless steel, titanium, nickel-titanium, cobalt-chromium, cobalt-chromium-vanadium, cobalt-chromium-tungsten, tungsten, gold, silver, platinum, and platinum-vanadium.

10. The stent of claim 1, wherein the stent is coated with at least one layer containing a drug.

11. The stent of claim 1, wherein the stent is coated with a therapeutic agent.

12. The stent of claim 1, wherein the stent is coated with a primer material which adheres to the stent, the primer material being coated with a drug or therapeutic agent or a layer containing a drug or therapeutic agent.

13. The stent of claim 1, wherein the relatively longer bar arms connecting the peaks and the valleys of the one or more rings in the portal section are configured to move the undulating links in the portal section closer to the side branch vessel when the stent is expanded to the implanted diameter.

14. The stent of claim 1, wherein the undulating links in the portal section are substantially longer than the undulating links not in the portal section so that as the stent is expanded, the portal section will extend further into the side branch vessel.

15. The stent of claim 1, wherein the rings and undulating links have a constant radial thickness.

16. The stent of claim 1, wherein the rings and undulating links have variable radial thickness to vary the flexibility of the stent.

17. The stent of claim 1, wherein at least some of the bar arms connecting the peaks and the valleys of the rings in a proximal section have a length that is relatively longer than the bar arms connecting the peaks and the valleys of rings in the distal section of the stent.

18. The stent of claim 1, wherein the location of the portal section on the stent can vary by increasing or decreasing the number of rings in a proximal section and/or the distal section.

19. The stent of claim 1, wherein a proximal section has a proximal end ring having peaks and valleys connected by bar arms, each of the peaks, the valleys and the bar arms of the proximal end ring having width greater than a width of the peaks, the valleys and the bar arms respectively of all of the other rings of the stent.

20. The stent of claim 1, wherein the stent is formed from a bioabsorbable polymer.

21. The stent of claim 1, wherein the stent is coated with a primer material which adheres to the stent, a drug or therapeutic agent being embedded in the primer.

* * * * *